US006762029B2

(12) United States Patent
Conley et al.

(10) Patent No.: US 6,762,029 B2
(45) Date of Patent: Jul. 13, 2004

(54) METHODS OF IDENTIFYING AGENTS THAT MODULATE P2Y$_{12}$ RECEPTOR ACTIVITY

(75) Inventors: Pamela B. Conley, Palo Alto, CA (US); Hans-Michael Jantzen, San Francisco, CA (US); Vanitha Ramakrishnan-DuBridge, Belmont, CA (US); David Jay Julius, San Francisco, CA (US); Gunther Hollopeter, San Francisco, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/745,842

(22) Filed: Dec. 26, 2000

(65) Prior Publication Data

US 2003/0170777 A1 Sep. 11, 2003

Related U.S. Application Data

(60) Provisional application No. 60/171,622, filed on Dec. 23, 1999.

(51) Int. Cl.$^7$ ..................... G01N 33/53; G01N 33/567; C07K 14/00; C07H 21/04
(52) U.S. Cl. ........................ 435/7.1; 435/7.1; 435/7.21; 435/7.8; 530/350; 536/24.3
(58) Field of Search ................................. 435/7.1, 7.21, 435/7.8, 69.1, 70.1, 90; 530/350, 351; 536/24.3

(56) References Cited

U.S. PATENT DOCUMENTS

| | | | |
|---|---|---|---|
| 6,060,272 A | 5/2000 | Li et al. | 435/69.1 |
| 2001/0046497 A1 | 11/2001 | Zhang et al. | 424/143.1 |

FOREIGN PATENT DOCUMENTS

| | | |
|---|---|---|
| DE | 10020073 A1 | 4/2000 |
| WO | WO 98/50549 A2 | 11/1998 |
| WO | 98/50549 | 11/1998 |
| WO | WO 00/28028 A1 | 5/2000 |
| WO | WO 00/34333 A1 | 6/2000 |
| WO | WO 01/46454 A1 | 6/2001 |
| WO | WO 01/57190 A2 | 8/2001 |
| WO | WO 01/85791 A1 | 11/2001 |
| WO | WO 02/02599 A2 | 1/2002 |
| WO | WO 02/24942 A2 | 3/2002 |
| WO | WO 00/22131 A2 | 4/2002 |
| WO | WO 02/36631 A1 | 5/2002 |
| WO | WO 00/31258 A2 | 6/2002 |

OTHER PUBLICATIONS

Hollopeter et al. Identification of the Platelet ADP Receptor Targeted by Antithrombotic Drugs, (2001), Nature, 409, pp 202–207.*
Jin et al. Molecular Basis for ADP–induced Platelet Activation (1998), Journal of Biological Chemistry, 273, pp2030–2034.*
Ngo et al., 1994, The Protein Folding Problem and Tertiary Structure Prediction, pp. 492–495.*
Wells, Aditivity of Mutational Effects in Proteins, 1990, Biochemistry, vol. 26, No.: 37, pp. 8509–8517.*
Humbert, M. et al. Ultrastructural studies of platelet aggregates from human subjects receiving clopidogrel and from a patient with an inherited defect of an ADP–dependent pathway of platelet activation. Arterioscler Thromb Vasc Biol 16, 1532–43 (1996).
Humphries, R. G., Tomlinson, W., Ingall, A. H., Cage, P. A. & Leff, P. A novel, highly potent and selective antagonist at human platelet P2T–purinoreceptors, Br. J. Pharmacol. 113, 1057–1063 (1994).
International Search Report for PCT/US00/34998 (Apr. 30, 2001).
Jantzen, H.–M. et al. Evidence for two distinct G protein–coupled ADP receptors mediating platelet activation. Blood 92, 303a (1998).
Jantzen, H. M. et al. Evidence for two distinct G–protein–coupled ADP receptors mediating platelet activation. Thromb Haemost 81, 111–7 (1999).
Jarvis, G. E., Humphries, R. G., Robertson, M. J. & Leff, P. ADP can induce aggregation of human platelets via both P2Y(1) and P(2T) receptors. Br J Pharmacol 129, 275–82 (2000).
Krapivinsky, G., Krapivinsky, L., Wickman, K. & Clapham, D. G bg binds directly to the G protein–gated K+ channel, IKACh. J. Biol. Chem. 270, 29059–62 (1995).
Leon, C. et al. Defective platelet aggregation and increased resistance to thrombosis in purinergic P2Y1 receptor–mull mice. J Clin Invest 104, 1731–7 (1999).
MacFarlane, D. E., Srivastava, P. C. & Mills, D. C. B. 2–Methylthioadenosine[b–32P]diphosphate:An agonist and radioligand for the receptor that inhibits the accumulation of cyclic AMP in intact blood platelets, J. Clin. Invest. 71, 420–428 (1983).
Mills, D. C. ADP receptors on platelets. Thromb Haemost 76, 835–56 (1996).
Mills, D. C. B. et al. Clopidogrel inhibits the binding of ADP analogues to the receptor mediating inhibition of platelet adenylate cyclase. Arterioscler. Thromb. 12, 430–436 (1992).
Nurden, P. et al. An inherited bleeding disorder linked to a defective interaction between ADP and its receptor on platelets. J. Clin. Invest. 95, 1612–22 (1995).
Ohlmann, P. et al. The human platelet ADP receptor activates Gi2 proteins. Biochem J 312, 775–9 (1995).

(List continued on next page.)

Primary Examiner—Lorraine Spector
Assistant Examiner—Jegatheesan Seharaseyon
(74) Attorney, Agent, or Firm—Townsend and Townsend and Crew LLP

(57) ABSTRACT

The present invention includes a novel subtype of the P2-purinergic receptor, referred to as the P2Y$_{12}$ receptor. This receptor is expressed selectively in the platelets and brain, and couples to a pertussis toxin-sensitive G protein (Gi). Nucleic acids encoding the receptor and associated screening and therapeutic methods are also disclosed.

17 Claims, 17 Drawing Sheets

OTHER PUBLICATIONS

Palmer, R. K., Boyer, J. L., Schachter, J. B., Nicholas, R. A. & Harden, T. K. Agonist action of adenosine triphosphates at the human P2Y1 receptor. Mol Pharmacol 54, 1118–23 (1998).

Published United States Patent Application 20020052043 (May 2, 2002).

Stewart, E. et al. An STS–based radiation hybrid map of the human genome. Genome Res. 7, 422–33 (1997).

Bennett, C. L. et al. Thrombotic thrombocytopenic purpura associated with Clopidogrel. *N. Eng. J. Med.* 325, 1371–2 (2000).

BLAST Search Report for P2Y12 (2002).

Boyer, J. L., Lazarowski, E. R., Chen, X. H. & Harden, T. K. Identification of a P2Y–purinergic receptor that inhibits adenylyl cyclase. *J Pharmacol Exp Ther* 267, 1140–6 (1993).

Boyer, J. L., Romero–Avila, T., Schachter, J. B. & Harden, T. K. Identification of competitive antagonists of the $P2Y_1$ receptor. *Mol Pharmacol* 50, 1323–9 (1996).

Caterina, M. J. et al. The capsaicin receptor: a heat–activated ion channel in the pain pathway. *Nature* 389, 816–824 (1997).

Cattaneo, M. & Gachet, C. ADP receptors and clinical bleeding disorders. *Arterioscler Throm Vasc Biol* 19, 2281–5 (1999).

Chambers, J. K. et al. A G protein–coupled receptor for UDP–glucose. *J Biol Chem* 275, 10767–71 (2000).

Daniel, J. L. et al. Molecular basis for ADP–induced platelet activation. I. Evidence for three distinct ADP receptors on human platelets. J Biol Chem 273, 2024–9 (1998).

Fabre, J. E. et al. Decreased platelet aggregation, increased bleeding time and resistance to thromboembolism in P2Y1–deficient mice. Nat Med 5, 1199–202 (1999).

Filippov, A. K., Brown, D. A. & Barnard, E. A. The P2Y1 receptor closes the N–type Ca(2+) channel in neurones, with both adenosine triphosphates and diphosphates as potent agonists. Br J Pharmacol 129, 1063–6 (2000).

Gachet, C. et al. ADP receptor induced activation of guanine nucleotide binding proteins in rat platelet membranes–an effect selectively blocked by the thienopyridine clopidogrel. Thromb Haemost 68, 79–83 (1992).

Gachet, C. et al. The thienopyridine ticlopidine selectively prevents the inhibitory effects of ADP but not of adrenaline on cAMP levels raised by stimulation on the adenylate cyclase of human platelets by PGE1. Biochem Pharmacol 40, 2683–7 (1990).

Hechler, B., Eckly, A., Ohlmann, P., Cazenave, J.–P. & Gachet, C. The P2Y1 receptor, necessary but not sufficient to support full ADP–induced platelet aggregation, is not the target of the drug clopidogrel. Br. J. Haematology 103, 858–866 (1998).

Hollopeter et al., Identification of the platelet ADP receptor targeted by antithrombotic drugs. Nature. 409, 202–207, (2001).

Hourani, S. M. O. & Hall, D. Receptors for ADP on human blood platelets. Trends Pharmacol. Sci. 15, 103–108 (1994).

Database Accession AF313449 NCBI: GenBank Database (2001).

Database Accession AC024886 NCBI: GenBank Database (2002).

Database Accession BC017898 NCBI: GenBank Database (2003).

Database Accession BC027381 NCBI: GenBank Database (2003).

Database Accession Q9H244 NCBI: GenBank Database (2003).

Database Accession Q95KC3 NCBI: GenBank Database (2002).

Database Accession Q9CPV9 NCBI: GenBank Database (2003).

Database Accession AB056385 NCBI: GenBank Database (2001).

Database Accession A48642 NCBI: GenBank Database (2000).

Database Accession BC025428 NCBI: GenBank Database (2003).

Database Accession AB062981 NCBI: GenBank Database (2001).

Database Accession AF313450 NCBI: GenBank Database (2001).

Database Accession AF321815 NCBI: GenBank Database (2001).

Database Accession AF310685 NCBI: GenBank Database (2001).

Database Accession AX369349 NCBI: GenBank Database (2002).

Database Accession AB052684 NCBI: GenBank Database (2001).

Database Accession AB083596 NCBI: GenBank Database (2002).

Database Accession AB056385 NCBI: GenBank Database (2001).

Database Accession AK013804 NCBI: GenBank Database (2003).

Database Accession AK033448 NCBI: GenBank Database (2003).

Database Accession AK014807 NCBI: GenBank Database (2003).

Database Accession BC025428 NCBI: GenBank Database (2003).

Database Accession W81576 NCBI: GenBank Database (1996).

Database Accession B02840 NCBI: GenBank Database (1996).

Database Accession M79249 NCBI: GenBank Database (1992).

Database Accession E04386 NCBI: GenBank Database (1997).

Database Accession G80236 NCBI: Genbank Database (2002).

Database Accession E04385 NCBI: GenBank Database (1997).

Database Accession E04384 NCBI: GenBank Database (1997).

Database Accession E04387 NCBI: GenBank Database (1997).

Database Accession AAA33582 NCBI: GenBank Database (1993).

Database Accession J05075 NCBI: GenBank Database (1993).

Database Accession D12481 NCBI: GenBank Database (2003).

Database Accession A46034 NCBI: GenBank Database (1997).

* cited by examiner

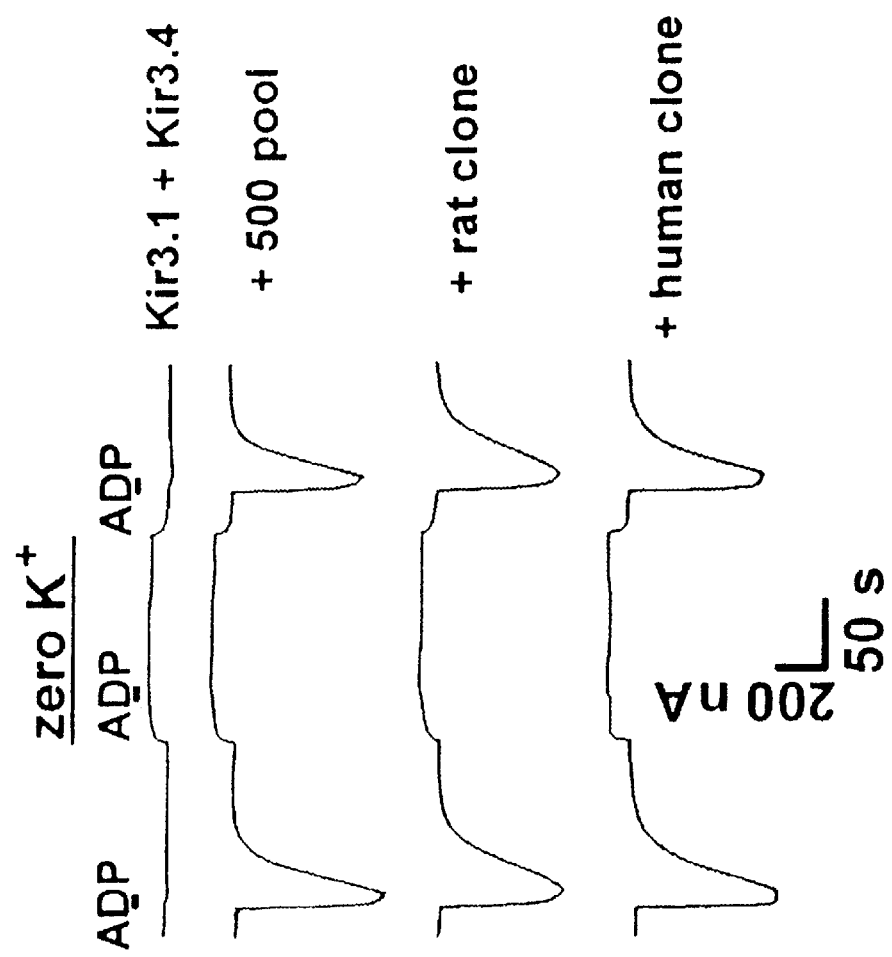

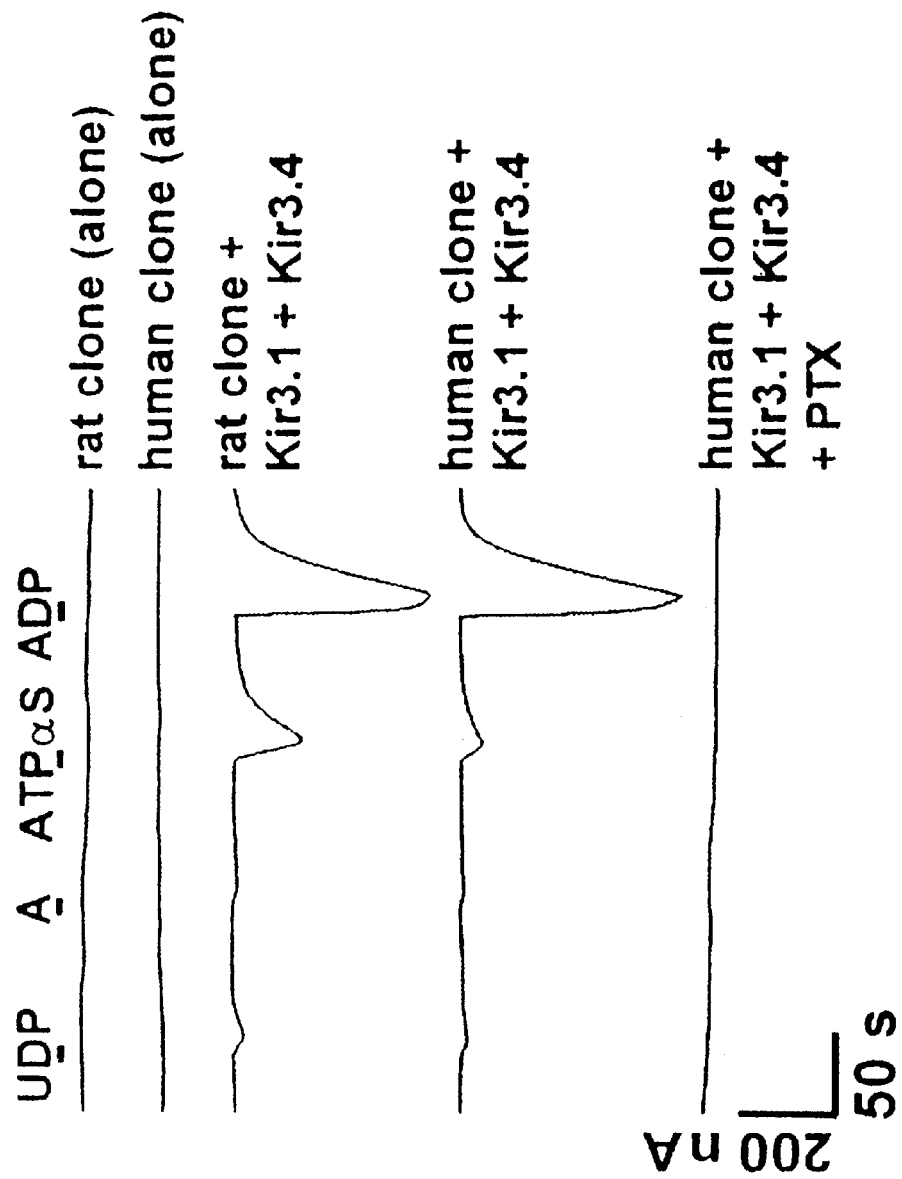

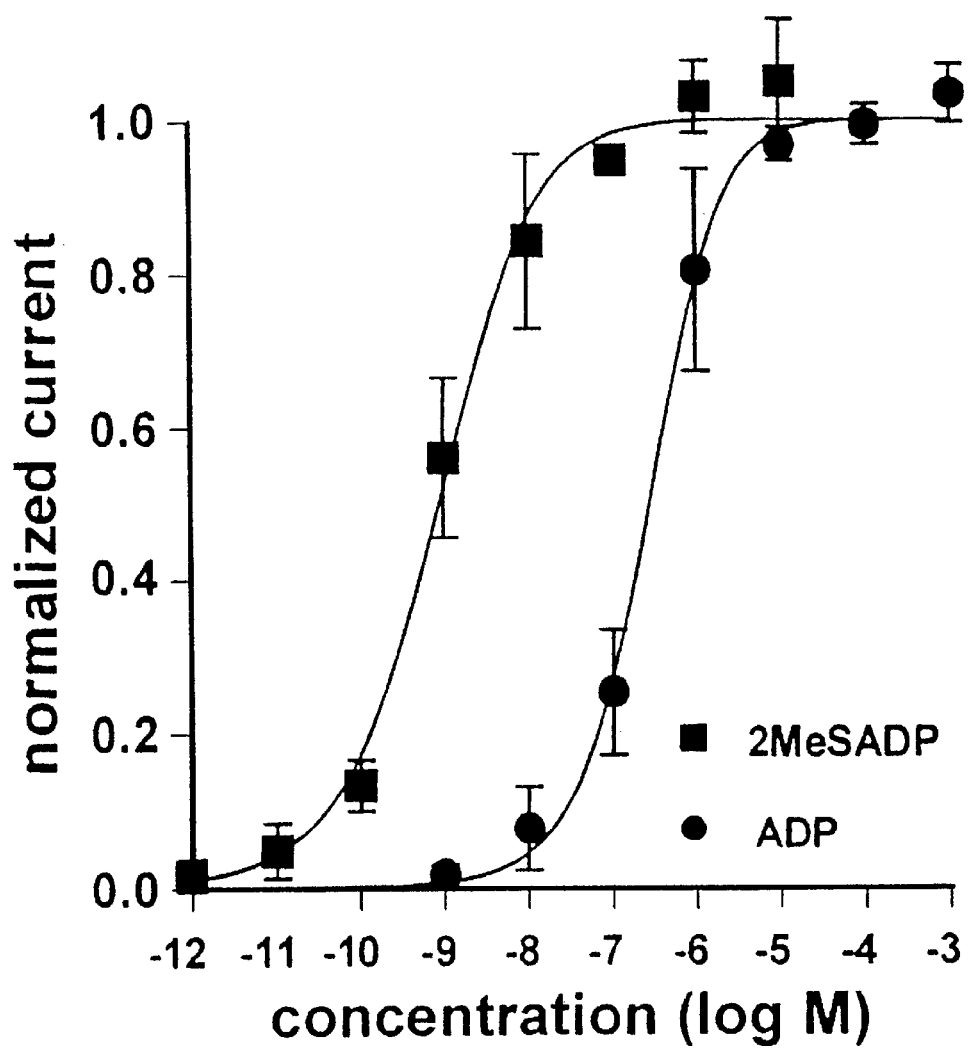

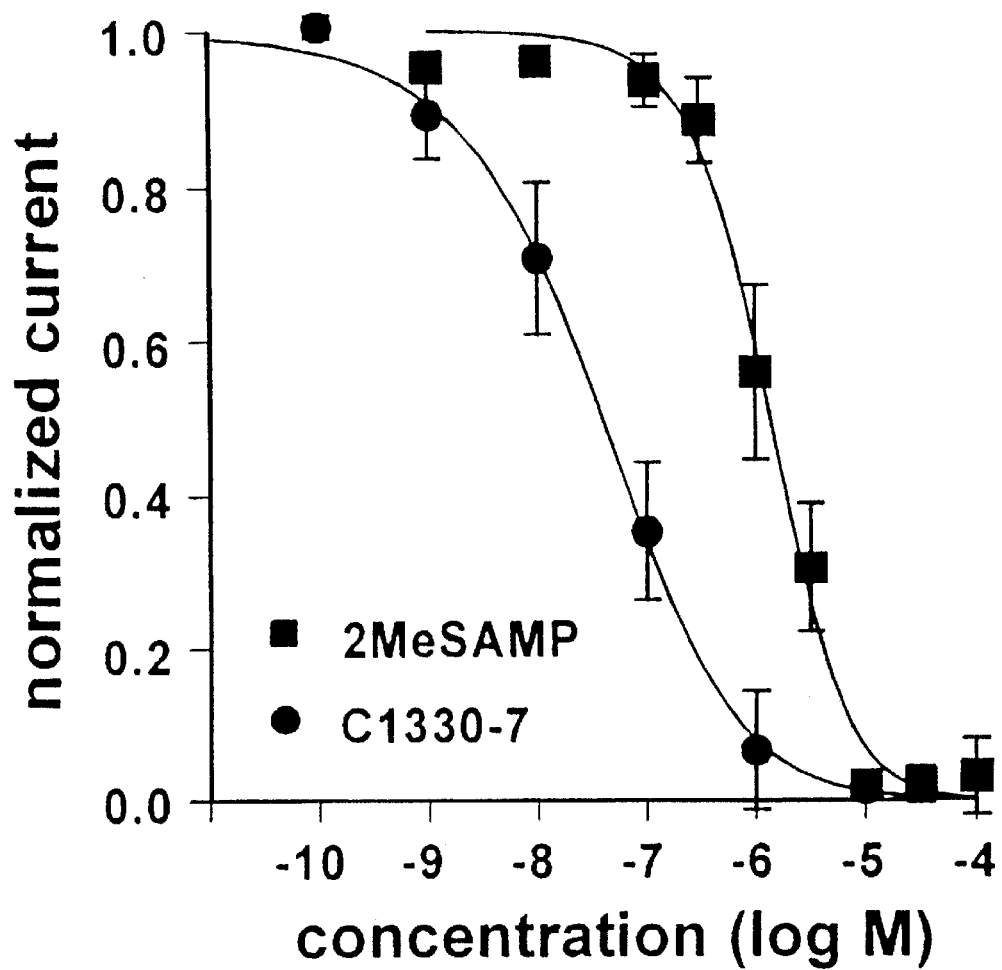

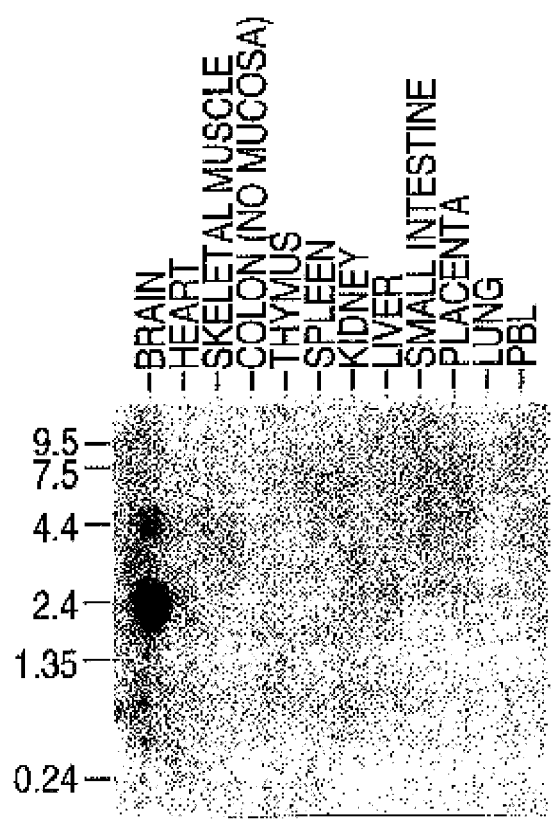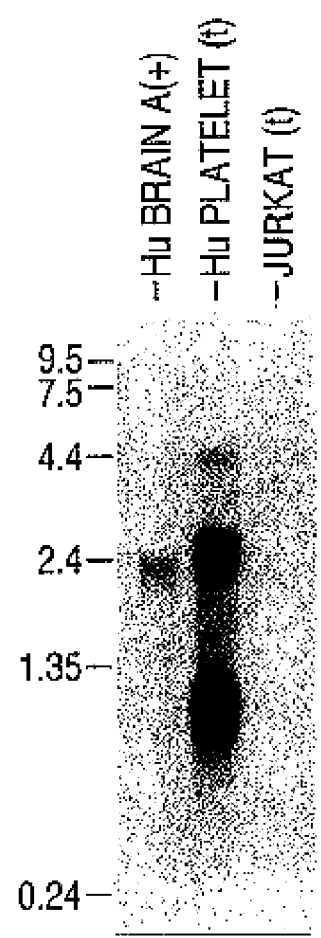

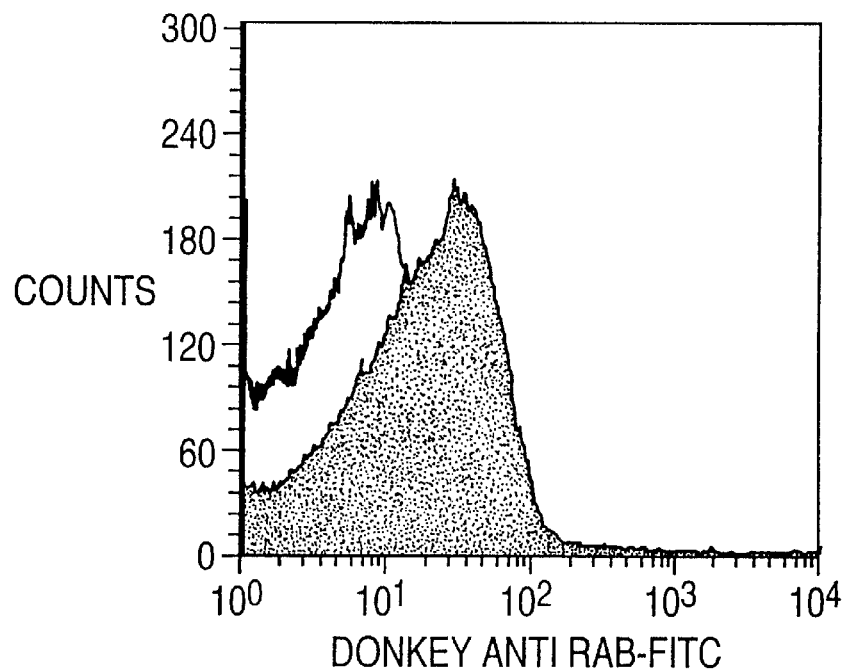
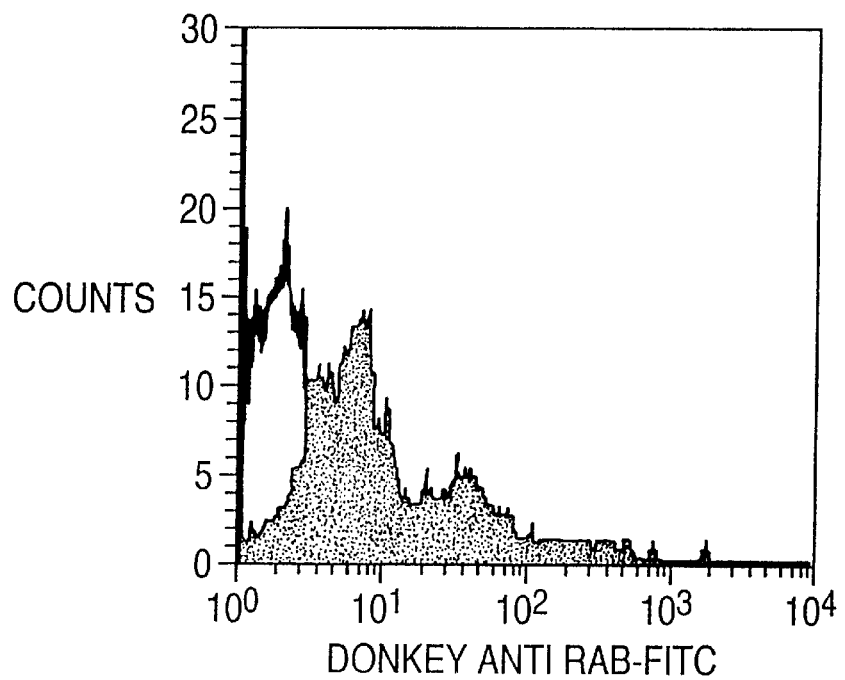

FIG. 5B

```
                     236   V    K    V    F    I    I    A    V    F    F
Wild type aa
Wild type nucleotide       GTC  AAA GTT TTT CAT TAT CAT TGC TGT ATT CTT T
Mutant nucleotide          GTC  AAA GTT TTT --T TAT CAT TGC TGT ATT CTT
Mutant aa            236   V    K    V    F         Y    H    C    I    L
```

[3H]2MeSADP BINDING TO MEMBRANES OF COS7 CELLS TRANSIENTLY TRANSFECTED WITH hP2Y12

COMPETITION BY 2MeSAMP AND A3P5P OF 1nM [3H]2MeSADP BINDING TO MEMBRANES FROM cos7 CELLS TRANSFECTED WITH hP2Y12

RESPONSE OF OOCYTES INJECTED WITH cRNA FOR H11 GPCR AND GIRK1 & 4 cRNA's

DRUG APPLICATIONS:
   1) 1μM ADP 30s
   2) 1μM ADP AND 10μM A3P5P 30s
   3) 1μM ADP AND 10μM 2MeSAMP 30s
   4) 1μM ADP AND 10μM CT COMPOUND 30s

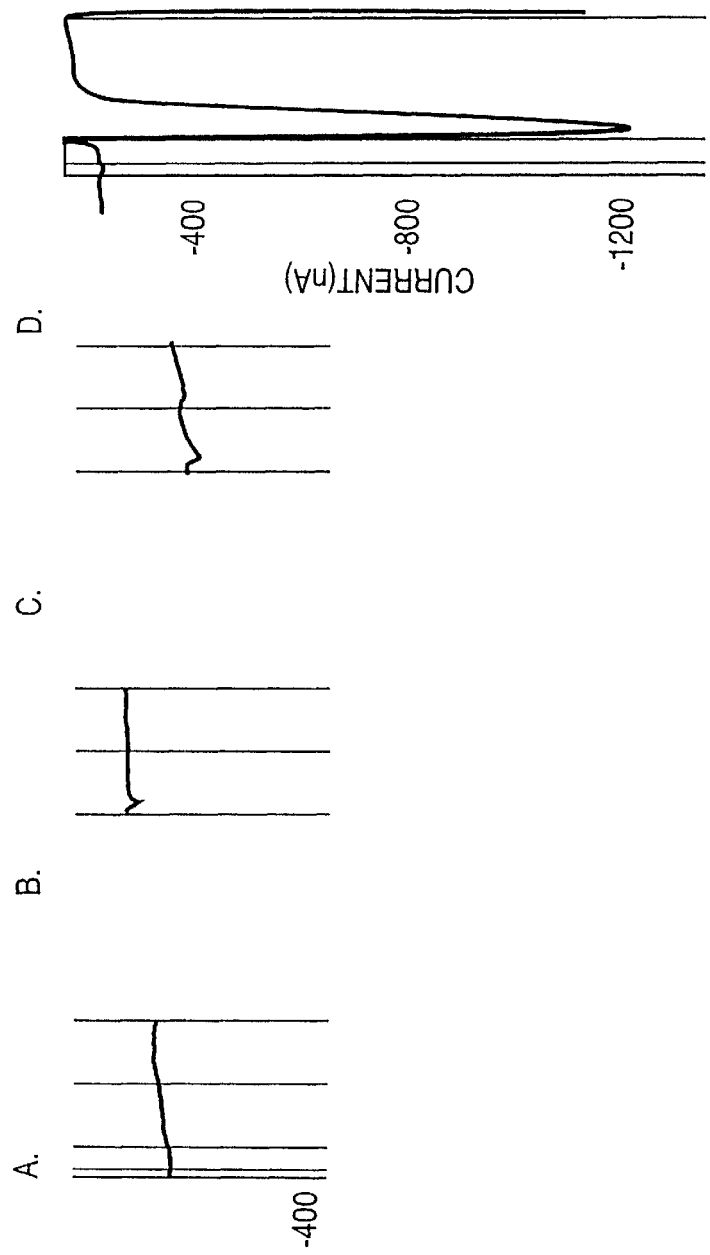

METHODS OF IDENTIFYING AGENTS THAT MODULATE P2Y$_{12}$ RECEPTOR ACTIVITY

CROSS-REFERENCES TO RELATED APPLICATIONS

This application is related to Provisional Application No. 60/171,622, entitled Novel ADP Receptor, filed Dec. 23, 1999, which is herein incorporated by reference in its entirety.

FIELD OF THE INVENTION

The present invention relates to methods employing an ADP receptor, termed the P2Y$_{12}$ receptor, and its encoding nucleic acid molecules. The invention also relates to methods for the recombinant production of the receptor proteins and the proteins made by these methods, antibodies against the whole receptor or regions thereof, vectors, nucleotide probes, host cells transformed by genes encoding polypeptides having the receptor activity, methods for the discovery of novel modulators of receptor activity, along with diagnostic and therapeutic uses for these various agents.

BACKGROUND OF THE INVENTION

Thrombotic complications are a major cause of death in the industrialized world. Examples of these complications include acute myocardial infarction, unstable angina, chronic stable angina, transient ischemic attacks, strokes, peripheral vascular disease, preeclampsia, deep venous thrombosis, embolism, disseminated intravascular coagulation and thrombotic thrombocytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and prostheses.

It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation of platelets by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) Thromb. Hemost. 76:835–56). Therefore, platelet ADP receptors are members of the family of P2 receptors activated by purine and/or pyrimidine nucleotides (King, B. F., Townsend-Nicholson, A. & Burnstock, G. (1998) Trends Pharmacol. Sci. 19:506–514). ADP receptors additionally have been characterized as belonging to the G protein-coupled receptor superfamily.

Studies of inherited disorders in humans and rats which result in a reduction of ADP release from platelets or reduced ADP receptor number and signaling confirm the critical role in platelet aggregation of ADP and the ADP receptors (Cattaneo M. & Gachet C., Arterioscler. Thromb. Vasc. Biol. (1999) 19:2281–2285). Inhibitors of ADP-induced platelet aggregation are efficacious antithrombotic drugs.

Recent pharmacological data using selective antagonists suggests that ADP-dependent platelet aggregation requires activation of at least two ADP receptors (Kunapuli, S. P. (1998) TIPS 19:391–394; Kunapuli S. P. et al., (1998) Biochem J. 336:513–523; Jantzen, H. M. et al., (1999) Thromb. Haemost. 81:111–117). One receptor appears to be identical to the cloned P2Y$_1$ receptor, is coupled to the G protein G$_q$ and mediates intracellular calcium mobilization. This receptor is also required for ADP-induced platelet shape change.

The second platelet ADP receptor couples to inhibition of adenylyl cyclase. The gene or cDNAs for this receptor has not been identified previously and the receptor has been provisionally termed P2Y$_{ADP}$ (Fredholm B. B. et al., (1997) TIPS 18:79–82), P2T$_{AC}$, (Kunapuli, S (1998) TIPS 19(10):391–394), and P2Ycyc based on its pharmacological and signaling properties. Based on the inhibition of adenylyl cyclase and the activation of the G protein Gαi2 by ADP in platelet membranes it was thought that this receptor may couple to Gi in vivo, and may belong to the G-protein coupled receptor family. This receptor also appears to be the target of the orally active antithrombotic drugs ticlopidine and clopidogrel, which appear to act through unstable and irreversible acting liver metabolites (Quinn, M. J. & Fitzgerald, D. J. (1999) Circulation 100:1667–1672). Patients with mild bleeding disorders have been identified with functional defects in this receptor (Cattaneo M. & Gachet C., Arterioscler. Thromb. Vasc. Biol. (1999) 19:2281–2285). The molecular identity of the G$_i$-linked receptor has remained elusive, even though it is the target of efficacious antithrombotic agents such as ticlopidine and clopidogrel (Gachet et al. (1990)). A sequence corresponding to this G$_i$-linked receptor was previously published in WO 98/50549, but its function was not identified.

Despite the previous physiological identification of a second ADP receptor and the discovery of agents that may act at this receptor, there exists a need for platelet ADP receptor inhibitors with improved properties.

SUMMARY OF THE INVENTION

The present inventors have cloned the G$_i$-linked receptor, designated P2Y$_{12}$, and show that a patient with a bleeding disorder (Nurden et al (1995)) is defective in this gene. Cloning of the P2Y$_{12}$ receptor facilitates the development of better antiplatelet agents to treat a variety of cardiovascular diseases.

The invention includes an isolated nucleic acid molecule selected from the group consisting of: (a) an isolated nucleic acid molecule that encodes the amino acid sequence of SEQ ID NO: 2, an isolated nucleic acid molecule that encodes the amino acid sequence of SEQ ID NO: 12 (b) an isolated nucleic acid molecule which hybridizes to the complement of a nucleic acid molecule comprising SEQ ID NO: 1 under conditions of sufficient stringency to produce a clear signal; and (c) an isolated nucleic acid molecule which hybridizes to a nucleic acid molecule that encodes the amino acid sequence of SEQ ID NO: 2 under conditions of sufficient stringency to produce a clear signal.

The present invention further includes isolated nucleic acid molecules wherein the nucleic acid molecule comprises the sequence of SEQ ID NO: 1, isolated nucleic acid molecules that comprise nucleotides 130–1158 of SEQ ID NO: 1 or nucleotides 130–1161 of SEQ ID NO: 1; isolated nucleic acid molecules that comprise the sequence of SEQ ID NO: 11, nucleic acid molecules that comprise nucleotides 73–873 of SEQ ID NO: 11 or nucleotides 73–876 of SEQ ID NO: 11.

The present invention further includes the nucleic acids operably linked to one or more expression control elements, including vectors comprising the isolated nucleic acid molecules. The invention further includes host cells transformed to contain the nucleic acids of the invention, wherein said host is selected selected from the group consisting of prokaryotic hosts and eukaryotic hosts and methods for producing a protein comprising the step of culturing a host cell under conditions in which the protein encoded by said nucleic acid molecule is expressed.

The invention further provides a polypeptide, which may be expressed in a recombinant cell or may be purified, selected from the group consisting of an isolated receptor polypeptide comprising the amino acid sequence of SEQ ID NO: 2, an isolated receptor polypeptide comprising the amino acid sequence of SEQ ID NO: 12.

The invention further provides an isolated antibody that binds to a polypeptide of the invention, including monoclonal and polyclonal antibodies.

The invention further provides a method of identifying an agent which modulates the expression of a nucleic acid encoding a $P2Y_{12}$ receptor comprising the steps of exposing cells which express the nucleic acid to the agent and determining whether the agent modulates expression of said nucleic acid, thereby identifying an agent which modulates the expression of a nucleic acid encoding the protein having the sequence of $P2Y_{12}$ receptor.

The invention further provides a method of identifying an agent which modulates at least one activity of a $P2Y_{12}$ receptor comprising the steps of exposing cells which express the protein to the agent; determining whether the agent modulates at least one activity of said protein, thereby identifying an agent which modulates at least one activity of a $P2Y_{12}$ receptor.

Activities the agent may modify include but are not limited to the interaction between ADP, ATP or a derivative thereof, and a $P2Y_{12}$ receptor; potassium current or adenylyl cyclase activity, platelet activation or thrombotic activity; acute myocardial infarction, unstable angina, chronic stable angina, transient ischemic attacks, strokes, peripheral vascular disease, preeclampsia, deep venous thrombosis, embolism, disseminated intravascular coagulation, thrombotic thrombocytopenic purpura or a bleeding disorder; thrombotic and restenotic complications following angioplasty, carotid endarterectomy, post CABG (coronary artery bypass graft) surgery, vascular graft surgery, stent placements or insertion of endovascular devices and prostheses.

The invention further provides a method of identifying binding partners for a $P2Y_{12}$ receptor protein comprising the steps of exposing said protein to a potential binding partner and determining if the potential binding partner binds to said protein, thereby identifying binding partners for a $P2Y_{12}$ receptor protein.

The invention further provides a method of modulating the expression of a nucleic acid encoding a $P2Y_{12}$ receptor protein comprising the step of administering an effective amount of an agent which modulates the expression of a nucleic acid encoding encoding a $P2Y_{12}$ receptor protein.

The invention further provides a method of modulating at least one activity of a $P2Y_{12}$ receptor protein comprising the step of administering an effective amount of an agent which modulates at least one activity of a $P2Y_{12}$ receptor protein.

The invention further provides a non-human transgenic animal modified to contain a nucleic acid molecule of the invention including a nucleic acid molecule which encode a $P2Y_{12}$ receptor or a truncation mutant of $P2Y_{12}$ receptor.

The invention further provides a method of diagnosing a disease state in a subject, comprising the step of determining the level of expression of a nucleic acid molecule encoding a $P2Y_{12}$ receptor.

The invention further provides a method of diagnosing a disease state in a subject, comprising the step of determining the level of expression of a $P2Y_{12}$ receptor protein.

The invention further provides an isolated mutant $P2Y_{12}$ receptor protein which is a naturally occurring truncation mutant, wherein said truncation is caused by a frame-shift mutation in the region of the gene encoding transmembrane domain six of the protein.

The invention further provides an isolated mutant $P2Y_{12}$ receptor protein which is a naturally occurring truncation mutant, wherein said truncation is caused by a frame-shift mutation in the region of the gene encoding transmembrane domain six of the protein wherein said protein is associated with a bleeding disorder.

The invention further provides an isolated mutant $P2Y_{12}$ receptor protein which is a naturally occurring truncation mutant, wherein said truncation is caused by a frame-shift mutation in the region of the gene encoding transmembrane domain six of the protein wherein said frame shift mutation introduces a stop codon in the gene encoding the $P2Y_{12}$ protein and results in platelets with impaired ADP-dependent platelet aggregation activity, reduced ADP binding activity and reduced ability to inhibit cAMP levels in response to ADP.

The invention further provides an isolated nucleic acid encoding a mutant $P2Y_{12}$ receptor protein which is a naturally occurring truncation mutant, wherein said truncation is caused by a frame-shift mutation in the region of the gene encoding transmembrane domain six of the protein.

The invention further provides an isolated nucleic acid encoding a mutant $P2Y_{12}$ receptor protein which is a naturally occurring truncation mutant, wherein said truncation is caused by a frame-shift mutation in the region of the gene encoding transmembrane domain six of the protein wherein said nucleic acid encodes a protein associated with a bleeding disorder.

The invention further provides an isolated nucleic acid encoding a mutant $P2Y_{12}$ receptor protein which is a naturally occurring truncation mutant, wherein said truncation is caused by a frame-shift mutation in the region of the gene encoding transmembrane domain six of the protein wherein said frame shift mutation introduces a stop codon in the gene encoding the $P2Y_{12}$ protein and results in platelets with impaired ADP-dependent platelet aggregation activity, reduced ADP binding activity and reduced ability to inhibit cAMP levels in response to ADP.

The invention further provides a method of diagnosing a disease state in a subject, comprising the step of determining the level of expression of a nucleic acid molecule of the invention.

The invention further provides a method of diagnosing a disease state in a subject, comprising the step of determining the level of expression of a protein of the invention.

The invention further provides a method of diagnosing a disease state in a subject, comprising the step of identifying a nucleic acid molecule of the invention.

BRIEF DESCRIPTION OF THE DRAWINGS

FIGS. 1A–1C P2Y$_{12}$ is a G protein-coupled receptor that responds to ADP. FIG. 1(A): Activation of potassium-dependent currents in *Xenopus oocytes* expressing P2Y$_{12}$ with Kir3.1 and 3.4. FIG. 1(B): ADP-selective stimulation of potassium channel-dependent currents by P2Y$_{12}$ occurs via a pertussis toxin-sensitive pathway. FIG. 1(C): The agonist profile of P2Y$_{12}$ recapitulates that observed for the G$_i$-coupled platelet ADP receptor.

FIGS. 2A–2C Currents stimulated by ADP in oocytes expressing hP2Y$_{12}$ with Kir3.1 and 3.4 are inhibited by 2MeSAMP, C1330–7 and a thiol reagent. FIG. 2(A): Current tracing showing reversible block of ADP (1 μM) responses by 2MeSAMP (10 μM) and C1330–7 (1 μM), but not A3P5P (300 μM). FIG. 2(B): 2MeSAMP and C1330–7 inhibition curves. FIG. 2(C): Selective ablation of P2Y$_{12}$ but not m2 muscarinic receptor signaling by the thiol reagent pCMBS.

FIG. 3(A): Receptor coupling to adenylyl cyclase. FIG. 3(B): The effect of the specific antagonists 2MeSAMP (2-MES)(50 μM) and C1330–7 (50 μM). FIG. 3(C): Effect of pertussis toxin (PTX) pretreatment.

FIGS. 4A–4E P2Y$_{12}$ receptor is selectively expressed in platelets and brain. FIGS. 4(A) and (B): Northern analysis of hP2Y$_{12}$ transcripts. FIG. 4(C): The rP2Y$_{12}$ protein is expressed in megakayocytes and platelets in rat bone marrow. FIG. 4(D): FACS analysis of rat platelets stained with rP2Y$_{12}$ antisera. FIG. 4(E): FACS analysis of rat 2–9 fibroblasts transfected with the rP2Y$_{12}$ cDNA clone.

FIGS. 5A–5D A frame-shift mutation within the hP2Y$_{12}$ gene is associated with a bleeding disorder. FIG. 5(A): Deduced amino acid sequence of the hP2Y$_{12}$ protein and alignment with other receptor sequences (SEQ ID NO: 6, SEQ ID NO: 13, SEQ ID NO: 14). FIG. 5(B): A P2Y$_{12}$ allele from a patient (ML) with defective ADP-dependent aggregation contains a 2 base pair deletion, resulting in a frame-shift mutation and a premature truncation of the protein (SEQ ID NO: 5, SEQ ID NO: 6, SEQ ID NO: 11, SEQ ID NO: 12). FIG. 5(C): Mutant hP2Y$_{12}$ receptor from patient ML is non-functional and does not act in a dominant-negative capacity. FIG. 5(D): Patient ML has abnormally low levels of RT-PCR product derived from P2Y$_{12}$ mRNA.

FIG. 6(A): [$^3$H]2MeSADP binding to membranes of COS7 cells transiently transfected with hP2Y$_{12}$. FIG. 6(B): Competition by 2MeSAMP and A3P5P of 1 nM [$^3$H]2MeSADP binding to membranes from COS7 cells transfected with hP2Y$_{12}$.

DETAILED DESCRIPTION OF THE PREFERRED EMBODIMENT

I. General Description

Figure 2A:
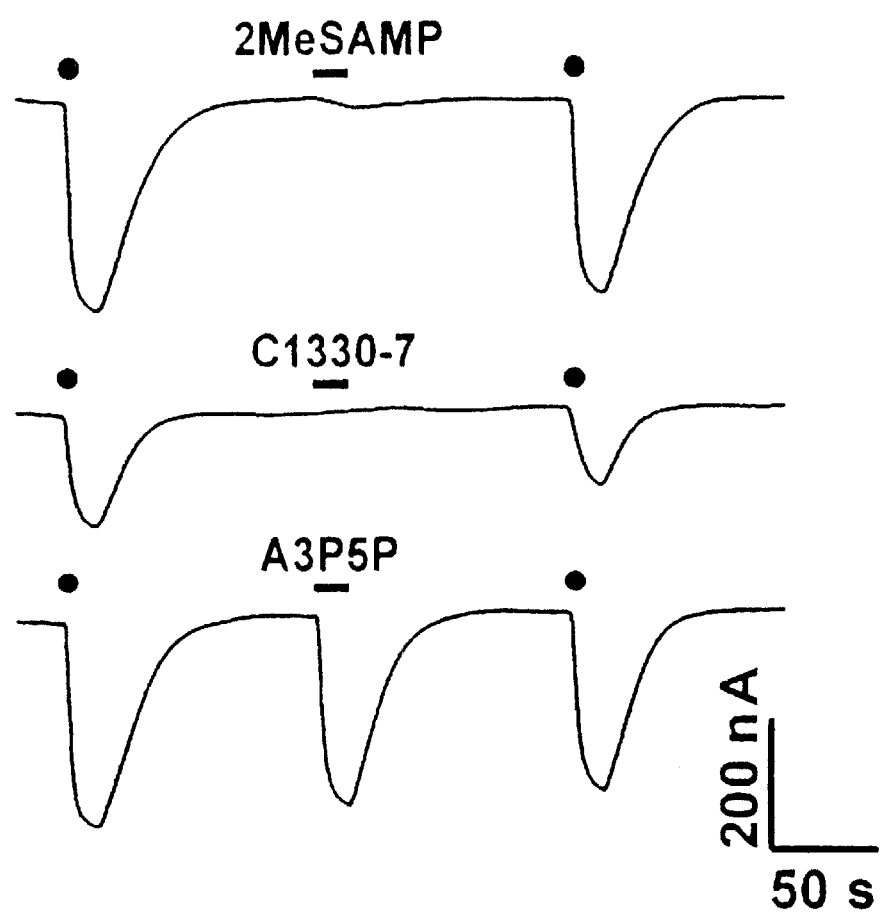

The present inventors have characterized a novel cDNA from a platelet library that encodes the G$_i$-linked platelet ADP receptor. Genetic (Leon et al. (1999); Fabre et al. (1999); Nurden et al (1995); Cattaneo et al. (1999)) and pharmacological (Jarvis et al. (2000); Hechler et al. (1998)) studies demonstrate that the G$_i$-linked receptor is critical for formation and stabilization of large platelet aggregates (Humbert et al. (1996)). Additionally, the G$_i$-linked receptor is the target of the antithrombotic drugs clopidogrel and ticlopidine, which have been demonstrated to be efficacious in the treatment of a variety of thrombotic diseases (stroke, MI, peripheral vascular disease). However, these drugs work through a mechanism of covalent protein modification, which may underlie their recent association with the syndrome thrombotic thrombocytopenic purpura (TTP) (Bennett et al. (2000)), an immune-mediated response. The present studies demonstrate that the P2Y$_{12}$ receptor has a selective tissue distribution compared to other purinergic receptors (such as P2Y$_1$), making this receptor an extremely attractive target for the development of novel antithrombotics.

The invention includes methods of using this receptor for identification of binding partners or for diagnostic applications. Additionally, the proteins of the invention provide targets for screening synthetic small molecules and combinatorial or naturally occurring compound libraries to discover therapeutics to regulate platelet aggregation, vascular injury or disease as well as schizophrenia, eating disorders, depression, migraine and other brain disorders.

II. Specific Embodiments

A. Protein Molecules

The present invention provides and employs isolated P2Y$_{12}$ receptor protein, allelic variants of the protein as well as conservative amino acid substitutions of the protein. As used herein, the "protein" or "polypeptide" refers in part to a protein that has the amino acid sequence depicted in SEQ ID NO: 2, SEQ ID NO: 4, SEQ ID NO: 6 or SEQ ID NO: 12. The methods of the invention also employ naturally occurring allelic variants and proteins that have a slightly different amino acid sequence than that specifically recited above. Allelic variants, though possessing a slightly different amino acid sequence than those recited above, will still have the same or similar biological functions associated with the 267, 315, 342 or 343 amino acid protein.

As used herein, the "family of proteins" related to the amino acid sequence of SEQ ID NO: 2, SEQ ID NO: 4, SEQ ID NO: 6 or SEQ ID NO: 12 refers to proteins that have been isolated from organisms in addition to rats and humans. The methods used to identify and isolate other members of the family of proteins related to the 267, 315, 342 or 343 amino acid protein are described below.

The proteins of the present invention may be in isolated form, may be recombinantly expressed so as to be present on the cell surface or may be in partially purified form, such as in cellular membrane preparations. For such preparations, the protein may be found at levels typically higher than normally found without recombinant expression of the protein. As used herein, a protein is said to be isolated when physical, mechanical or chemical methods are employed to remove the protein from cellular constituents that are normally associated with the protein. A skilled artisan can readily employ standard purification methods to obtain an isolated protein.

The proteins used in the methods of the invention further include insertion, deletion or conservative amino acid substitution variants of SEQ ID NO: 2, SEQ ID NO: 4, SEQ ID NO: 6 or SEQ ID NO:12. As used herein, a conservative variant refers to at least one alteration in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic/hydrophilic properties of the protein can be altered without adversely affecting a biological activity. Such biological activities of the $P2Y_{12}$ receptor include but are not limited to the activities described in the Examples discussed below. Accordingly, the amino acid sequence can often be altered, for example to render the peptide more hydrophobic or hydrophilic, without adversely affecting the biological activities of the protein.

Ordinarily, the allelic variants, the conservative substitution variants, and the members of the protein family, will have an amino acid sequence having at least about 75% amino acid sequence identity with the sequence set forth in SEQ ID NO: 2, SEQ ID NO: 4, SEQ ID NO: 6 or SEQ ID NO: 12 more preferably at least about 80%, even more preferably at least about 90%, and most preferably at least about 95% sequence identity to said sequences. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. A further discussion of the methods of determining sequence identity is provided below. Fusion proteins, or N-terminal, C-terminal or internal extensions, deletions, or insertions into the peptide sequence shall not be construed as affecting homology.

Contemplated variants further include those containing predetermined mutations by, e.g., homologous recombination, site-directed or PCR mutagenesis, and the corresponding proteins of other animal species, including but not limited to canine, rabbit, mouse, porcine, bovine, ovine, equine and non-human primate species, and the alleles or other naturally occurring variants of the family of proteins; and derivatives wherein the protein has been covalently modified by substitution, chemical, enzymatic, or other appropriate means with a moiety other than a naturally occurring amino acid (for example a detectable moiety such as an enzyme or radioisotope).

The proteins of the present invention also include molecules having a portion of the amino acid sequence disclosed in SEQ ID NO: 2, SEQ ID NO: 4, SEQ ID NO: 6 or SEQ ID NO: 12 such as fragments having a consecutive sequence of at least about 3, 4, 5, 6, 10, 15, 20, 25, 30, 35 or more amino acid residues of the protein. Such fragments, also referred to as peptides or polypeptides, may contain antigenic regions, functional regions of the protein identified as regions of the amino acid sequence which correspond to known protein domains, as well as regions of pronounced hydrophilicity. The regions are all easily identifiable by using commonly available protein sequence analysis software such as MacVector™ (Oxford Molecular).

As described below, members of the family of proteins can be used: 1) to identify agents which modulate at least one activity of the $P2Y_{12}$ protein; 2) to identify binding partners for the protein, 3) as an antigen to raise polyclonal or monoclonal antibodies, and 4) as a therapeutic agent or target.

B. Nucleic Acid Molecules

The present invention further provides and utilizes nucleic acid molecules that encode the proteins having SEQ ID NO: 2, SEQ ID NO: 4, SEQ ID NO: 6 or SEQ ID NO: 12 and the related proteins herein described, preferably in isolated form. As used herein, "nucleic acid" is defined as RNA or DNA that encodes a protein or peptide as defined above, is complementary to a nucleic acid sequence encoding such peptides, hybridizes to such a nucleic acid and remains stably bound to it under appropriate stringency conditions, or encodes a polypeptide sharing at least about 75% sequence identity, preferably at least about 80%, and more preferably at least about 85% sequence identity with the peptide sequences of the invention. Specifically contemplated are genomic DNA, cDNA, mRNA and antisense molecules, as well as nucleic acids based on alternative backbones or including alternative bases whether derived from natural sources or synthesized. Such hybridizing or complementary nucleic acids, however, are defined further as being novel and non-obvious over any prior art nucleic acid.

Homology or identity at the nucleotide or amino acid sequence level is determined by BLAST (Basic Local Alignment Search Tool) analysis using the algorithm employed by the programs blastp, blastn, blastx, tblastn and tblastx (Karlin et al. *Proceedings of the National Academy of Science USA*, Vol. 87 (1990) pp. 2264–2268 and Altschul, S F. *Journal of Molecular Evolution*, Vol. 36 (1993) pp. 290–300, herein incorporated by reference in their entirety) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al. (*Nature Genetics*, Vol. 6 (1994) pp. 119–129) which is herein incorporated by reference in its entirety. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al. *Proceedings of the National Academy of Science USA*, Vol. 89 (1992) pp. 10915–10919, herein incorporated by reference in its entirety). For blastn, the scoring matrix is set by the ratios of M (i.e., the reward score for a pair of matching residues) to N (i.e., the penalty score for mismatching residues), wherein the default values for M and N are 5 and −4, respectively.

"Stringent conditions" are those that (1) employ low ionic strength and high temperature for washing, for example, 0.015 M NaCl/0.0015 M sodium titrate/0.1% SDS at 50 C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42 C. Another example is use of 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42 C., with washes at 42 C. in 0.2×SSC and 0.1% SDS. As used herein, highly stringent conditions include the use of a wash at 65° C. using 0.1×SSC and 0.1% SDS (see Sambrook et al.). A skilled artisan can readily determine and vary the stringency conditions appropriately to obtain a clear and detectable hybridization signal. Preferred molecules are those that hybridize under the above conditions to the complement of SEQ ID NO: 1, SEQ ID NO: 3, SEQ ID NO: 5 or SEQ ID NO: 11 and which encode a functional protein. Preferred hybridizing molecules are those that hybridize under the above conditions to the complement strand of the open reading frame of SEQ ID NO:1 (nucleotides 130–1158), SEQ ID NO: 3 (nucleotides 163–1107), SEQ ID NO: 5 (nucleotides 73–1098) or SEQ ID NO: 11 (nucleotides 73–873).

As used herein, a clear signal is typically produced by hybridizing or annealing two nucleic acid molecules such that their complements exhibit at least about 80%, preferably at least about 85%, preferably at least about 90%, preferably at least about 95%, preferably at least about 96%, preferably at least about 97%, preferably at least about 98% or most preferably at least about 99% identity at the nucleotide level.

As used herein, a nucleic acid molecule is said to be "isolated" when the nucleic acid molecule is substantially separated from contaminant nucleic acid molecules encoding other polypeptides.

The present invention further provides fragments of the encoding nucleic acid molecule. As used herein, a fragment of an encoding nucleic acid molecule refers to a small portion of the entire protein coding sequence. The size of the fragment will be determined by the intended use. For example, if the fragment is chosen so as to encode an active portion of the protein, the fragment will need to be large enough to encode the functional region(s) of the protein. For instance, fragments which encode peptides corresponding to predicted antigenic regions may be prepared.

If the fragment is to be used as a nucleic acid probe or PCR primer, then the fragment length is chosen so as to obtain a relatively small number of false positives during probing/priming. Fragments of the encoding nucleic acid molecules of the present invention (i.e., synthetic oligonucleotides) that are used as probes or specific primers for the polymerase chain reaction (PCR), or to synthesize gene sequences encoding proteins of the invention can easily be synthesized by chemical techniques, for example, the phosphotriester method of Matteucci et al. (*Journal of the American Chemical Society*, Vol. 103 (1981) pp. 3185–3191) or using automated synthesis methods. In addition, larger DNA segments can readily be prepared by well known methods, such as synthesis of a group of oligonucleotides that define various modular segments of the gene, followed by ligation of oligonucleotides to build the complete modified gene.

The encoding nucleic acid molecules of the present invention may further be modified so as to contain a detectable label for diagnostic and probe purposes. A variety of such labels are known in the art and can readily be employed with the encoding molecules herein described. Suitable labels include, but are not limited to, biotin, radiolabeled nucleotides and the like. A skilled artisan can readily employ any such labels to obtain labeled variants of the nucleic acid molecules of the invention.

Modifications to the primary structure itself by deletion, addition, or alteration of the amino acids incorporated into the protein sequence during translation can be made without destroying the activity of the protein. Such substitutions or other alterations result in proteins having an amino acid sequence encoded by a nucleic acid falling within the contemplated scope of the present invention.

C. Isolation of Other Related Nucleic Acid Molecules

As described above, the identification and characterization of the $P2Y_{12}$ nucleic acid molecule having SEQ ID NO: 1, SEQ ID NO: 3, SEQ ID NO: 5 or SEQ ID NO: 11 allows a skilled artisan to isolate nucleic acid molecules that encode other members of the protein family in addition to the sequences herein described.

Briefly, a skilled artisan can readily use the amino acid sequence of SEQ ID NO: 2, SEQ ID NO: 4, SEQ ID NO: 6 or SEQ ID NO: 12 to generate antibody probes to screen expression libraries prepared from appropriate cells. Typically, polyclonal antiserum from mammals such as rabbits immunized with the purified protein (as described below) or monoclonal antibodies can be used to probe a mammalian cDNA or genomic expression library, such as lambda gt11 library, to obtain the appropriate coding sequence for other members of the protein family. The cloned cDNA sequence can be expressed as a fusion protein, expressed directly using its own control sequences, or expressed by constructions using control sequences appropriate to the particular host used for expression of the enzyme.

Alternatively, a portion of the coding sequence herein described can be synthesized and used as a probe to retrieve DNA encoding a member of the protein family from any mammalian organism. Oligomers containing approximately 18–20 nucleotides (encoding about a 6–7 amino acid stretch) are prepared and used to screen genomic DNA or cDNA libraries to obtain hybridization under stringent conditions or conditions of sufficient stringency to eliminate an undue level of false positives.

In PCR based methods, pairs of oligonucleotide primers can be prepared for use in a polymerase chain reaction (PCR) to selectively clone an encoding nucleic acid molecule. A PCR denature/anneal/extend cycle for using such PCR primers is well known in the art and can readily be adapted for use in isolating other encoding nucleic acid molecules.

Lastly, nucleic acid molecules encoding other members of the protein family may also be identified in existing genomic or other sequence information using any available computational method, including but not limited to: PSI-BLAST (Altschul, et al. (1997) Nucleic Acids Res. 25:3389–3402); PHI-BLAST (Zhang, et al. (1998), Nucleic Acids Res. 26:3986–3990), 3D-PSSM Kelly et al. (2000) J. Mol. Biol. 299(2): 499–520); and other computational analysis methods (Shi et al. (1999) Biochem. Biophys. Res. Commun. 262(1):132–8 and Matsunami et. al. (2000) Nature 404 (6778):601–4.

D. rDNA Molecules Containing a Nucleic Acid Molecule

The present invention further provides and utilizes recombinant DNA molecules (rDNAs) that contain a coding sequence. As used herein, a rDNA molecule is a DNA molecule that has been subjected to molecular manipulation in situ. Methods for generating rDNA molecules are well known in the art, for example, see Sambrook et al. *Molecular Cloning: A Laboratory Manual.* Cold Spring Harbor, N.Y. Cold Spring Harbor Laboratory Press, 1985. In the preferred rDNA molecules, a coding DNA sequence is operably linked to expression control sequences and/or vector sequences.

The choice of vector and/or expression control sequences to which one of the protein family encoding sequences of the present invention is operably linked depends directly, as is well known in the art, on the functional properties desired, e.g., protein expression, and the host cell to be transformed. A vector contemplated by the present invention is at least capable of directing the replication or insertion into the host chromosome, and preferably also expression, of the structural gene included in the rDNA molecule.

Expression control elements that are used for regulating the expression of an operably linked protein encoding sequence are known in the art and include, but are not limited to, inducible promoters, constitutive promoters, secretion signals, and other regulatory elements. Preferably, the inducible promoter is readily controlled, such as being responsive to a nutrient in the host cell's medium.

In one embodiment, the vector containing a coding nucleic acid molecule will include a prokaryotic replicon, i.e., a DNA sequence having the ability to direct autonomous replication and maintenance of the recombinant DNA molecule extra-chromosomally in a prokaryotic host cell, such as a bacterial host cell, transformed therewith. Such replicons are well known in the art. In addition, vectors that include a prokaryotic replicon may also include a gene whose expression confers a detectable marker such as a drug resistance. Typical bacterial drug resistance genes are those that confer resistance to ampicillin or tetracycline.

Vectors that include a prokaryotic replicon can further include a prokaryotic or bacteriophage promoter capable of directing the expression (transcription and translation) of the coding gene sequences in a bacterial host cell, such as E. coli. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from BioRad Laboratories, (Richmond, Calif.), pPL and pKK223 available from Pharmacia (Piscataway, N.J.).

Expression vectors compatible with eukaryotic cells, preferably those compatible with vertebrate cells such as kidney cells, can also be used to form rDNA molecules that contain a coding sequence. Eukaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), the vector pCDM8 described herein, and the like eukaryotic expression vectors.

Eukaryotic cell expression vectors used to construct the rDNA molecules of the present invention may further include a selectable marker that is effective in an eukaryotic cell, preferably a drug resistance selection marker. A preferred drug resistance marker is the gene whose expression results in neomycin resistance, i.e., the neomycin phosphotransferase (neo) gene. (Southern et al. *Journal of Molecular and Applied Genetics*, Vol. 1, no. 4 (1982) pp. 327–341) Alternatively, the selectable marker can be present on a separate plasmid, and the two vectors are introduced by co-transfection of the host cell, and selected by culturing in the appropriate drug for the selectable marker.

E. Host Cells Containing an Exogenously Supplied Coding Nucleic Acid Molecule

The present invention further provides or utilizes host cells transformed with a nucleic acid molecule that encodes a protein of the present invention. The host cell can be either prokaryotic or eukaryotic. Eukaryotic cells useful for expression of a protein of the invention are not limited, so long as the cell line is compatible with cell culture methods and compatible with the propagation of the expression vector and expression of the gene product. Preferred eukaryotic host cells include, but are not limited to, yeast, insect and mammalian cells, preferably vertebrate cells such as those from a mouse, rat, monkey or human cell line. Preferred eukaryotic host cells include Chinese hamster ovary (CHO) cells available from the ATCC as CCL61, NIH Swiss mouse embryo cells (NIH3T3) available from the ATCC as CRL 1658, baby hamster kidney cells (BHK), COS and COS7 cells and like eukaryotic tissue culture cell lines.

Any prokaryotic host can be used to express a rDNA molecule encoding a protein of the invention, particularly peptides and fragments of the full-length receptor protein. The preferred prokaryotic host is *E. coli*.

Transformation of appropriate cell hosts with a rDNA molecule of the present invention is accomplished by well known methods that typically depend on the type of vector used and host system employed. With regard to transformation of prokaryotic host cells, electroporation and salt treatment methods are typically employed, see, for example, Cohen et al. *Proceedings of the National Academy of Science USA*, Vol. 69, no. 8 (1972) pp. 2110–2114; and Maniatis et al. *Molecular Cloning: A Laboratory Mammal.* Cold Spring Harbor, N.Y. Cold Spring Harbor Laboratory Press, 1982). With regard to transformation of vertebrate cells with vectors containing rDNAs, electroporation, cationic lipid or salt treatment methods are typically employed, see, for example, Graham et al. *Virology*, Vol. 52, no. 2 (1973) pp. 456–467; and Wigler et al. *Proceedings of the National Academy of Science USA*, Vol. 76 (1979) pp. 1373–1376.

Successfully transformed cells, i.e., cells that contain a rDNA molecule of the present invention, can be identified by well known techniques including the selection for a selectable marker. For example, cells resulting from the introduction of an rDNA of the present invention can be cloned to produce single colonies. Cells from those colonies can be harvested, lysed and their DNA content examined for the presence of the rDNA using a method such as that described by Southern, *Journal of Molecular Biology*, Vol. 98, no. 3 (1975) pp. 503–517; or Berent et al. *Biotechnic and Histochemistry*, Vol. 3 (1985) pp. 208; or the proteins produced from the cell assayed via an immunological method.

F. Production of Recombinant Proteins Using a rDNA Molecule

The present invention further provides or utilizes methods for producing a protein of the invention using nucleic acid molecules herein described. In general terms, the production of a recombinant form of a protein typically involves the following steps:

First, a nucleic acid molecule is obtained that encodes a protein of the invention, such as the nucleic acid molecule depicted in SEQ ID NO: 1, nucleotides 130–1158 of SEQ ID NO: 1, nucleotides 130–1161 of SEQ ID NO: 1, SEQ ID NO: 3, nucleotides 163–1107 of SEQ ID NO:3, SEQ ID NO: 5, nucleotides 73–1098 of SEQ ID NO: 5, nucleotides 73–1101 of SEQ ID NO: 5, SEQ ID NO: 11, nucleotides 73–873 of SEQ ID NO: 11 or nucleotides 73–876 of SEQ ID NO: 11. If the encoding sequence is uninterrupted by introns as are SEQ ID NO: 1, SEQ ID NO: 3, SEQ ID NO: 5 or SEQ ID NO: 11, it is directly suitable for expression in any host.

The nucleic acid molecule is then preferably placed in operable linkage with suitable control sequences, as described above, to form an expression unit containing the protein open reading frame. The expression unit is used to transform a suitable host and the transformed host is cultured under conditions that allow the production of the recombinant protein. Optionally the recombinant protein is isolated from the medium or from the cells; recovery and purification of the protein may not be necessary in instances where some impurities may be tolerated, particularly when membrane fragments containing the receptor polypeptide are desired.

Each of the foregoing steps can be done in a variety of ways. For example, the desired coding sequences may be obtained from genomic fragments and used directly in appropriate hosts. The construction of expression vectors that are operable in a variety of hosts is accomplished using appropriate replicons and control sequences, as set forth above. The control sequences, expression vectors, and transformation methods are dependent on the type of host cell used to express the gene and were discussed in detail earlier. Suitable restriction sites can, if not normally available, be added to the ends of the coding sequence so as to provide an excisable gene to insert into these vectors. A skilled artisan can readily adapt any host/expression system known in the art for use with the nucleic acid molecules of the invention to produce recombinant protein.

G. Methods to Identify Binding Partners

Another embodiment of the present invention provides methods for isolating and identifying binding partners of proteins of the invention In one method of the invention, a $P2Y_{12}$ protein, or fragment thereof, is mixed with a potential binding partner or an extract or fraction of a cell under conditions that allow the association of potential binding partners with the protein of the invention. After mixing, peptides, polypeptides, proteins or other molecules that have become associated with a protein of the invention are separated from the mixture. The binding partner that bound to the protein of the invention can then be removed and further analyzed. To identify and isolate a binding partner, the entire protein, for instance a protein comprising the entire amino acid sequence of SEQ ID NO: 2, SEQ ID NO: 4, SEQ ID NO: 6 or SEQ ID NO: 12 can be used. Alternatively, a fragment of the protein can be used.

As used herein, a cellular extract refers to a preparation or fraction which is made from a lysed or disrupted cell, for instance, from platelets. The preferred source of cellular extracts will be cells that normally express the receptor polypeptide.

A variety of methods can be used to obtain an extract of a cell. Cells can be disrupted using either physical or chemical disruption methods. Examples of physical disruption methods include, but are not limited to, sonication and mechanical shearing. Examples of chemical lysis methods include, but are not limited to, detergent lysis and enzyme lysis. A skilled artisan can readily adapt methods for preparing cellular extracts in order to obtain extracts for use in the present methods.

Once an extract of a cell is prepared, the extract is mixed with the protein of the invention under conditions in which association of the protein with the binding partner can occur. A variety of conditions can be used, the most preferred being conditions that closely resemble conditions found in the cytoplasm of a human cell. Features such as osmolarity, pH, temperature, and the concentration of cellular extract used, can be varied to optimize the association of the protein with the binding partner.

After mixing under appropriate conditions, the bound complex is separated from the mixture. A variety of techniques can be utilized to separate the mixture. For example, antibodies specific to a protein of the invention can be used to immunoprecipitate the binding partner complex. Alternatively, standard chemical separation techniques such as chromatography and density/sediment centrifugation can be used.

After removal of non-associated cellular constituents found in the extract, the binding partner can be dissociated from the complex using conventional methods. For example, dissociation can be accomplished by altering the salt concentration or pH of the mixture.

To aid in separating associated binding partner pairs from the mixed extract, the protein of the invention can be immobilized on a solid support. For example, the protein can be attached to a nitrocellulose matrix or acrylic beads. Attachment of the protein to a solid support aids in separating peptide/binding partner pairs from other constituents found in the extract. The identified binding partners can be either a single protein or a complex made up of two or more proteins. Alternatively, binding partners may be identified using a Far-Western assay according to the procedures of Takayama et al. *Methods in Molecular Biology,* Vol. 69 (1997) pp. 171–184 or identified through the use of epitope tagged proteins or GST fusion proteins.

Alternatively, the nucleic acid molecules of the invention can be used in a yeast two-hybrid system. The yeast two-hybrid system has been used to identify other protein partner pairs and can readily be adapted to employ the nucleic acid molecules herein described.

H. Radioligand Binding Assays

Expression of the human $P2Y_{12}$ receptor in mammalian cells allows for preparation of cell membranes to be utilized in high throughput screening assays (e.g., radioligand binding assays or other assays). Any standard procedure or assay format may be used such as those below described. The use of cell membranes eliminates the requirement of using platelets and/or blood products as a source of receptor for these assays, which improves the overall efficiency and convenience for the user.

I. Methods to Identify Agents that Modulate the Expression of the Nucleic Acids

Another embodiment of the present invention provides methods for identifying agents that modulate the expression of a nucleic acid encoding a protein of the invention such as a protein having the amino acid sequence of SEQ ID NO: 2, SEQ ID NO: 4, SEQ ID NO: 6 or SEQ ID NO: 12. Such assays may utilize any available means of monitoring for changes in the expression level of the nucleic acids of the invention. As used herein, an agent is said to modulate the expression of a nucleic acid of the invention, for instance a nucleic acid encoding the protein having the sequence of SEQ ID NO: 2, SEQ ID NO: 4, SEQ ID NO: 6 or SEQ ID NO: 12, if it is capable of up- or down-regulating expression of the nucleic acid in a cell compared to a control.

In one assay format, cell lines that contain reporter gene fusions between the 3' and/or 5' regulatory sequences +/− the open reading frame defined by nucleotides 130–1158 of SEQ ID NO: 1 or nucleotides 130–1161 of SEQ ID NO: 1 or nucleotides 163–1107 of SEQ ID NO: 3 or nucleotides 73–1098 of SEQ ID NO: 5 or nucleotides 73–1101 of SEQ ID NO: 5 or nucleotides 73–873 of SEQ ID NO: 11 or nucleotides 73–876 of SEQ ID NO: 11 and any assayable fusion partner may be prepared. Numerous assayable fusion partners are known and readily available including the firefly luciferase gene and the gene encoding chloramphenicol acetyltransferase (Alam et al. *Analytical Biochemistry,* Vol. 188 (1990) pp. 245–254). Cell lines containing the reporter gene fusions are then exposed to the agent to be tested under appropriate conditions and time. Differential expression of the reporter gene between samples exposed to the agent and control samples identifies agents which modulate the expression of a nucleic acid encoding the protein having the sequence of SEQ ID NO: 2, SEQ ID NO: 4, SEQ ID NO: 6 or SEQ ID NO: 12.

Additional assay formats may be used to monitor the ability of the agent to modulate the expression of a nucleic acid encoding a protein of the invention such as the protein having SEQ ID NO: 2, SEQ ID NO: 4, SEQ ID NO: 6 or SEQ ID NO: 12. For instance, mRNA expression may be monitored directly by hybridization to the nucleic acids of the invention. Cell lines are exposed to the agent to be tested under appropriate conditions and time and total RNA or mRNA is isolated by standard procedures such as those disclosed in Sambrook et al. *Molecular Cloning: A Laboratory Manual.* Cold Spring Harbor, N.Y. Cold Spring Harbor Laboratory Press, 1985.

Probes to detect differences in RNA expression levels between cells exposed to the agent and control cells may be prepared from the nucleic acids of the invention. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarily which should exist between two nucleic acid strands in order to form a hybrid. Stringency should be chosen to maximize the difference in stability between the probe:target hybrid and potential probe:non-target hybrids.

Probes may be designed from the nucleic acids of the invention through methods known in the art. For instance, the G+C content of the probe and the probe length can affect probe binding to its target sequence. Methods to optimize probe specificity are commonly available in Sambrook et al. (*Molecular Cloning. A Laboratory Manual.* Cold Spring Harbor, N.Y. Cold Spring Harbor Laboratory Press, 1985); or Ausubel et al (*Current Protocols in Molecular Biology.* N.Y., Greene Publishing Company, 1995).

Hybridization conditions are modified using known methods, such as those described by Sambrook et al. and Ausubel et al. as required for each probe. Hybridization of total cellular RNA or RNA enriched for polyA RNA can be accomplished in any available format. For instance, total cellular RNA or RNA enriched for polyA RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a porous glass wafer. The glass wafer can then be exposed to total cellular RNA or polyA RNA from a sample under conditions in which the affixed sequences will specifically hybridize. Such glass wafers and hybridization methods are widely available, for example, those disclosed by Beattie (WO 95/11755). By examining for the ability of a given probe to specifically hybridize to an RNA sample from an untreated cell population and from a cell population exposed to the agent, agents which up or down regulate the expression of a nucleic acid encoding the protein having the sequence of SEQ ID NO: 2, SEQ ID NO: 4, SEQ ID NO: 6 or SEQ ID NO: 12 are identified.

Hybridization for qualitative and quantitative analysis of mRNAs may also be carried out by using a RNase Protection Assay (i.e., RPA, see Ma et al. *Methods,* Vol. 10, no. 3 (1996) pp. 273–238). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes, pH 6.4, 0.4 M NaCl and 1 mM EDTA. The resulting hybrids are then digested in a buffer comprising 40 g/ml ribonuclease A and 2 g/ml ribonuclease. After deactivation and extraction of extraneous proteins, the samples are loaded onto urea/polyacrylamide gels for analysis.

In another assay format, cells or cell lines are first be identified which express the gene products of the invention physiologically (e.g., see for example, FIGS. 10 and 12 for tissue distribution via Northern blot). Cell and/or cell lines so identified would be expected to comprise the necessary cellular machinery such that the fidelity of modulation of the transcriptional apparatus is maintained with regard to exogenous contact of agent with appropriate surface transduction mechanisms and/or the cytosolic cascades. Further, such cells or cell lines would be transduced or transfected with an expression vehicle (e.g., a plasmid or viral vector) construct comprising an operable non-translated 5'-promoter containing end of the structural gene encoding the instant gene products fused to one or more antigenic fragments, which are peculiar to the instant gene products, wherein said fragments are under the transcriptional control of said promoter and are expressed as polypeptides whose molecular weight can be distinguished from the naturally occurring polypeptides or may further comprise an immunologically distinct tag. Such a process is well known in the art (see Maniatis et al. *Molecular Cloning: A Laboratory Mammal.* Cold Spring Harbor, N.Y. Cold Spring Harbor Laboratory Press, 1982).

Cells or cell lines transduced or transfected as outlined above would then be contacted with agents under appropriate conditions; for example, the agent comprises a pharmaceutically acceptable excipient and is contacted with cells comprised in an aqueous physiological buffer such as phosphate buffered saline (PBS) at physiological pH, Eagles balanced salt solution (BSS) at physiological pH, PBS or BSS comprising serum or conditioned media comprising PBS or BSS and/or serum incubated at 37° C. Said conditions may be modulated as deemed necessary by one of skill in the art. Subsequent to contacting the cells with the agent, said cells will be disrupted and the polypeptides from disrupted cells are fractionated such that a polypeptide fraction is pooled and contacted with an antibody to be further processed by immunological assay (e.g., ELISA, immunoprecipitation or Western blot). The pool of proteins isolated from the "agent contacted" sample will be compared with a control sample where only the excipient is contacted with the cells and an increase or decrease in the immunologically generated signal from the "agent contacted" sample compared to the control will be used to distinguish the effectiveness of the agent.

J. Methods to Identify Agents that Modulate at Least One Activity of the Proteins.

Another embodiment of the present invention provides methods for identifying agents that modulate at least one activity of a protein of the invention such as the protein having the amino acid sequence of SEQ ID NO: 2, SEQ ID NO: 4, SEQ ID NO: 6 or SEQ ID NO: 12. Such methods or assays may utilize any means of monitoring or detecting the desired activity.

In one format, the relative amounts of a protein of the invention between a cell population that has been exposed to the agent to be tested compared to an un-exposed control cell population may be assayed. In this format, probes such as specific antibodies are used to monitor the differential expression of the protein in the different cell populations. Cell lines or populations are exposed to the agent to be tested under appropriate conditions and time. Cellular lysates or membrane fractions may be prepared from the exposed cell line or population and a control, unexposed cell line or population. The cellular lysates or membrane fractions are then analyzed with the probe.

Antibody probes are prepared by immunizing suitable mammalian hosts in appropriate immunization protocols using the peptides, polypeptides or proteins of the invention if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co. (Rockford, Ill.), may be desirable to provide accessibility to the hapten. The hapten peptides can be extended at either the amino or carboxy terminus with a Cysteine residue or interspersed with cysteine residues, for example, to facilitate linking to a carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein (*Nature*, Vol. 256, no. 5517 (August 1975) pp. 495–497) or modifications which effect immortalization of lymphocytes or spleen cells, as is generally known. The immortalized cell lines secreting the desired antibodies are screened by immunoassay in which the antigen is the peptide hapten, polypeptide or protein. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Antibody regions that bind specifically to the desired regions of the protein can also be produced in the context of chimeras with multiple species origin, particularly humanized antibodies.

As mentioned above, isolated cells providing a P2Y$_{12}$ receptor polypeptide on their surface and the availability of the recombinant DNA encoding a receptor polypeptide which permits display and expression of the receptor on host cell surfaces are all valuable tools for evaluating the ability of candidate agonists or antagonists to bind to the receptor and thus contribute to the receptor's activation or deactivation. In this manner, the invention includes cell assay systems which utilize an isolated or a recombinantly produced receptor polypeptide to screen for agonist and antagonist activity of candidate drugs. These assays are especially useful in assuring that these candidate therapeutic agents have the desired effect of either activating or inhibiting the receptor polypeptide. Determination of these properties is essential in evaluating the specificity of drugs intended for binding other related receptors.

The most useful host cells are typically animal cells, including mammalian cells. In order to be useful in the assays, the cells must have intracellular mechanisms which permit the receptor to be displayed on the cell surface. Particularly useful cells for use in the method of the invention are *Xenopus laevis* frog oocytes, which typically utilize cRNA rather than standard recombinant expression systems proceeding from the DNA encoding the desired protein. Capped RNA (at the 5' end) is typically produced from linearized vectors containing DNA sequences encoding the receptor. The reaction is conducted using RNA polymerase and standard reagents. cRNA is recovered, typically using phenol/chloroform precipitation with ethanol and injected into the oocytes.

The animal host cells expressing the DNA encoding the receptor or the cRNA-injected oocytes are then cultured to effect the expression of the encoding nucleic acids so as to produce the receptor display on the cell surface. These cells then are used directly in assays for assessment of a candidate drug to bind, antagonize, or activate the receptor.

One method of evaluating candidates as potential therapeutic agents typically involves a binding assay in which the candidate (such as a peptide or a small organic molecule) would be tested to measure if, or to what extent, it binds the receptor. Preferably, a mammalian or insect cell line that expresses the receptor or plasma membrane preparations thereof, will be used in a binding assay. For example, a candidate antagonist competes for binding to the receptor with either a labeled nucleotide agonist or antagonist. Varying concentrations of the candidate are supplied, along with a constant concentration of the labeled agonist or antagonist. The inhibition of binding of the labeled material can then be measured using established techniques. This measurement is then correlated to determine the amount and potency of the candidate that is bound to the receptor.

Another method of evaluating candidates for potential therapeutic applications typically involves a functional assay in which the candidate's effect upon cells expressing the recombinant receptor is measured, rather than simply determining its ability to bind the receptor (see Jantzen et al. (1999) *Thromb. Haemost.* 81:111–117). Suitable functional assays include those that measure calcium mobilization, $^{45}$Ca efflux or measurements of intracellular Ca+2 concentration with fluorescent dyes such as fura-2 and voltage clamp, described below.

For example, agonist-induced increases in $^{45}$Ca release by oocytes expressing cRNA encoding the receptor or other mammalian recombinant cells producing the receptor can be measured by the techniques described by Williams, et al., (1988) *Proc. Natl. Acad. Sci. USA* 85:4939–4943. Intracellular calcium pools are labeled by incubating groups of 30 oocytes in 300 µl calcium-free modified Barth's solution (MBSH) containing 50 mu Ci $^{45}$CaCl$_2$ (10–40 mCi/mg Ca; Amersham) for 4 hours at room temperature. The labeled oocytes or cells are washed, then incubated in MBSH II without antibiotics for 90 minutes. Groups of 5 oocytes are selected and placed in individual wells in a 24-well tissue culture plate containing 0.5 ml/well MBSH II without antibiotics. This medium is removed and replaced with fresh medium every 10 minutes; the harvested medium is analyzed by scintillation counting to determine $^{45}$Ca released by the oocytes during each 10-minute incubation. The 10-minute incubations are continued until a stable baseline of $^{45}$Ca release per unit time is achieved. Two additional 10-minute collections are obtained, then test medium including agonist is added and $^{45}$Ca release determined.

Using the above assay, the ability of a candidate drug to activate the receptor can be tested directly. In this case, ADP or the agonists of the invention are used as controls. In addition, by using the agonists of the invention to activate the recombinant receptor, the effect of the candidate drug on this activation can be tested directly. Cells expressing the nucleic acids encoding the receptor are incubated in the assay in the presence of agonist with and without the candidate compound. A diminution in activation in the presence of the candidate will indicate an antagonist effect. Conversely, the ability of a candidate drug to reverse the antagonist effects of an antagonist of the invention may also be tested.

As indicated above, receptor activation can also be measured by means of the two-electrode voltage clamp assay. In this assay, agonist-induced inward chloride currents are measured in voltage-clamped oocytes that express the receptor coinjected with a chimeric G alpha subunit which converts Gi-responses to Gq responses. The technique suitable for use in the instant invention is described by Julius, et al., (1988) *Science* 241:558–563.

Agents that are assayed in the above method can be randomly selected or rationally selected or designed. As used herein, an agent is said to be randomly selected when the agent is chosen randomly without considering the specific sequences involved in the association of a protein of the invention alone or with its associated substrates, binding partners, etc. An example of randomly selected agents is the use a chemical library or a peptide combinatorial library, or a growth broth of an organism.

As used herein, an agent is said to be rationally selected or designed when the agent is chosen on a nonrandom basis which takes into account the sequence of the target site and/or its conformation in connection with the agent's action.

The agents of the present invention can be, as examples, peptides, small molecules, vitamin derivatives, as well as carbohydrates. A skilled artisan can readily recognize that there is no limit as to the structural nature of the agents of the present invention. Dominant negative proteins, DNAs encoding these proteins, antibodies to these proteins, peptide fragments of these proteins or mimics of these proteins may be introduced into cells to affect function. "Mimic" used herein refers to the modification of a region or several regions of a peptide molecule to provide a structure chemically different from the parent peptide but topographically and functionally similar to the parent peptide (see Grant G A. in: Meyers (ed.) *Molecular Biology and Biotechnology* (New York, VCH Publishers, 1995), pp. 659–664).

The peptide agents of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Another class of agents of the present invention are antibodies immunoreactive with critical positions of proteins of the invention. Antibody agents are obtained by immunization of suitable mammalian subjects with peptides, containing as antigenic regions, those portions of the protein intended to be targeted by the antibodies.

K. cAMP Assays

Expression of the P2Y$_{12}$ receptor in mammalian cells allows for measurement of ADP-dependent cAMP responses in transfected cells. This functional read-out is useful for high throughput screening using standard screening assay techniques. In addition, the demonstrated coupling to the cAMP pathway is useful for screening assays using other G-protein dependent read-outs, such as changes in intracellular calcium mediated by Gα16 or Gi-Gq-chimeric subunits. (see FIGS. 3A, B, C).

L. Uses for Agents that Modulate at Least One Activity of the Proteins.

As provided in the Examples, the proteins and nucleic acids of the invention, such as the proteins having the amino acid sequences of SEQ ID NO: 2, SEQ ID NO: 4, SEQ ID NO: 6 or SEQ ID NO: 12, are expressed in various tissues, including but not limited to the brain, and blood cells such as platelets. Agents that modulate, up-or-down-regulate the expression of the protein or agents such as agonists or antagonists of at least one activity of the protein may be used to modulate biological and pathologic processes associated with the protein's function and activity.

Agonists or antagonists of the invention have therapeutic utility (1) in treating diseases caused by aberrant activation of this receptor in tissues where it is customarily found, for example in the vascular system or the brain and (2) in treating diseases whose symptoms can be ameliorated by stimulating or inhibiting the activity of the receptor, for example diseases of the vascular system or injured vascular tissue.

Vascular disease may refer to any disease of the cardiovascular system, including but not limited to acute myocardial infarction, unstable angina, chronic stable angina, transient ischemic attacks, strokes, peripheral vascular disease, preeclampsia, deep venous thrombosis, embolism, disseminated intravascular coagulation or thrombotic cytopenic purpura. Vascular injury may refer to an injury arising by any means, including but not limited to procedures such as angioplasty, carotid endarterectomy, post CABG (coronary artery bypass graft) surgery, vascular graft surgery, stent placements or insertion of endovascular devices and prostheses.

As used herein, a subject can be any mammal, so long as the mammal is in need of modulation of a pathological or biological process mediated by a protein of the invention. The term mammal is defined as an individual belonging to the class Mammalia. The invention is particularly useful in the treatment of human subjects.

Pathological processes refer to a category of biological processes which produce a deleterious effect. For example, expression of a protein of the invention may be associated with improved ADP-induced platelet activation and aggregation. As used herein, an agent is said to modulate a pathological process when the agent reduces the degree or severity of the process. For instance, bleeding disorders or thrombosis may be prevented or disease progression modulated by the administration of agents which modulates in some way the expression or at least one activity of a protein of the invention.

The agents of the present invention can be provided alone, or in combination with other agents that modulate a particular pathological process. For example, an agent of the present invention can be administered in combination with other known drugs or may be combined with surgery or with known blood-thinning drugs. As used herein, two agents are said to be administered in combination when the two agents are administered simultaneously or are administered independently in a fashion such that the agents will act at the same time.

The agents of the present invention can be administered via parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The present invention further provides compositions containing one or more agents which modulate expression or at least one activity of a protein of the invention. While individual needs vary, determination of optimal ranges of effective amounts of each component is within the skill of the art. Typical dosages comprise 0.1 to 100 µg/kg body wt. The preferred dosages comprise 0.1 to 10 µg/kg body weight. The most preferred dosages comprise 0.1 to 1 µg/kg body weight.

In addition to the pharmacologically active agent, the compositions of the present invention may contain suitable pharmaceutically acceptable carriers comprising excipients and auxiliaries which facilitate processing of the active compounds into preparations which can be used pharmaceutically for delivery to the site of action. Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers. Liposomes can also be used to encapsulate the agent for delivery into the cell.

The pharmaceutical formulation for systemic administration according to the invention may be formulated for enteral, parenteral or topical administration. Indeed, all three types of formulations may be used simultaneously to achieve systemic administration of the active ingredient.

Suitable formulations for oral administration include hard or soft gelatin capsules, pills, tablets, including coated tablets, elixirs, suspensions, syrups or inhalations and controlled release forms thereof.

In practicing the methods of this invention, the compounds of this invention may be used alone or in combination, or in combination with other therapeutic or diagnostic agents. In certain preferred embodiments, the compounds of this invention may be coadministered along with other compounds typically prescribed for these conditions according to generally accepted medical practice. The compounds of this invention can be utilized in vivo, ordinarily in mammals, such as humans, sheep, horses, cattle, pigs, dogs, cats, rats and mice, or in vitro.

M. Transgenic Animals

Transgenic animals containing, unmodified, mutant, knock-out or modified genes corresponding to the nucleic acid molecules of the invention, particularly the cDNA sequence of SEQ ID NO: 1, SEQ ID NO: 3, SEQ ID NO: 5 or SEQ ID NO: 11, are also included in the invention. Transgenic animals are genetically modified animals into which recombinant, exogenous or cloned genetic material has been experimentally transferred. Such genetic material is often referred to as a "transgene". The nucleic acid sequence of the transgene, in this case a form of SEQ ID NO: 1, SEQ ID NO: 3, SEQ ID NO: 5 or SEQ ID NO: 11 may be integrated either at a locus of a genome where that particular nucleic acid sequence is not otherwise normally found or at the normal locus for the transgene. The transgene may consist of nucleic acid sequences derived from the genome of the same species or of a different species than the species of the target animal.

The term "germ cell line transgenic animal" refers to a transgenic animal in which the genetic alteration or genetic information was introduced into a germ line cell, thereby conferring the ability of the transgenic animal to transfer the genetic information to offspring. If such offspring in fact possess some or all of that alteration or genetic information, then they too are transgenic animals.

The alteration or genetic information may be foreign to the species of animal to which the recipient belongs, foreign only to the particular individual recipient, or may be genetic information already possessed by the recipient. In the last case, the altered or introduced gene may be expressed differently than the native gene.

Transgenic animals can be produced by a variety of different methods including transfection, electroporation, microinjection, gene targeting in embryonic stem cells and recombinant viral and retroviral infection (see, e.g., U.S. Pat. No. 4,736,866; U.S. Pat. No. 5,602,307; Mullins et al. *Hypertension* (1993) 22(4):630–633; Brenin et al. *Surgical Oncology*, Vol. 6, no. 2 (1997) pp. 99–110; "Recombinant Gene Expression Protocols" in: Tuan (ed.), *Methods in Molecular Biology*, No. 62 (Humana Press, 1997)).

A number of recombinant or transgenic mice have been produced, including those which express an activated oncogene sequence (U.S. Pat. No. 4,736,866); express simian SV40 T-antigen (U.S. Pat. No. 5,728,915); lack the expression of interferon regulatory factor 1 (IRF-1) (U.S. Pat. No. 5,731,490); exhibit dopaminergic dysfunction (U.S. Pat. No. 5,723,719); express at least one human gene which participates in blood pressure control (U.S. Pat. No. 5,731,489); display greater similarity to the conditions existing in naturally occurring Alzheimer's disease (U.S. Pat. No. 5,720, 936); have a reduced capacity to mediate cellular adhesion (U.S. Pat. No. 5,602,307); possess a bovine growth hormone gene (Clutter et al. *Genetics*, Vol. 143, no. 4 (1996) pp. 1753–1760); or, are capable of generating a fully human antibody response (McCarthy. *The Lancet*, Vol. 349, no. 9049 (1997) pp. 405).

While mice and rats remain the animals of choice for most transgenic experimentation, in some instances it is preferable or even necessary to use alternative animal species. Transgenic procedures have been successfully utilized in a variety of non-murine animals, including sheep, goats, pigs, dogs, cats, monkeys, chimpanzees, hamsters, rabbits, cows and guinea pigs (see, e.g., Kim et al. *Molecular Reproduction and Development*, Vol. 46, no. 4 (1997) pp. 515–526; Houdebine. *Reproduction, Nutrition, Development*, Vol. 35, no. 6 (1995) pp. 609–617; Petters *Reproduction, Fertility and Development*, Vol. 6, no. 5 (1994) pp. 643–645; Schnieke et al. *Science* Vol. 278, no. 5346 (1997) pp. 2130–2133; and Amoah, *Journal of Animal Science*, Vol. 75, no. 2 (1997) pp. 578–585.

The method of introduction of nucleic acid fragments into recombination competent mammalian cells can be by any method which favors co-transformation of multiple nucleic acid molecules. Detailed procedures for producing transgenic animals are readily available to one skilled in the art, including the disclosures in U.S. Pat. No. 5,489,743 and U.S. Pat. No. 5,602,307.

N. Diagnostic Methods

One means of diagnosing a vascular disease or disorder using the nucleic acid molecules or proteins of the invention involves obtaining a tissue or blood sample from living subjects.

The use of molecular biological tools has become routine in forensic technology. For example, nucleic acid probes may be used to determine the expression of a nucleic acid molecule comprising all or at least part of the sequence of SEQ ID NO: 1, SEQ ID NO: 3, SEQ ID NO: 5 or SEQ ID NO: 11 in forensic/pathology specimens. Further, nucleic acid assays may be carried out by any means of conducting a transcriptional profiling analysis. In addition to nucleic acid analysis, forensic methods of the invention may target the protein encoded by SEQ ID NO: 1, SEQ ID NO: 3, SEQ ID NO: 5 or SEQ ID NO: 11 to determine up or down regulation of the genes (Shiverick et al., *Biochim Biophys Acta* (1975) 393(1):124–33).

Assays to detect nucleic acid or protein molecules of the invention may be in any available format. Typical assays for nucleic acid molecules include hybridization or PCR based formats. Typical assays for the detection of proteins, polypeptides or peptides of the invention include the use of antibody probes in any available format such as in situ binding assays, etc. See Harlow et al., Antibodies: A Laboratory Manual, Cold Spring Harbor Laboratory, 1988. In preferred embodiments, assays are carried-out with appropriate controls. Methods of the invention may involve treatment of tissues with collagenases or other proteases to make the tissue amenable to cell lysis (Semenov et al, *Biull Eksp Biol Med* (1987) 104(7):113–6).

The above methods may also be used in other diagnostic protocols including for forensic purposes, and in diagnostic protocols and methods to detect disease states in other tissues or organs, for example the brain.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Platelet cDNA Library

In the parent provisional application No. 60/171,622, the $P2Y_{12}$ receptor protein was referred to as the H11 receptor. Poly-$A^+$ mRNA from rat platelets was used to generate a directional oligo-dT primed cDNA library in the pcDNA3.1$^+$ vector. Approximately 320,000 clones were divided into 48 individual pools. Linearized cDNA templates from these pools were transcribed in vitro using T7 RNA polymerase (Ambion). Sib selection of a positive pool was performed to subfractionate the signal to the level of 96 clones. All were sequenced and a novel GPCR was further characterized. Rat $P2Y_{12}$ cDNA was used to isolate a human orthologue from a platelet λ ZAP cDNA library. A full length $hP2Y_{12}$ cDNA expression construct was obtained by ligation of a λ clone and a fragment derived by 3' RACE into the pcIneo expression vector (Promega). GenBank accession number for human $P2Y_{12}$ is AF3 13449. SEQ ID NO:1 corresponds to a full length rat $P2Y_{12}$ sequence, SEQ ID NO:3 corresponds to a partial human $P2Y_{12}$ sequence, SEQ ID NO:5 corresponds to a full length human $P2Y_{12}$ sequence, SEQ ID NO:11 corresponds to a truncated allelic variant human $P2Y_{12}$ sequence.

Platelet RT-PCR

Whole blood (30 ml) was lysed and total RNA isolated using TriReagent BD (Molecular Research Center). First-strand cDNA was generated (Superscript 2, Life Technologies) and PCR (35 cycles) performed using the following mRNA-specific primers: The $P2Y_{12}$ 5' (5'-CCAGAATCAACAGTTATCAGGTAACC-3') (SEQ ID NO: 7); and 3'(5'GTCAGTTAATATTTTTACTTAGCGCTTTGC-3') (SEQ ID NO: 8) primers were annealed at 57° C., while the GPIIb 5' (5'-GTCAACGGGGATGGGAGGCATGA-3') (SEQ ID NO: 9) and 3'(5'-GTCTGCCTCATCTCGAAGGAAGG-3') (SEQ ID NO: 10) primers were annealed at 60° C. PCR products were analyzed by electrophoresis in 1% agarose and bands of the correct size were isolated for direct sequencing.

Electrophysiology

Defolliculated *Xenopus laevis* oocytes were injected with a positive 500 clone pool (10 ng), $rP2Y_{12}$ (10 pg), $hP2Y_{12}$ (50 pg), Kir3.1, Kir3.4, PTX and hm2 (1 ng each) cRNAs as indicated. Three to seven days after injection, two-electrode voltage-clamp recordings were performed using a Geneclamp 500 amplifier (Axon Instruments) and a Maclab A/D converter (Maclab). Membrane potentials were clamped at −70 mV while the recording chamber was perfused at a rate of 2 ml/min with a solution containing (in mM) 70 KCl, 20 NaCl, 3 $MgCl_2$, 5 HEPES, pH 7.4, at room temperature. The KCl was replaced with NaCl to examine responses in zero potassium. Agonists and antagonists (Roche Molecular Biochemistry or Sigma) were diluted in the recording solution. Experiments using C1330–7 included 0.1% dimethylsulfoxide to enhance its solubility in the perfusate.

Generation of Stable Mammalian Cell Lines and cAMP Assays

Chinese Hamster Ovary (CHO) cells or rat 2–9 fibroblasts, which are null for $G_i$-linked purinergic receptors, were transfected with $hP2Y_{12}$ or $rP2Y_{12}$ cDNA's, respectively using FuGene reagent (Roche), and cells were cultured in the presence of G418 for 2 weeks to select for stable transfectants. For cAMP assays, stably transfected CHO cells expressing the $hP2Y_{12}$ plasmid were plated in 12-well dishes. Forty-eight hours later media was removed from the cells and replaced with serum-free media containing IBMX (0.25 mM final) and incubated at 37° C. for 5 minutes. Cells were incubated for an additional 5 min with 10 μM forskolin, as well as the indicated agonists and antagonists. Pertussis toxin treatment (30 ng/ml) occurred for 20 hrs at 37° C. prior to assay. Cyclic AMP levels were determined from aliquots of cell extracts in a radioimmunoassay (Amersham Biotrak cAMP $^{125}$I assay system).

Northern and in situ Hybridizations

Northern blots of poly-$A^+$ RNA from human tissues (Clontech) or total human platelet RNA was hybridized with radiolabeled $hP2Y_{12}$ cDNA fragments under standard conditions. Digoxigenin-labeled in situ hybridization was performed on coronal rat brain sections using an RNA probe corresponding to the antisense sequence of $rP2Y_{12}$ (Caterina et al. (1997).

Flow Cytometry

Adult male Sprague-Dawley rats were anesthetized and whole blood isolated using citrate as anticoagulant. Platelet-rich plasma (PRP) was isolated by centrifugation and used for flow-cytometry analysis. A rabbit anti-sera (SynPep Corporation) was produced to the amino-terminal 23 residues of $rP2Y_{12}$. IgG was purified using protein-G sepharose. Rat PRP ($2 \times 10^6$ cells) and cultured rat 2–9 fibroblasts transfected with $rP2Y_{12}$ cDNA ($1 \times 10^5$ cells) were incubated with purified IgG (10–50 μg/ml) in FACS buffer (phosphate-buffered saline containing 0.1% BSA and 2% heat-inactivated fetal bovine serum) in a total volume of 100 ul for 1 hr at 4° C. Cells and platelets were then washed with cold FACS buffer and incubated with 2.5 ug/ml of FITC-conjugated goat anti-rabbit antibody for 30 min at 4° C. Cells and platelets were washed, resuspended in cold FACS buffer, and fluorescence of cell-bound secondary antibody was determined with a FACSort flow cytometer (Becton-Dickinson). Control samples contained cells without antibodies (for determination of autofluorescence), cells with control rabbit IgG, or secondary antibodies alone.

FIG. 1: $P2Y_{12}$ is a G Protein-Coupled Receptor that Responds to ADP

FIG. 1(A). Activation of potassium-dependent currents in *Xenopus* oocytes expressing $P2Y_{12}$ with Kir3.1 and 3.4. ADP (10 μM) was applied (short bars) in the presence or absence (long bar) of extracellular potassium (70 mM) while recording membrane currents in the whole-cell voltage clamp configuration. Oocytes injected with mRNA for Kir3.1 and 3.4 alone (top trace) do not exhibit significant currents in response to ADP application unless messages from a positive cDNA pool, the isolated rat $P2Y_{12}$ cRNA or the human $P2Y_{12}$ homologue are included (subsequent traces). (B) ADP-selective stimulation of potassium channel-dependent currents by $P2Y_{12}$ occurs via a pertussis toxin-sensitive pathway. UDP, adenosine (A), ATP-α-S or ADP (10 μM each) were sequentially applied to oocytes expressing the rat or human receptor with or without Kir3.1, 3.4 and pertussis toxin (PTX). (C) The agonist profile of $P2Y_{12}$ recapitulates that observed for the $G_i$-coupled platelet ADP receptor. Concentration-response curves for ADP and 2MeSADP are presented. Membrane currents were normalized in each oocyte to a response obtained with 10 μM ADP. Each point represents the mean values (+/−s.d.) from five independent oocytes. The Hill equation was used to fit the response data.

FIG. 2: Currents Stimulated by ADP in Oocytes Expressing $hP2Y_{12}$ with Kir3.1 and 3.4 are Inhibited by 2MeSAMP, C1330-7 and a Thiol Reagent FIG. 2(A). Current tracing showing reversible block of ADP (1 μM) responses by 2MeSAMP (10 μM) and C1330-7 (1 μM), but not A3P5P (300 μM). The dot (.) indicates the start of a 15 sec application of ADP, while bars denote co-application with the antagonist. (B) 2MeSAMP and C1330-7 inhibition curves. Current responses were normalized to that elicited by ADP (500 nM) alone in each oocyte and plotted as the mean+/−s.d. Curves were fitted to the data using the Hill equation (n=5 independent oocytes for each point). (C) Selective ablation of $P2Y_{12}$ but not m2 muscarinic receptor signaling by the thiol reagent pCMBS. ADP (10 μM), carbachol (1 μM), and pCMBS (1 mM) were applied sequentially to an oocyte expressing both receptors concurrently with Kir3.1 and 3.4. Bars indicate periods of drug application (10 sec).

FIG. 3: Activation of $hP2Y_{12}$ in CHO Cells Inhibits Adenylyl Cyclase

Figure 3A:
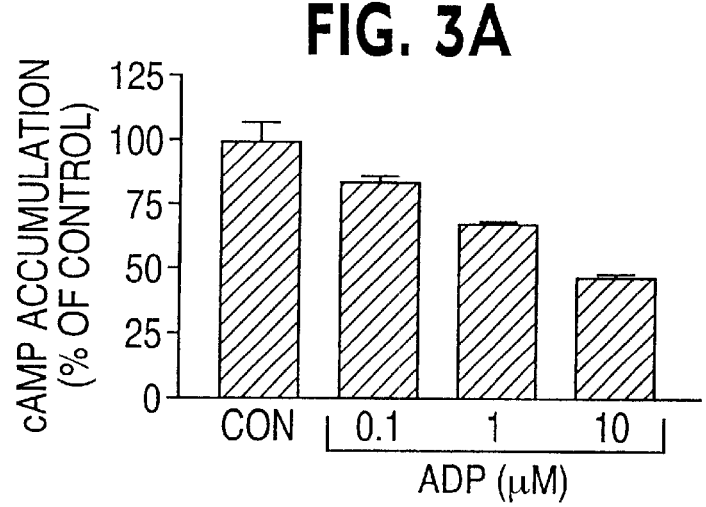
FIGS. 3A–3C Activation of hP2Y$_{12}$ in CHO cells inhibits adenylyl cyclase.
Figure 3B:
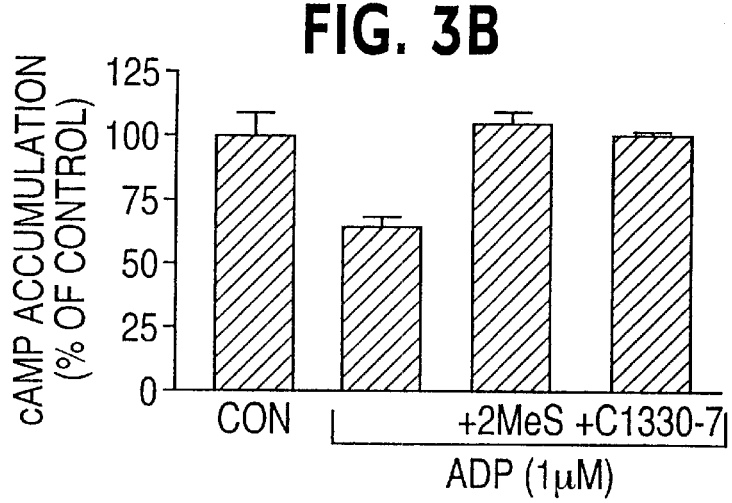
Figure 3C:
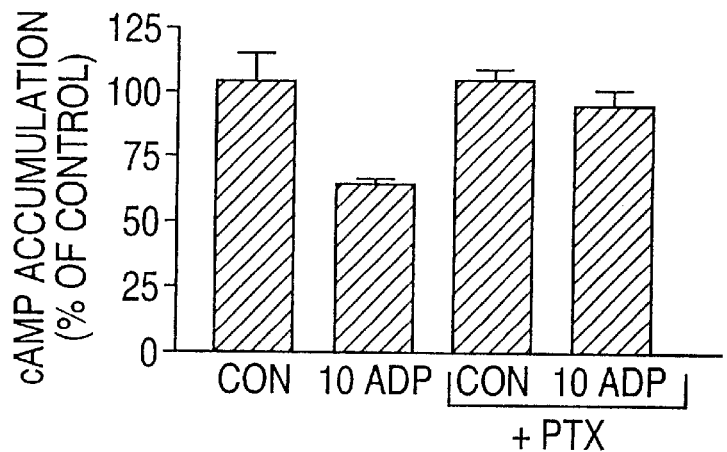

FIG. 3(A). Receptor coupling to adenylyl cyclase was assessed as ADP-mediated (0.1–10 μM) inhibition of forskolin-stimulated (10 μM) cAMP accumulation (CON=control, normalized to 100%). (B) The effect of the specific antagonists 2MeSAMP (2-MES)(50 μM) and C1330-7 (50 μM) on repression of ADP-mediated (1 μM) forskolin-stimulated cAMP levels. (C) Effect of pertussis toxin (PTX) pretreatment on the inhibition by 10 μM ADP of forskolin-stimulated cAMP levels. Results are the mean+/−s.d. of three representative experiments performed in triplicate.

FIG. 4: $P2Y_{12}$ Receptor is Selectively Expressed in Platelets and Brain

FIGS. 4(A, B). Northern analysis of $hP2Y_{12}$ transcripts. All lanes contain 2 μg poly-$A^+$ mRNA except samples from platelet and Jurkat cells (20 μg each). (C) $rP2Y_{12}$ transcripts are distributed throughout the brain in presumptive glia. Staining was equally abundant in fiber tracts (corpus callosum, cc) and regions enriched for neuronal cell bodies (dentate gyrus, dg; arcuate nucleus of the hypothalamus, an), but absent from vasculature (pericallosal artery, pa). Control (sense) riboprobes did not stain these regions. Ventricular structures are also indicated (dorsal third ventricle, d3v; third ventricle, 3v). (D) FACS analysis of rat platelets stained with $rP2Y_{12}$ antisera (filled peak) or a control IgG (unfilled peak). (E) FACS analysis of rat 2–9 fibroblasts transfected with the $rP2Y_{12}$ cDNA clone (filled peak) or untransfected rat 2–9 fibroblasts (unfilled peak).

Figure 5A:
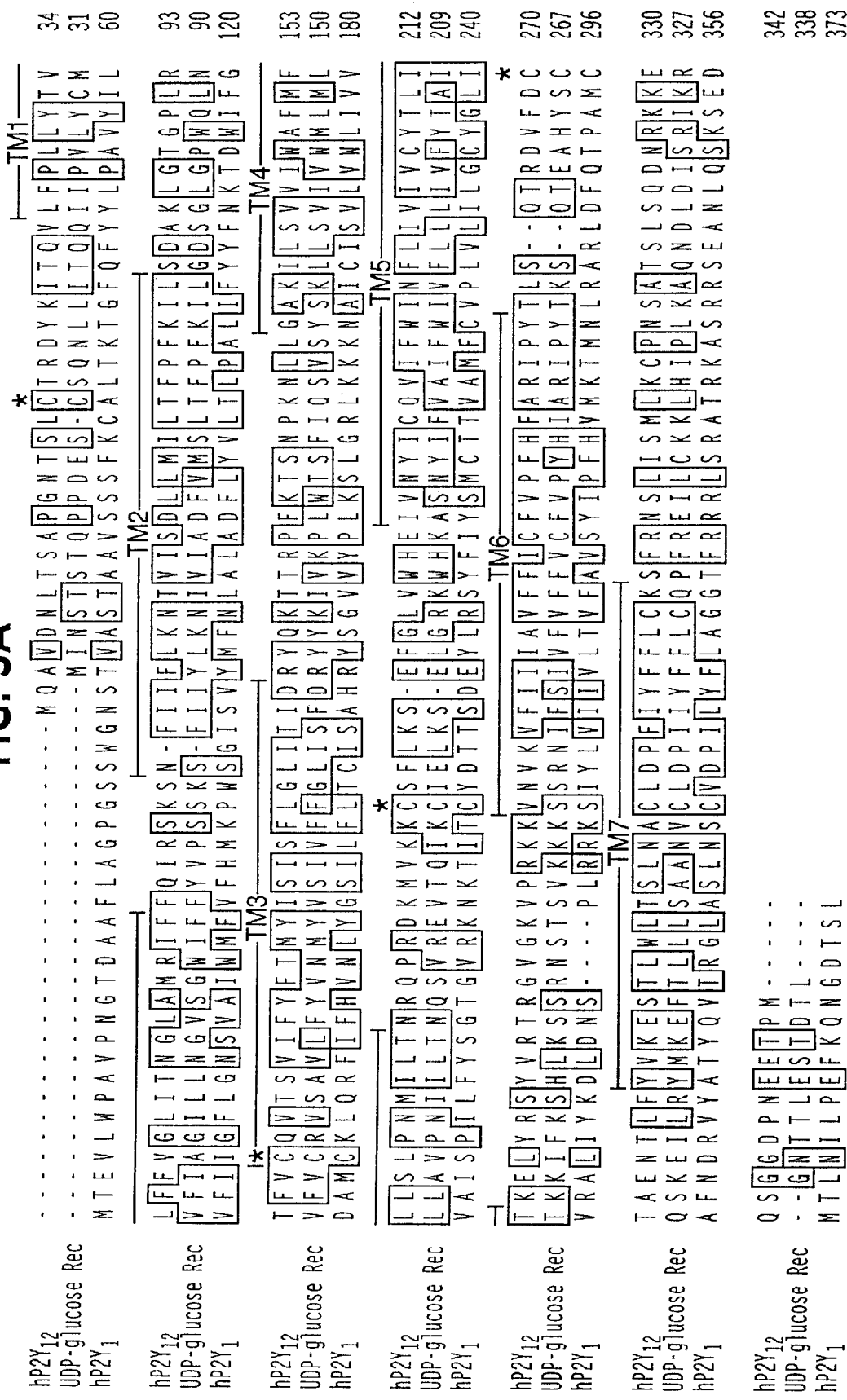

FIG. 5: A Frame-Shift Mutation within the $hP2Y_{12}$ Gene is Associated with a Bleeding Disorder FIG. 5(A). Deduced amino acid sequence of the $hP2Y_{12}$ protein and alignment with other homologous receptor sequences. The putative membrane-spanning domains are designated with bars above the sequence. $hP2Y_{12}$ sequence is aligned with the sequences of $hP2Y_1$ receptor (also expressed in platelets and activated by ADP), as well as with the human UDP-glucose receptor, with which it shares greatest homology. Shading denotes amino acid identity (black) or similarity (gray); asterisks (*) denote extracellular cysteine residues. (B) A P2Y12 allele from a patient (ML) with defective ADP-dependent aggregation contains a 2 base pair deletion, resulting in a frame-shift mutation and a premature truncation of the protein. No such mutation was observed in PCR products amplified and sequenced from genomic DNA of one hundred randomly chosen individuals. (C) Mutant $hP2Y_{12}$ receptor from patient ML is non-functional and does not act in a dominant-negative capacity. Representative ADP-evoked membrane currents from an oocyte injected with 50 pg of wildtype (WT) $hP2Y_{12}$ cRNA (upper left panel), 50 pg of mutant (MT) $hP2Y_{12}$ cRNA (upper right panel) or with 50 pg WT and increasing amounts of MT $hP2Y_{12}$ cRNAs (bottom panels). Ooctyes were also injected with 1 ng Kir3.1 and 1 ng Kir3.4 cRNAs. Dot indicates onset of ADP application (10 μM for 5 s). (D) Patient ML has abnormally low levels of RT-PCR product derived from $P2Y_{12}$ mRNA. RT-PCR using either $P2Y_{12}$-(lanes 1–4) or GPIIb-(lanes 5–8) specific primers was performed using whole blood RNA from patient ML (lanes 1,2,5,6) or a control (CON) sample (lanes 3,4,7,8). PCR reactions performed on RNA samples without reverse transcriptase control for genomic DNA contamination (lanes 1,3,5,7). A 1.1 kb product encoding the $P2Y_{12}$ ORF was amplified from the control sample, but virtually absent from ML (a faint product can be observed upon longer exposure). In contrast, the amount of product (0.77 kb) amplified from GPIIb mRNA was equivalent between ML and control. Sequence analysis reveals that ML's $P2Y_{12}$ RT-PCR product derived solely from the mutant allele.

Figure 6A:
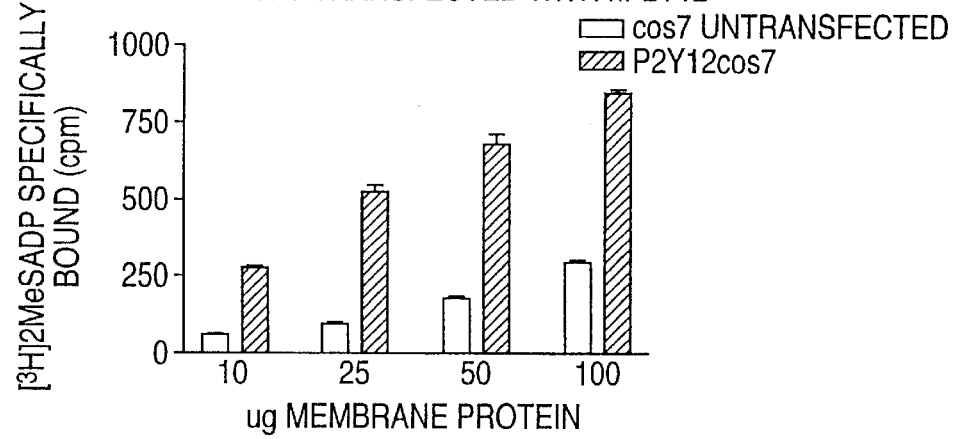
FIGS. 6A–6B Evaluation of [$^3$H]2MeSADP binding to the cloned hP2Y$_{12}$ Receptor.
Figure 6B:
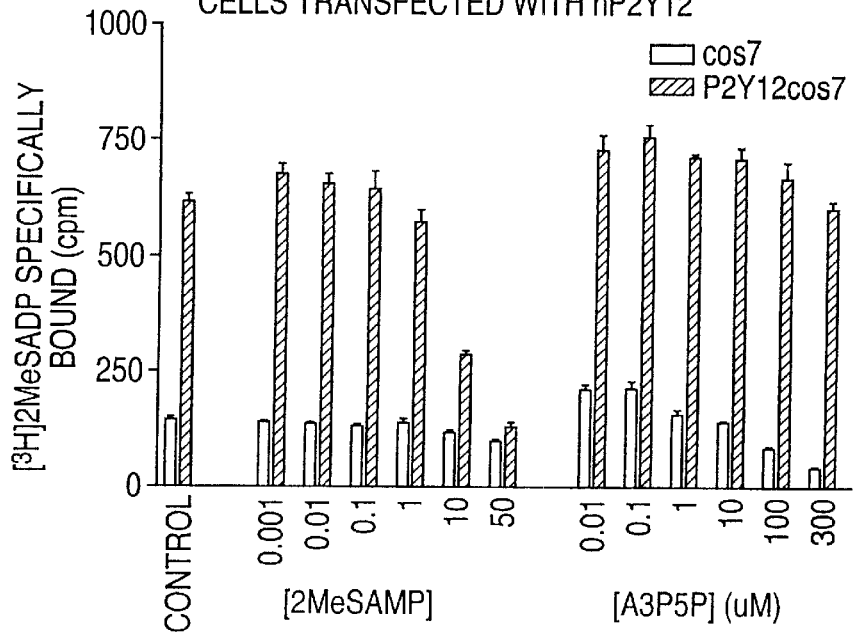
Figure 7:
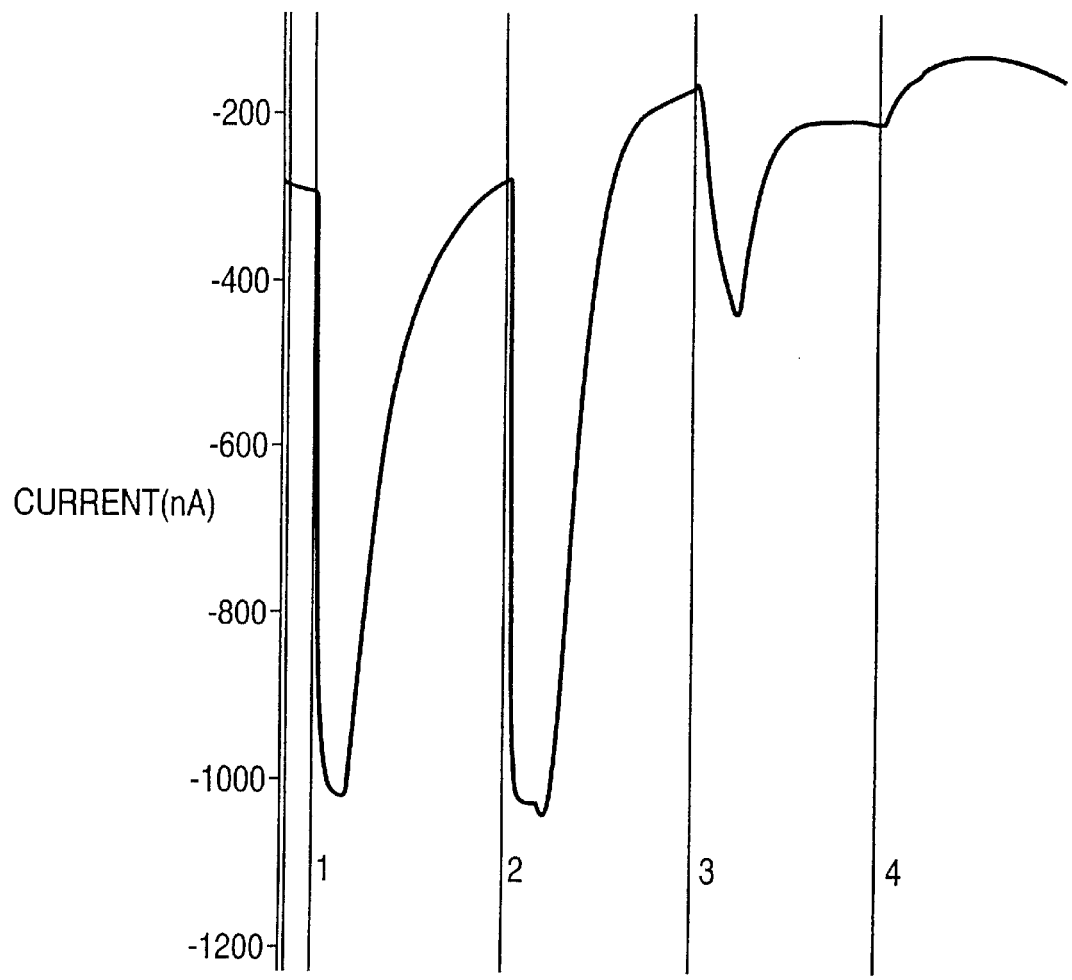
FIG. 7 Representative potassium currents from voltage clamp assays on *Xenopus oocytes*. Oocytes were co-injected with cRNA for the P2Y$_{12}$ receptor and for GIRK1 and GIRK4 potassium channels, cultured for 48–72 hours, and challenged with different agonists and antagonists FIG. 8 Representative potassium currents from voltage clamp assays on *Xenopus oocytes*. Oocytes were co-injected with cRNA for the P2Y$_{12}$ receptor, for pertussis toxin, and for GIRK1 and GIRK4 potassium channels, cultured for 48–72 hours, and challenged with the agonist ADP.

FIG. 6: Evaluation of [$^3$H]2MeSADP Binding to the Cloned hP2Y12 Receptor; High Throughput Screening (HTS) Assay hP2Y12 cDNA was transiently transfected into cos7 cells and crude membranes were prepared using standard procedures. Binding of 1 nM [$^3$H]2MeSADP at various membrane protein concentrations and in the absence and presence of various inhibitors was determined at 4 C. for 30 minutes in a rapid filtration assay (triplicates). Non-specific binding was determined with 10 uM 2MeSADP and subtracted from all data. Each experiment included membranes from untransfected cells.

At 1 nM [$^3$H]2MeSADP (approx. $K_D$ in whole platelet binding assays), specific binding was increased up to 5-fold in membranes from transfected vs. untransfected cells. This ratio was optimal around 25 ug membrane protein, an amount used in many GPCR binding assays. Nonspecific binding (incl. counter background) was <10% of total binding and identical in transfected and untransfected cells. Similar results were obtained with membranes from TSA-201 cells (data not shown). This result indicates that a HTS assay using the cloned P2Y$_{12}$ receptor and available radioligands such as [$^3$H]2MeSADP might be feasible, especially when the receptor expression can be increased another 2-fold and assay conditions will be further optimized. SPA technology should be evaluated to facilitate automation. The amount of membranes required could be further reduced using [$^{33}$P]2MeSADP with higher specific activity.

The selectivity of the expressed receptor was assessed using competition binding with the P2Y$_{12}$ antagonist 2MeSAMP and the P2Y$_1$ antagonist A3P5P. 2MeSAMP at 50 μM reduced [$^3$H]2MeSADP binding to membranes from transfected cells essentially to the level of untransfected cells with a potency similar to whole platelet binding assays. Binding to membranes from untransfected cells was only marginally affected. A3P5P had only little effect on binding even at 300 μM, and the degree of inhibition can be explained by inhibiting endogenous receptors in the untransfected cells. This preliminary experiment suggests that the cloned P2Y$_{12}$ receptor displays a pharmacological profile similar to the high-affinity binding site for [$^3$H]2MeSADP on whole platelets further validating its use for HTS.

To identify the G$_i$-linked platelet ADP receptor, the present inventors engineered Xenopus oocytes to allow detection of G$_i$-linked responses through a sensitive electrophysiological assay. This strategy is based on the fact that several G$_i$-coupled receptors, such as the m2 muscarinic receptor, release Gβγ subunits from heterotrimeric G proteins, thereby activating inwardly rectifying potassium (K$^+$) channels (Kir3.1–4) (Krapivinsky et al. (1995)). A cDNA library from rat platelets was screened in oocytes expressing Kir3.1 and 3.4 and three positive pools that responded to 10 μM ADP (as determined by an increase in K$^+$ current) were identified. Subfractionation of one of these pools led to the identification of a single clone tentatively designated as P2Y$_{12}$ (SEQ ID NO:1). The current induced by ADP was K$^+$-dependent since replacement of K$^+$ in the bath solution resulted in a complete loss of current (FIG. 1A). Additionally, injection of Kir or P2Y$_{12}$ cRNAs alone gave no ADP-dependent currents, indicating that the observed signal was not due to activation of an endogenous purinergic receptor and was Kir-dependent (FIG. 1B). Moreover, when cRNA encoding pertussin toxin was injected together with the rat P2Y$_{12}$ clone, the response to ADP was abolished (FIG. 1B), as predicted for the G$_i$-linked platelet ADP receptor (Ohlmann et al. (1995)). The human P2Y$_{12}$ homolog (SEQ ID NO: 5) was isolated from a human platelet library and similar results were obtained when this cRNA was expressed in Xenopus oocytes (FIGS. 1A, B).

One hallmark of the G$_i$-linked platelet ADP receptor is that substitution of alkylthio groups at the 2-position of the adenine ring increases potency at the receptor (Mills (1996); MacFarlane et al. (1983); Hourani et al. (1994)). Consistent with this, 2MeSADP displayed 2 orders of magnitude greater potency compared to ADP (with an EC50 of 0.9 nM and 300 nM, respectively) (FIG. 1C). In contrast, other nucleoside or nucleotide derivatives were without effect (FIG. 1B). The present inventors also examined the actions of several antagonists specific for the platelet G$_i$-linked ADP receptor. Treatment of Xenopus oocytes expressing the rat or human P2Y$_{12}$ receptor with the nucleotide derivative 2MeSAMP (Jantzen et al. (1999)) or a non-nucleotide inhibitor C1330–7 (Jantzen et al. (1998)), blocked ADP-induced K$^+$ currents with IC50's of 1.4 μM and 40 nM, respectively (FIG. 2B). In contrast, the P2Y$_1$-selective antagonist A3P5P (Boyer et al. (1996)) had no inhibitory effect on the signal evoked by ADP at the rat or human P2Y$_{12}$ (FIG. 2A). Thus, when expressed in Xenopus oocytes, the P2Y$_{12}$ receptor recapitulates the pharmacological profile previously described for the platelet G$_i$-linked ADP receptor. The only anomaly that we observed relates to the action of ATP-αS, which behaved as a weak agonist, rather than an antagonist at the cloned receptor. This finding is somewhat unexpected since ATP derivatives reportedly antagonize the platelet G$_i$-linked receptor. However, this discrepancy may reflect partial degradation or impurities in commercially available preparations of ATP-αS, or differences between the platelet and oocyte environments, such as the degree of ectonucleotidase activity. Indeed, recombinant P2Y$_1$ receptors respond differentially to ATP, depending on the expression system utilized (Palmer et al. (1998); Filippov et al. (2000)).

Chinese Hamster Ovary (CHO) cells expressing the hP2Y$_{12}$ receptor displayed ADP-mediated repression of forskolin-stimulated cAMP levels in a dose-dependent manner, reaching a maximum of 47% reduction at 10 μM ADP (FIG. 3A). The repression of cAMP levels by 1 μM ADP was reversed by the selective antagonists 2MeSAMP and C1330–7 (FIG. 3B), in agreement with the pharmacological profile observed in Xenopus oocytes, and as described for the G$_i$-coupled receptor on platelets. Neither of these antagonists had effects on forskolin-stimulated cAMP levels in the absence of agonist. Similar responses to ADP were observed in rat 2–9 fibroblasts stably expressing rP2Y$_{12}$. Pretreatment of transfected cells with pertussis toxin abolished ADP effects on forskolin-stimulated cAMP (FIG. 3C), suggesting that the response is G$_i$-mediated.

Figure 4C:
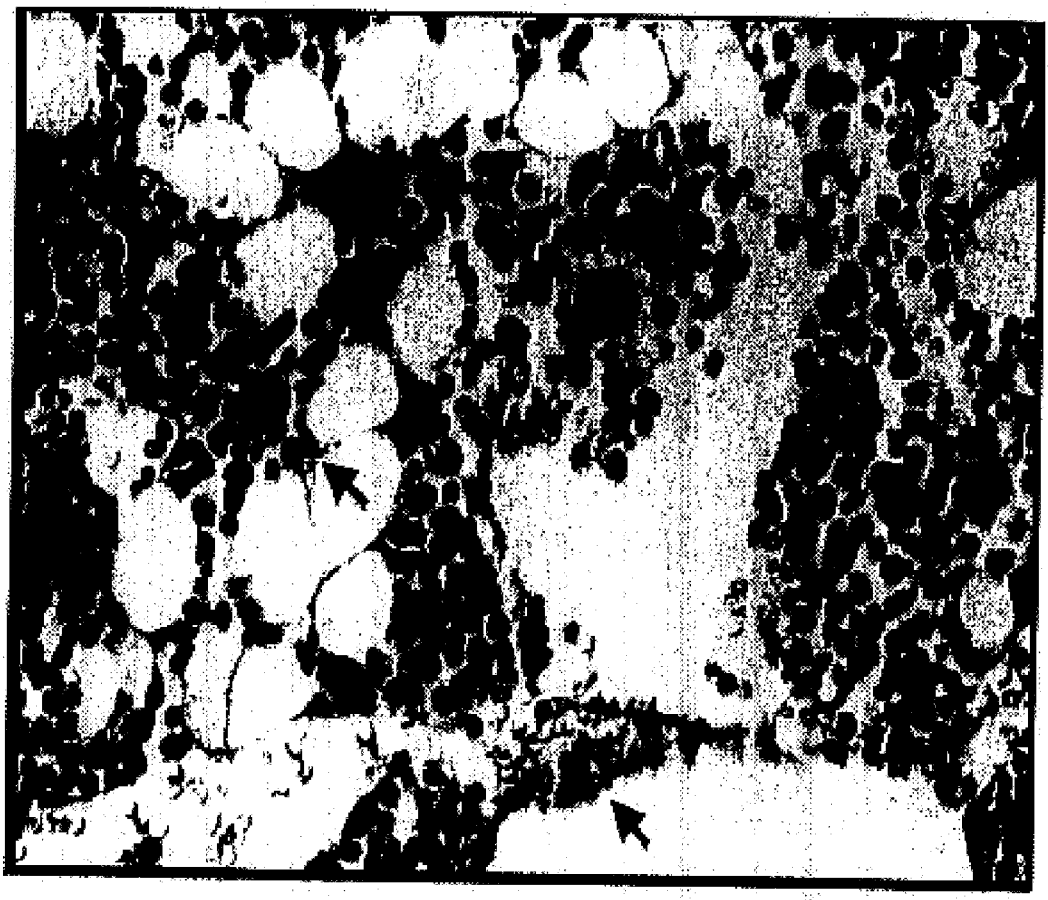

Northern blot analysis demonstrated that P2Y$_{12}$ is abundantly expressed in human platelets, and to a lesser extent in brain (FIGS. 4A, B). The predominant transcript of 2.4 kb was absent from all other tissues examined, including peripheral blood leukocytes. A fainter species of ~4.5 kb was also detected in platelet and brain, while a prominent band of ~1.0 kb (FIG. 4B) was observed only in platelet RNA. Among rat tissues, selective expression in platelets and brain was also seen. Thus, the mRNA for this novel GPCR has a restricted expression pattern and is abundantly present in platelets, consistent with this cDNA encoding the platelet G$_i$-linked receptor. Within the brain, the 2.4 kb species was observed in numerous subregions, including the amygdala, caudate nucleus, corpus collosum, hippocampus, substantia nigra, and thalamus. Cellular resolution of rP2Y$_{12}$ expression was obtained by in situ hybridization histochemistry of brain sections where punctate staining was noted throughout white and gray matter (FIG. 4C). Principal cells of the hippocampus did not stain, nor was a laminar pattern of expression observed in the neocortex. These observations are consistent with a glial expression pattern. Interestingly, the only cell line previously described to express a P2Y purinergic receptor that is negatively coupled to adenylyl cyclase is the rat C6 glioma cell line (Boyer et al. (1993)). Indeed, a 2.4 kb mRNA species was detected in these cells by Northern analysis with a rP2Y$_{12}$ probe.

Using a rabbit polyclonal antisera directed to the predicted amino-terminus of rP2Y$_{12}$, we assessed surface expression of receptor protein on stably-transfected rat 2–9 fibroblasts or rat platelets using flow cytometry. At an antibody concentration of 25 μg/ml, a 9-fold (FIG. 4E) and 4-fold (FIG. 4D) increase in mean fluorescence intensity (compared to a control antibody) was observed with transfected cells and platelets, respectively, demonstrating that P2Y$_{12}$ protein is, indeed, expressed on the platelet surface.

When the chromosomal localization of the P2Y$_{12}$ gene was determined using the Stanford G3 panel (Stewart et al. (1997)) (Research Genetics), P2Y$_{12}$-specific primers mapped closest to STS-D 13626, corresponding to the KIAA0001 gene recently identified as a UDP-glucose GPCR (Chambers et al. (2000)). Both of these genes reside on chromosome 3q24–25, interval D3S1279–1280, a region that also includes the human P2Y$_1$ gene. Thus, this interval contains genes encoding at least three receptors, two of which (P2Y$_1$ and P2Y$_{12}$) mediate ADP-dependent platelet aggregation. Among GPCR's, P2Y$_{12}$ is most closely related to the UDP-glucose receptor (Chambers et al. (2000)) (44% identical) but much less so to P2Y$_1$ (19% identical), suggesting that the UDP-glucose and P2Y$_{12}$ receptors are the product of a relatively recent gene duplication on chromosome 3.

Figure 2C:
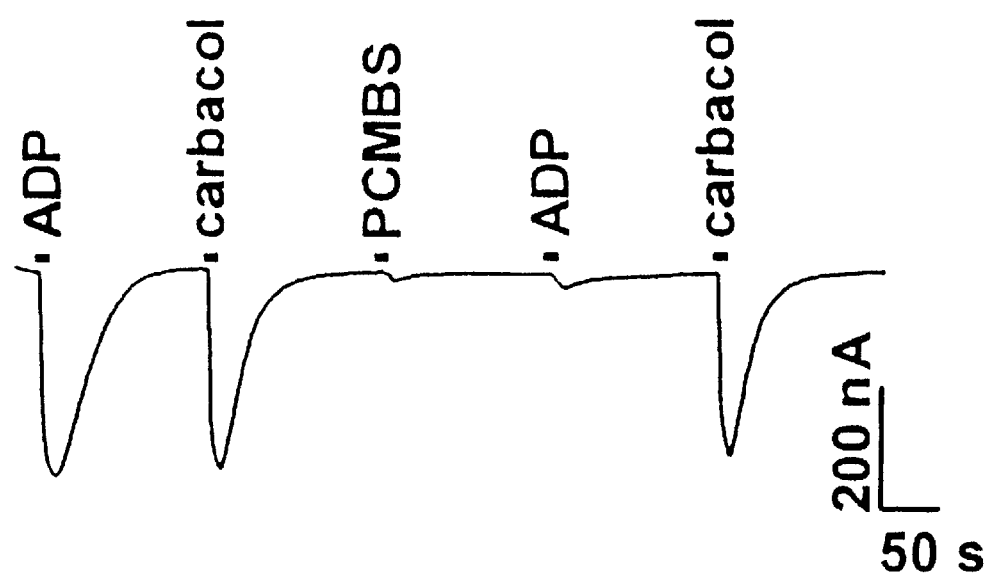

The predicted hP2Y$_{12}$ protein encodes four extracellular cysteines (see FIG. 5). A critical role of cysteine residues in the function of the platelet ADP receptor has been suggested by the ability of thiol reagents to ablate ADP responses in platelets (Mills (1996)). Indeed, the antithrombotic agent clopidogrel is proposed to inactivate the G$_i$-linked platelet ADP receptor through a mechanism in which it is metabolized to a sulphydryl species that modifies a cysteine residue on the receptor (Savi et al. (1999)). The present inventors found that brief exposure of oocytes expressing Kir3.1, 3.4 and hP2Y$_{12}$ to the thiol reagent p-chloromercuriphenylsulfonic acid (pCMBS) eliminated ADP-evoked current responses (FIG. 2C). Inhibition was selective for the P2Y$_{12}$ receptor since activation of this signaling pathway by m2 muscarinic receptors expressed in the same oocytes was unaffected by treatment with pCMBS.

Figure 5C:
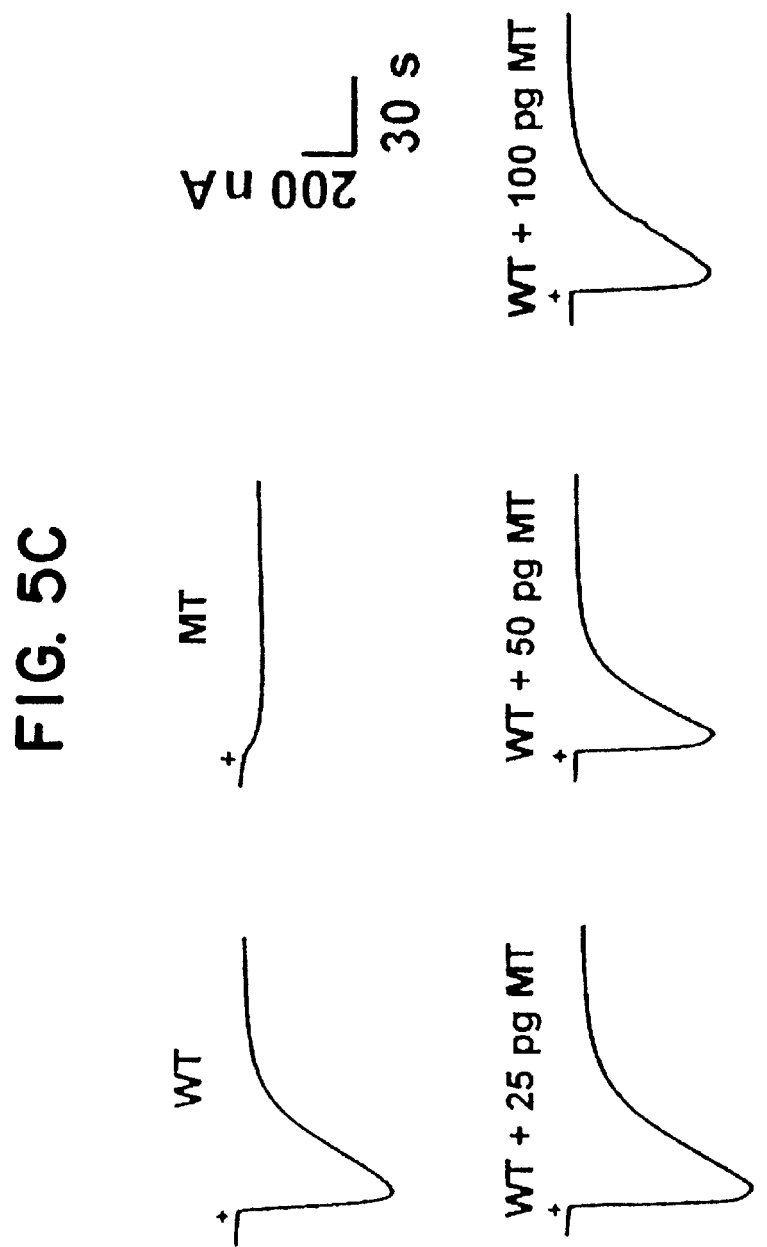
Figure 5D:
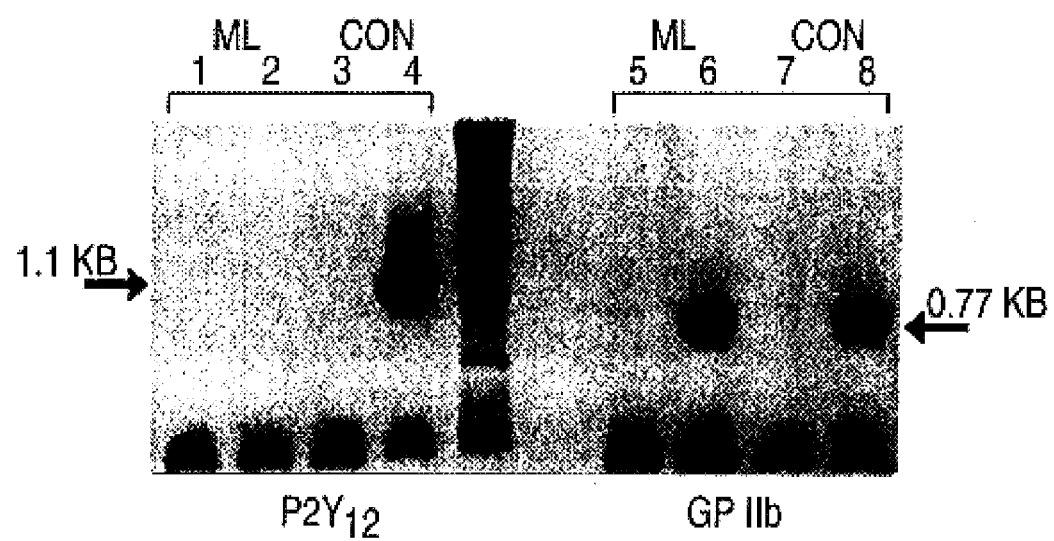

Nurden et al. (1995) have previously described a patient (ML) with a mild bleeding disorder. Platelets from ML exhibit impaired ADP-dependent platelet aggregation, greatly reduced ADP binding activity and lack the ability to inhibit cAMP levels in response to ADP. However, the P2Y$_1$-receptor mediated responses, such as intracellular calcium mobilization and shape change, are not affected, suggesting that this patient has a selective defect in the G$_i$-linked receptor. Analysis of PCR products from the P2Y$_{12}$ coding region from ML's genomic DNA revealed the presence of one mutant allele at this locus, as confirmed by direct sequencing of at least three independent PCR reactions. The mutation found in the P2Y$_{12}$ gene consists of a deletion of two nucleotides (TT<u>CA</u>TT) within the coding region, at amino acid 240 (near the amino-terminal end of TM6), thus shifting the reading frame for 28 residues before introducing a premature stop codon (FIG. 5B). Biochemical studies suggest that platelets from ML lack G$_i$-linked ADP receptors, yet sequence analysis indicates that this individual has one mutant and one wild-type P2Y$_{12}$ allele, at least so far as the protein coding region is concerned. This suggests one of two possibilities: the P2Y$_{12}$ mutation identified exerts a dominant-negative effect, or ML harbors an additional mutation that eliminates expression of the allele containing a wild-type coding region. We evaluated the former possibility using an electrophysiological assay (FIG. 5C). First, no significant activity was observed when oocytes were injected with cRNA transcripts corresponding to the frameshifted allele, demonstrating that this mutant is indeed non-functional. Moreover, when mutant and wild-type cRNA's were co-injected into oocytes at different ratios, no inhibition of the signal from the wild-type allele was observed, demonstrating that the mutant allele does not act in a dominant negative manner. Further support for this conclusion comes from sequence analysis of the P2Y$_{12}$ coding region from ML's daughter, who has previously been shown to have an intermediate number of ADP binding sites and impaired ADP-dependent aggregation (Nurden et al. (1995)). Like her father, she has one wt and one frameshifted allele, and is therefore likely to be a true heterozygote, both genotypically and phenotypically. If so, then the truncated receptor does not act as a dominant negative in vivo. Finally, it was asked whether ML's alleles are both expressed by carrying out RT-PCR analysis with RNA from his platelets. Extremely low levels of P2Y$_{12}$-derived product were obtained compared to levels amplified from an unaffected individual or compared to a control transcript encoding platelet GPIIB (FIG. 5D). In addition, sequence analysis of P2Y$_{12}$ RT-PCR products demonstrated that ML's P2Y$_{12}$ transcripts derive only from the mutant allele (i.e., no wild-type product was detected). We therefore conclude that ML's lack of functional G$_i$-coupled platelet ADP receptor activity is due to the fact that he expresses only the frame-shifted allele.

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

SEQUENCE LISTING

<160> NUMBER OF SEQ ID NOS: 21

<210> SEQ ID NO 1
<211> LENGTH: 1289
<212> TYPE: DNA
<213> ORGANISM: Rattus norvegicus
<220> FEATURE:
<221> NAME/KEY: CDS
<222> LOCATION: (130)..(1158)

<223> OTHER INFORMATION: P2Y12 receptor
<221> NAME/KEY: unsure
<222> LOCATION: (1247)
<223> OTHER INFORMATION: n = a or c or g or t.

<400> SEQUENCE: 1

```
gaattcgagg gctttggcaa cgaaaccaag tcactgagag gaaagcacca gatgccagtc      60
tgcaagttct actaactagt attaccggag acactcattt ccttccgagt caacagaata     120 accaggacc atg gag gtg cct ggt gcc aac gcc acc tca gcc aac acc acc    171
           Met Glu Val Pro Gly Ala Asn Ala Thr Ser Ala Asn Thr Thr
             1               5                  10 tcc att cct ggg acc agc acc ctg tgc agc aga gac tac aag atc acc      219
Ser Ile Pro Gly Thr Ser Thr Leu Cys Ser Arg Asp Tyr Lys Ile Thr
 15              20                  25                  30 cag gtt ctc ttc cca ttg ctc tac act gtc ctg ttt ttt gct ggg ctc      267
Gln Val Leu Phe Pro Leu Leu Tyr Thr Val Leu Phe Phe Ala Gly Leu
                 35                  40                  45 atc acg aac agc ttg gcg atg agg att ttc ttc cag atc cgc agt aaa      315
Ile Thr Asn Ser Leu Ala Met Arg Ile Phe Phe Gln Ile Arg Ser Lys
             50                  55                  60 tcg aac ttc atc att ttt ctt aag aac acg gtc atc tct gat ctt ctt      363
Ser Asn Phe Ile Ile Phe Leu Lys Asn Thr Val Ile Ser Asp Leu Leu
         65                  70                  75 atg atc cta act ttt cct ttc aaa att ctc agt gat gcc aaa ctg gga      411
Met Ile Leu Thr Phe Pro Phe Lys Ile Leu Ser Asp Ala Lys Leu Gly
 80                  85                  90 gct ggg cac ctg aga acc ctg gtg tgc caa gtc act tca gtc acg ttt      459
Ala Gly His Leu Arg Thr Leu Val Cys Gln Val Thr Ser Val Thr Phe
 95                 100                 105                 110 tac ttc aca atg tac atc agt atc tcg ttc ctc gga ttg ata acc att      507
Tyr Phe Thr Met Tyr Ile Ser Ile Ser Phe Leu Gly Leu Ile Thr Ile
                115                 120                 125 gac cga tac ctg aag acc acc aga cca ttt aaa act tcc agc ccc agc      555
Asp Arg Tyr Leu Lys Thr Thr Arg Pro Phe Lys Thr Ser Ser Pro Ser
            130                 135                 140 aat ctt ttg ggt gcg aag att ctt tct gtt gcc atc tgg gcc ttc atg      603
Asn Leu Leu Gly Ala Lys Ile Leu Ser Val Ala Ile Trp Ala Phe Met
        145                 150                 155 ttc ctg ctg tca ctg cct aac atg att ctc acc aac agg agg cca aaa      651
Phe Leu Leu Ser Leu Pro Asn Met Ile Leu Thr Asn Arg Arg Pro Lys
    160                 165                 170 gat aag gac ata acg aaa tgt tct ttc ttg aag tcg gag ttt ggt ctg      699
Asp Lys Asp Ile Thr Lys Cys Ser Phe Leu Lys Ser Glu Phe Gly Leu
175                 180                 185                 190 gtc tgg cac gag ata gtc aat tac atc tgc caa gtc att ttc tgg att      747
Val Trp His Glu Ile Val Asn Tyr Ile Cys Gln Val Ile Phe Trp Ile
                195                 200                 205 aat ttt tta att gtt att gtt tgt tac agc ctc att aca aaa gag ctc      795
Asn Phe Leu Ile Val Ile Val Cys Tyr Ser Leu Ile Thr Lys Glu Leu
            210                 215                 220 tat agg tcc tac gtc aga acg agg ggt tca gcc aaa gct ccc aag aaa      843
Tyr Arg Ser Tyr Val Arg Thr Arg Gly Ser Ala Lys Ala Pro Lys Lys
        225                 230                 235 agg gtg aac atc aag gtt ttc atc atc att gct gtg ttc ttc att tgc      891
Arg Val Asn Ile Lys Val Phe Ile Ile Ile Ala Val Phe Phe Ile Cys
    240                 245                 250 ttc gtt ccc ttc cac ttt gca cgg att ccc tac acc ctg agc cag aca      939
Phe Val Pro Phe His Phe Ala Arg Ile Pro Tyr Thr Leu Ser Gln Thr
255                 260                 265                 270
```

```
cgg gcc gtc ttt gac tgc aat gcc gag aac act ctg ttc tac gtg aag      987
Arg Ala Val Phe Asp Cys Asn Ala Glu Asn Thr Leu Phe Tyr Val Lys
            275                 280                 285 gag agc acc ctg tgg ctg acg tcc ttg aac gcc tgc ctt gat cca ttc     1035
Glu Ser Thr Leu Trp Leu Thr Ser Leu Asn Ala Cys Leu Asp Pro Phe
            290                 295                 300 atc tat ttc ttt ctt tgc aag tct ttc aga aat tcc ttg atg agc atg     1083
Ile Tyr Phe Phe Leu Cys Lys Ser Phe Arg Asn Ser Leu Met Ser Met
            305                 310                 315 ctg agg tgc tca aca tcc ggg gca aat aag aag aaa gga cag gaa ggt     1131
Leu Arg Cys Ser Thr Ser Gly Ala Asn Lys Lys Lys Gly Gln Glu Gly
            320                 325                 330 ggg gac cca agc gag gag acc cca atg tagaatgtta caggggggga           1178
Gly Asp Pro Ser Glu Glu Thr Pro Met
335                 340 ggacgggagg gttgcttcag tctttagtgt ccagactcct ccaaggaaat caccacataa    1238
atatattanc agtctctaaa aaaaaaaaaa aaaaaaaaaa aaaaaaaaa a              1289
```

<210> SEQ ID NO 2
<211> LENGTH: 343
<212> TYPE: PRT
<213> ORGANISM: Rattus norvegicus

<400> SEQUENCE: 2

```
Met Glu Val Pro Gly Ala Asn Ala Thr Ser Ala Asn Thr Thr Ser Ile
 1               5                  10                  15

Pro Gly Thr Ser Thr Leu Cys Ser Arg Asp Tyr Lys Ile Thr Gln Val
                20                  25                  30

Leu Phe Pro Leu Leu Tyr Thr Val Leu Phe Phe Ala Gly Leu Ile Thr
            35                  40                  45

Asn Ser Leu Ala Met Arg Ile Phe Phe Gln Ile Arg Ser Lys Ser Asn
        50                  55                  60

Phe Ile Ile Phe Leu Lys Asn Thr Val Ile Ser Asp Leu Leu Met Ile
 65                  70                  75                  80

Leu Thr Phe Pro Phe Lys Ile Leu Ser Asp Ala Lys Leu Gly Ala Gly
                85                  90                  95

His Leu Arg Thr Leu Val Cys Gln Val Thr Ser Val Thr Phe Tyr Phe
            100                 105                 110

Thr Met Tyr Ile Ser Ile Ser Phe Leu Gly Leu Ile Thr Ile Asp Arg
        115                 120                 125

Tyr Leu Lys Thr Thr Arg Pro Phe Lys Thr Ser Pro Ser Asn Leu
    130                 135                 140

Leu Gly Ala Lys Ile Leu Ser Val Ala Ile Trp Ala Phe Met Phe Leu
145                 150                 155                 160

Leu Ser Leu Pro Asn Met Ile Leu Thr Asn Arg Arg Pro Lys Asp Lys
                165                 170                 175

Asp Ile Thr Lys Cys Ser Phe Leu Lys Ser Glu Phe Gly Leu Val Trp
            180                 185                 190

His Glu Ile Val Asn Tyr Ile Cys Gln Val Ile Phe Trp Ile Asn Phe
        195                 200                 205

Leu Ile Val Ile Val Cys Tyr Ser Leu Ile Thr Lys Glu Leu Tyr Arg
    210                 215                 220

Ser Tyr Val Arg Thr Arg Gly Ser Ala Lys Ala Pro Lys Lys Arg Val
225                 230                 235                 240

Asn Ile Lys Val Phe Ile Ile Ile Ala Val Phe Phe Ile Cys Phe Val
                245                 250                 255
```

-continued

```
Pro Phe His Phe Ala Arg Ile Pro Tyr Thr Leu Ser Gln Thr Arg Ala
            260                 265                 270

Val Phe Asp Cys Asn Ala Glu Asn Thr Leu Phe Tyr Val Lys Glu Ser
        275                 280                 285

Thr Leu Trp Leu Thr Ser Leu Asn Ala Cys Leu Asp Pro Phe Ile Tyr
        290                 295                 300

Phe Phe Leu Cys Lys Ser Phe Arg Asn Ser Leu Met Ser Met Leu Arg
305                 310                 315                 320

Cys Ser Thr Ser Gly Ala Asn Lys Lys Gly Gln Glu Gly Asp
                325                 330                 335

Pro Ser Glu Glu Thr Pro Met
            340

<210> SEQ ID NO 3
<211> LENGTH: 1107
<212> TYPE: DNA
<213> ORGANISM: Homo sapiens
<220> FEATURE:
<221> NAME/KEY: CDS
<222> LOCATION: (163)..(1107)
<223> OTHER INFORMATION: Partial sequence of P2Y12 receptor

<400> SEQUENCE: 3
tccggaaaac tcatgaaatc ctctatcaca aagaggtttg gcaactaaac taagacatta      60
aaaggaaaat accagatgcc actctgcagg ctgcaataac tactacttac tggatacatt     120
caaaccctcc agaatcaaca gttatcaggt aaccaacaag aa atg caa gcc gtc       174
                                                Met Gln Ala Val
                                                  1 gac aac ctc acc tct gcg cct ggg aac acc agt ctg tgc acc aga gac       222
Asp Asn Leu Thr Ser Ala Pro Gly Asn Thr Ser Leu Cys Thr Arg Asp
  5                  10                  15                  20 tac aaa atc acc cag gtc ctc ttc cca ctg ctc tac act gtc ctg ttt       270
Tyr Lys Ile Thr Gln Val Leu Phe Pro Leu Leu Tyr Thr Val Leu Phe
                 25                  30                  35 ttt gtt gga ctt atc aca aat ggc ctg gcg atg agg att ttc ttt caa       318
Phe Val Gly Leu Ile Thr Asn Gly Leu Ala Met Arg Ile Phe Phe Gln
             40                  45                  50 atc cgg agt aaa tca aac ttt att att ttt ctt aag aac aca gtc att       366
Ile Arg Ser Lys Ser Asn Phe Ile Ile Phe Leu Lys Asn Thr Val Ile
         55                  60                  65 tct gat ctt ctc atg att ctg act ttt cca ttc aaa att ctt agt gat       414
Ser Asp Leu Leu Met Ile Leu Thr Phe Pro Phe Lys Ile Leu Ser Asp
 70                  75                  80 gcc aaa ctg gga aca gga cca ctg aga act ttt gtg tgt caa gtt acc       462
Ala Lys Leu Gly Thr Gly Pro Leu Arg Thr Phe Val Cys Gln Val Thr
 85                  90                  95                 100 tcc gtc ata ttt tat ttc aca atg tat atc agt att tca ttc ctg gga       510
Ser Val Ile Phe Tyr Phe Thr Met Tyr Ile Ser Ile Ser Phe Leu Gly
                105                 110                 115 ctg ata act atc gat cgc tac cag aag acc acc agg cca ttt aaa aca       558
Leu Ile Thr Ile Asp Arg Tyr Gln Lys Thr Thr Arg Pro Phe Lys Thr
            120                 125                 130 tcc aac ccc aaa aat ctc ttg ggg gct aag att ctc tct gtt gtc atc       606
Ser Asn Pro Lys Asn Leu Leu Gly Ala Lys Ile Leu Ser Val Val Ile
        135                 140                 145 tgg gca ttc atg ttc tta ctc tct ttg cct aac atg att ctg acc aac       654
Trp Ala Phe Met Phe Leu Leu Ser Leu Pro Asn Met Ile Leu Thr Asn
150                 155                 160
```

```
                                        -continued agg cag ccg aga gac aag aat gtg aag aaa tgc tct ttc ctt aaa tca      702
Arg Gln Pro Arg Asp Lys Asn Val Lys Lys Cys Ser Phe Leu Lys Ser
165                 170                 175                 180 gag ttc ggt cta gtc tgg cat gaa ata gta aat tac atc tgt caa gtc      750
Glu Phe Gly Leu Val Trp His Glu Ile Val Asn Tyr Ile Cys Gln Val
                185                 190                 195 att ttc tgg att aat ttc tta att gtt att gta tgt tat aca ctc att      798
Ile Phe Trp Ile Asn Phe Leu Ile Val Ile Val Cys Tyr Thr Leu Ile
            200                 205                 210 aca aaa gaa ctg tac cgg tca tac gta aga acg agg ggt gta ggt aaa      846
Thr Lys Glu Leu Tyr Arg Ser Tyr Val Arg Thr Arg Gly Val Gly Lys
        215                 220                 225 gtc ccc agg aaa aag gtg aac gtc aaa gtt ttc att atc att gct gta      894
Val Pro Arg Lys Lys Val Asn Val Lys Val Phe Ile Ile Ile Ala Val
    230                 235                 240 ttc ttt att tgt ttt gtt cct ttc cat ttt gcc cga att cct tac acc      942
Phe Phe Ile Cys Phe Val Pro Phe His Phe Ala Arg Ile Pro Tyr Thr
245                 250                 255                 260 ctg agc caa acc cgg gat gtc ttt gac tgc act gct gaa aat act ctg      990
Leu Ser Gln Thr Arg Asp Val Phe Asp Cys Thr Ala Glu Asn Thr Leu
                265                 270                 275 ttc tat gtg aaa gag agc act ctg tgg tta act tcc tta aat gca tgc     1038
Phe Tyr Val Lys Glu Ser Thr Leu Trp Leu Thr Ser Leu Asn Ala Cys
            280                 285                 290 ctg gat ccg ttc atc tat ttt ttc ctt tgc aag tcc ttc aga aat tcc     1086
Leu Asp Pro Phe Ile Tyr Phe Phe Leu Cys Lys Ser Phe Arg Asn Ser
        295                 300                 305 ttg ata agt atg ctg aag tgc                                         1107
Leu Ile Ser Met Leu Lys Cys
    310                 315

<210> SEQ ID NO 4
<211> LENGTH: 315
<212> TYPE: PRT
<213> ORGANISM: Homo sapiens

<400> SEQUENCE: 4

Met Gln Ala Val Asp Asn Leu Thr Ser Ala Pro Gly Asn Thr Ser Leu
1               5                   10                  15

Cys Thr Arg Asp Tyr Lys Ile Thr Gln Val Leu Phe Pro Leu Leu Tyr
            20                  25                  30

Thr Val Leu Phe Phe Val Gly Leu Ile Thr Asn Gly Leu Ala Met Arg
        35                  40                  45

Ile Phe Phe Gln Ile Arg Ser Lys Ser Asn Phe Ile Ile Phe Leu Lys
    50                  55                  60

Asn Thr Val Ile Ser Asp Leu Leu Met Ile Leu Thr Phe Pro Phe Lys
65                  70                  75                  80

Ile Leu Ser Asp Ala Lys Leu Gly Thr Gly Pro Leu Arg Thr Phe Val
            85                  90                  95

Cys Gln Val Thr Ser Val Ile Phe Tyr Phe Thr Met Tyr Ile Ser Ile
        100                 105                 110

Ser Phe Leu Gly Leu Ile Thr Ile Asp Arg Tyr Gln Lys Thr Thr Arg
    115                 120                 125

Pro Phe Lys Thr Ser Asn Pro Lys Asn Leu Leu Gly Ala Lys Ile Leu
130                 135                 140

Ser Val Val Ile Trp Ala Phe Met Phe Leu Leu Ser Leu Pro Asn Met
145                 150                 155                 160

Ile Leu Thr Asn Arg Gln Pro Arg Asp Lys Asn Val Lys Lys Cys Ser
```

-continued

```
                165                 170                 175
Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
    210                 215                 220

Gly Val Gly Lys Val Pro Arg Lys Val Asn Val Lys Val Phe Ile
225                 230                 235                 240

Ile Ile Ala Val Phe Phe Ile Cys Phe Val Pro Phe His Phe Ala Arg
            245                 250                 255

Ile Pro Tyr Thr Leu Ser Gln Thr Arg Asp Val Phe Asp Cys Thr Ala
        260                 265                 270

Glu Asn Thr Leu Phe Tyr Val Lys Glu Ser Thr Leu Trp Leu Thr Ser
    275                 280                 285

Leu Asn Ala Cys Leu Asp Pro Phe Ile Tyr Phe Leu Cys Lys Ser
290                 295                 300

Phe Arg Asn Ser Leu Ile Ser Met Leu Lys Cys
305                 310                 315
```

<210> SEQ ID NO 5
<211> LENGTH: 1330
<212> TYPE: DNA
<213> ORGANISM: Homo sapiens
<220> FEATURE:
<221> NAME/KEY: CDS
<222> LOCATION: (73)..(1098)
<223> OTHER INFORMATION: P2Y12 receptor

<400> SEQUENCE: 5

```
ctgcaataac tactacttac tggatacatt caaaccctcc agaatcaaca gttatcaggt        60
aaccaacaag aa atg caa gcc gtc gac aac ctc acc tct gcg cct ggg aac      111
              Met Gln Ala Val Asp Asn Leu Thr Ser Ala Pro Gly Asn
                1               5                  10 acc agt ctg tgc acc aga gac tac aaa atc acc cag gtc ctc ttc cca        159
Thr Ser Leu Cys Thr Arg Asp Tyr Lys Ile Thr Gln Val Leu Phe Pro
 15                  20                  25 ctg ctc tac act gtc ctg ttt ttt gtt gga ctt atc aca aat ggc ctg        207
Leu Leu Tyr Thr Val Leu Phe Phe Val Gly Leu Ile Thr Asn Gly Leu
 30                  35                  40                  45 gcg atg agg att ttc ttt caa atc cgg agt aaa tca aac ttt att att        255
Ala Met Arg Ile Phe Phe Gln Ile Arg Ser Lys Ser Asn Phe Ile Ile
                50                  55                  60 ttt ctt aag aac aca gtc att tct gat ctt ctc atg att ctg act ttt        303
Phe Leu Lys Asn Thr Val Ile Ser Asp Leu Leu Met Ile Leu Thr Phe
            65                  70                  75 cca ttc aaa att ctt agt gat gcc aaa ctg gga aca gga cca ctg aga        351
Pro Phe Lys Ile Leu Ser Asp Ala Lys Leu Gly Thr Gly Pro Leu Arg
        80                  85                  90 act ttt gtg tgt caa gtt acc tcc gtc ata ttt tat ttc aca atg tat        399
Thr Phe Val Cys Gln Val Thr Ser Val Ile Phe Tyr Phe Thr Met Tyr
    95                  100                 105 atc agt att tca ttc ctg gga ctg ata act atc gat cgc tac cag aag        447
Ile Ser Ile Ser Phe Leu Gly Leu Ile Thr Ile Asp Arg Tyr Gln Lys
110                 115                 120                 125 acc acc agg cca ttt aaa aca tcc aac ccc aaa aat ctc ttg ggg gct        495
Thr Thr Arg Pro Phe Lys Thr Ser Asn Pro Lys Asn Leu Leu Gly Ala
                130                 135                 140
```

```
aag att ctc tct gtt gtc atc tgg gca ttc atg ttc tta ctc tct ttg      543
Lys Ile Leu Ser Val Val Ile Trp Ala Phe Met Phe Leu Leu Ser Leu
            145                 150                 155 cct aac atg att ctg acc aac agg cag ccg aga gac aag aat gtg aag      591
Pro Asn Met Ile Leu Thr Asn Arg Gln Pro Arg Asp Lys Asn Val Lys
    160                 165                 170 aaa tgc tct ttc ctt aaa tca gag ttc ggt cta gtc tgg cat gaa ata      639
Lys Cys Ser Phe Leu Lys Ser Glu Phe Gly Leu Val Trp His Glu Ile
175                 180                 185 gta aat tac atc tgt caa gtc att ttc tgg att aat ttc tta att gtt      687
Val Asn Tyr Ile Cys Gln Val Ile Phe Trp Ile Asn Phe Leu Ile Val
190                 195                 200                 205 att gta tgt tat aca ctc att aca aaa gaa ctg tac cgg tca tac gta      735
Ile Val Cys Tyr Thr Leu Ile Thr Lys Glu Leu Tyr Arg Ser Tyr Val
                210                 215                 220 aga acg agg ggt gta ggt aaa gtc ccc agg aaa aag gtg aac gtc aaa      783
Arg Thr Arg Gly Val Gly Lys Val Pro Arg Lys Lys Val Asn Val Lys
            225                 230                 235 gtt ttc att atc att gct gta ttc ttt att tgt ttt gtt cct ttc cat      831
Val Phe Ile Ile Ile Ala Val Phe Phe Ile Cys Phe Val Pro Phe His
        240                 245                 250 ttt gcc cga att cct tac acc ctg agc caa acc cgg gat gtc ttt gac      879
Phe Ala Arg Ile Pro Tyr Thr Leu Ser Gln Thr Arg Asp Val Phe Asp
255                 260                 265 tgc act gct gaa aat act ctg ttc tat gtg aaa gag agc act ctg tgg      927
Cys Thr Ala Glu Asn Thr Leu Phe Tyr Val Lys Glu Ser Thr Leu Trp
270                 275                 280                 285 tta act tcc tta aat gca tgc ctg gat ccg ttc atc tat ttt ttc ctt      975
Leu Thr Ser Leu Asn Ala Cys Leu Asp Pro Phe Ile Tyr Phe Phe Leu
                290                 295                 300 tgc aag tcc ttc aga aat tcc ttg ata agt atg ctg aag tgc ccc aat     1023
Cys Lys Ser Phe Arg Asn Ser Leu Ile Ser Met Leu Lys Cys Pro Asn
            305                 310                 315 tct gca aca tct ctg tcc cag gac aat agg aaa aaa gaa cag gat ggt     1071
Ser Ala Thr Ser Leu Ser Gln Asp Asn Arg Lys Lys Glu Gln Asp Gly
        320                 325                 330 ggt gac cca aat gaa gag act cca atg taaacaaatt aactaaggaa           1118
Gly Asp Pro Asn Glu Glu Thr Pro Met
335                 340 atatttcaat ctctttgtgt tcagaactcg ttaaagcaaa gcgctaagta aaaatattaa   1178
ctgacgaaga agcaactaag ttaataataa tgactctaaa gaaacagaag attacaaaag   1238
caattttcat ttaccttttcc agtatgaaaa gctatcttaa aatatagaaa actaatctaa  1298
actgtagctg tattagcagc aaaacaaacg ac                                 1330

<210> SEQ ID NO 6
<211> LENGTH: 342
<212> TYPE: PRT
<213> ORGANISM: Homo sapiens

<400> SEQUENCE: 6

Met Gln Ala Val Asp Asn Leu Thr Ser Ala Pro Gly Asn Thr Ser Leu
1               5                   10                  15

Cys Thr Arg Asp Tyr Lys Ile Thr Gln Val Leu Phe Pro Leu Leu Tyr
            20                  25                  30

Thr Val Leu Phe Phe Val Gly Leu Ile Thr Asn Gly Leu Ala Met Arg
        35                  40                  45

Ile Phe Phe Gln Ile Arg Ser Lys Ser Asn Phe Ile Ile Phe Leu Lys
    50                  55                  60
```

```
Asn Thr Val Ile Ser Asp Leu Leu Met Ile Leu Thr Phe Pro Phe Lys
 65                  70                  75                  80

Ile Leu Ser Asp Ala Lys Leu Gly Thr Gly Pro Leu Arg Thr Phe Val
                 85                  90                  95

Cys Gln Val Thr Ser Val Ile Phe Tyr Phe Thr Met Tyr Ile Ser Ile
                100                 105                 110

Ser Phe Leu Gly Leu Ile Thr Ile Asp Arg Tyr Gln Lys Thr Thr Arg
            115                 120                 125

Pro Phe Lys Thr Ser Asn Pro Lys Asn Leu Leu Gly Ala Lys Ile Leu
        130                 135                 140

Ser Val Val Ile Trp Ala Phe Met Phe Leu Leu Ser Leu Pro Asn Met
145                 150                 155                 160

Ile Leu Thr Asn Arg Gln Pro Arg Asp Lys Asn Val Lys Lys Cys Ser
                165                 170                 175

Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
210                 215                 220

Gly Val Gly Lys Val Pro Arg Lys Lys Val Asn Val Lys Val Phe Ile
225                 230                 235                 240

Ile Ile Ala Val Phe Phe Ile Cys Phe Val Pro Phe His Phe Ala Arg
                245                 250                 255

Ile Pro Tyr Thr Leu Ser Gln Thr Arg Asp Val Phe Asp Cys Thr Ala
            260                 265                 270

Glu Asn Thr Leu Phe Tyr Val Lys Glu Ser Thr Leu Trp Leu Thr Ser
        275                 280                 285

Leu Asn Ala Cys Leu Asp Pro Phe Ile Tyr Phe Phe Leu Cys Lys Ser
290                 295                 300

Phe Arg Asn Ser Leu Ile Ser Met Leu Lys Cys Pro Asn Ser Ala Thr
305                 310                 315                 320

Ser Leu Ser Gln Asp Asn Arg Lys Lys Glu Gln Asp Gly Gly Asp Pro
                325                 330                 335

Asn Glu Glu Thr Pro Met
            340

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 7 cagaatcaa cagttatcag gtaacc                                           26

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 8
gtcagttaat attttttactt agcgctttgc                                     30
```

-continued

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 9
gtcaacgggg atgggaggca tga                                           23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 10
gtctgcctca tctcgaagga agg                                           23

<210> SEQ ID NO 11
<211> LENGTH: 1328
<212> TYPE: DNA
<213> ORGANISM: Homo sapiens
<220> FEATURE:
<221> NAME/KEY: CDS
<222> LOCATION: (73)..(873)
<223> OTHER INFORMATION: Mutated P2Y12 (2 base deletion) from patient ML

<400> SEQUENCE: 11

```
ctgcaataac tactacttac tggatacatt caaaccctcc agaatcaaca gttatcaggt      60
aaccaacaag aa atg caa gcc gtc gac aac ctc acc tct gcg cct ggg aac     111
              Met Gln Ala Val Asp Asn Leu Thr Ser Ala Pro Gly Asn
                1               5                  10 acc agt ctg tgc acc aga gac tac aaa atc acc cag gtc ctc ttc cca        159
Thr Ser Leu Cys Thr Arg Asp Tyr Lys Ile Thr Gln Val Leu Phe Pro
        15                  20                  25 ctg ctc tac act gtc ctg ttt ttt gtt gga ctt atc aca aat ggc ctg        207
Leu Leu Tyr Thr Val Leu Phe Phe Val Gly Leu Ile Thr Asn Gly Leu
 30                  35                  40                  45 gcg atg agg att ttc ttt caa atc cgg agt aaa tca aac ttt att att        255
Ala Met Arg Ile Phe Phe Gln Ile Arg Ser Lys Ser Asn Phe Ile Ile
                 50                  55                  60 ttt ctt aag aac aca gtc att tct gat ctt ctc atg att ctg act ttt        303
Phe Leu Lys Asn Thr Val Ile Ser Asp Leu Leu Met Ile Leu Thr Phe
             65                  70                  75 cca ttc aaa att ctt agt gat gcc aaa ctg gga aca gga cca ctg aga        351
Pro Phe Lys Ile Leu Ser Asp Ala Lys Leu Gly Thr Gly Pro Leu Arg
         80                  85                  90 act ttt gtg tgt caa gtt acc tcc gtc ata ttt tat ttc aca atg tat        399
Thr Phe Val Cys Gln Val Thr Ser Val Ile Phe Tyr Phe Thr Met Tyr
     95                  100                 105 atc agt att tca ttc ctg gga ctg ata act atc gat cgc tac cag aag        447
Ile Ser Ile Ser Phe Leu Gly Leu Ile Thr Ile Asp Arg Tyr Gln Lys
110                 115                 120                 125 acc acc agg cca ttt aaa aca tcc aac ccc aaa aat ctc ttg ggg gct        495
Thr Thr Arg Pro Phe Lys Thr Ser Asn Pro Lys Asn Leu Leu Gly Ala
                130                 135                 140 aag att ctc tct gtt gtc atc tgg gca ttc atg ttc tta ctc tct ttg        543
Lys Ile Leu Ser Val Val Ile Trp Ala Phe Met Phe Leu Leu Ser Leu
            145                 150                 155 cct aac atg att ctg acc aac agg cag ccg aga gac aag aat gtg aag        591
```

```
Pro Asn Met Ile Leu Thr Asn Arg Gln Pro Arg Asp Lys Asn Val Lys
        160                 165                 170 aaa tgc tct ttc ctt aaa tca gag ttc ggt cta gtc tgg cat gaa ata      639
Lys Cys Ser Phe Leu Lys Ser Glu Phe Gly Leu Val Trp His Glu Ile
    175                 180                 185 gta aat tac atc tgt caa gtc att ttc tgg att aat ttc tta att gtt      687
Val Asn Tyr Ile Cys Gln Val Ile Phe Trp Ile Asn Phe Leu Ile Val
190                 195                 200                 205 att gta tgt tat aca ctc att aca aaa gaa ctg tac cgg tca tac gta      735
Ile Val Cys Tyr Thr Leu Ile Thr Lys Glu Leu Tyr Arg Ser Tyr Val
                210                 215                 220 aga acg agg ggt gta ggt aaa gtc ccc agg aaa aag gtg aac gtc aaa      783
Arg Thr Arg Gly Val Gly Lys Val Pro Arg Lys Lys Val Asn Val Lys
                225                 230                 235 gtt ttt tat cat tgc tgt att ctt tat ttg ttt tgt tcc ttt cca ttt      831
Val Phe Tyr His Cys Cys Ile Leu Tyr Leu Phe Cys Ser Phe Pro Phe
                240                 245                 250 tgc ccg aat tcc tta cac cct gag cca aac ccg gga tgt ctt              873
Cys Pro Asn Ser Leu His Pro Glu Pro Asn Pro Gly Cys Leu
                255                 260                 265 tgactgcact gctgaaaata ctctgttcta tgtgaaagag agcactctgt ggttaacttc     933
cttaaatgca tgcctggatc cgttcatcta tttttccctt tgcaagtcct tcagaaattc     993
cttgataagt atgctgaagt gccccaattc tgcaacatct ctgtcccagg acaataggaa   1053
aaaagaacag gatggtggtg acccaaatga agagactcca atgtaaacaa attaactaag   1113
gaaatatttc aatctctttg tgttcagaac tcgttaaagc aaagcgctaa gtaaaaatat   1173
taactgacga agaagcaact aagttaataa taatgactct aaagaaacag aagattacaa   1233
aagcaatttt catttacctt tccagtatga aaagctatct aaaatatag aaaactaatc    1293 taaactgtag ctgtattagc agcaaaacaa acgac                             1328
```

<210> SEQ ID NO 12
<211> LENGTH: 267
<212> TYPE: PRT
<213> ORGANISM: Homo sapiens

<400> SEQUENCE: 12

```
Met Gln Ala Val Asp Asn Leu Thr Ser Ala Pro Gly Asn Thr Ser Leu
1               5                   10                  15

Cys Thr Arg Asp Tyr Lys Ile Thr Gln Val Leu Phe Pro Leu Leu Tyr
                20                  25                  30

Thr Val Leu Phe Phe Val Gly Leu Ile Thr Asn Gly Leu Ala Met Arg
            35                  40                  45

Ile Phe Phe Gln Ile Arg Ser Lys Ser Asn Phe Ile Ile Phe Leu Lys
        50                  55                  60

Asn Thr Val Ile Ser Asp Leu Leu Met Ile Leu Thr Phe Pro Phe Lys
65                  70                  75                  80

Ile Leu Ser Asp Ala Lys Leu Gly Thr Gly Pro Leu Arg Thr Phe Val
                85                  90                  95

Cys Gln Val Thr Ser Val Ile Phe Tyr Phe Thr Met Tyr Ile Ser Ile
                100                 105                 110

Ser Phe Leu Gly Leu Ile Thr Ile Asp Arg Tyr Gln Lys Thr Thr Arg
            115                 120                 125

Pro Phe Lys Thr Ser Asn Pro Lys Asn Leu Leu Gly Ala Lys Ile Leu
        130                 135                 140

Ser Val Val Ile Trp Ala Phe Met Phe Leu Leu Ser Leu Pro Asn Met
```

```
                    145                 150                 155                 160
Ile Leu Thr Asn Arg Gln Pro Arg Asp Lys Asn Val Lys Lys Cys Ser
                165                 170                 175

Phe Leu Lys Ser Glu Phe Gly Leu Val Trp His Glu Ile Val Asn Tyr
            180                 185                 190

Ile Cys Gln Val Ile Phe Trp Ile Asn Phe Leu Ile Val Ile Val Cys
        195                 200                 205

Tyr Thr Leu Ile Thr Lys Glu Leu Tyr Arg Ser Tyr Val Arg Thr Arg
    210                 215                 220

Gly Val Gly Lys Val Pro Arg Lys Lys Val Asn Val Lys Val Phe Tyr
225                 230                 235                 240

His Cys Cys Ile Leu Tyr Leu Phe Cys Ser Phe Pro Phe Cys Pro Asn
                245                 250                 255

Ser Leu His Pro Glu Pro Asn Pro Gly Cys Leu
            260                 265

<210> SEQ ID NO 13
<211> LENGTH: 338
<212> TYPE: PRT
<213> ORGANISM: Homo sapiens
<220> FEATURE:
<223> OTHER INFORMATION: UDP-glucose receptor; KIAA0001 gene product

<400> SEQUENCE: 13

Met Ile Asn Ser Thr Ser Thr Gln Pro Pro Asp Glu Ser Cys Ser Gln
  1               5                  10                  15

Asn Leu Leu Ile Thr Gln Gln Ile Ile Pro Val Leu Tyr Cys Met Val
                 20                  25                  30

Phe Ile Ala Gly Ile Leu Leu Asn Gly Val Ser Gly Trp Ile Phe Phe
             35                  40                  45

Tyr Val Pro Ser Ser Lys Ser Phe Ile Ile Tyr Leu Lys Asn Ile Val
        50                  55                  60

Ile Ala Asp Phe Val Met Ser Leu Thr Phe Pro Phe Lys Ile Leu Gly
 65                  70                  75                  80

Asp Ser Gly Leu Gly Pro Trp Gln Leu Asn Val Phe Val Cys Arg Val
                 85                  90                  95

Ser Ala Val Leu Phe Tyr Val Asn Met Tyr Val Ser Ile Val Phe Phe
            100                 105                 110

Gly Leu Ile Ser Phe Asp Arg Tyr Tyr Lys Ile Val Lys Pro Leu Trp
        115                 120                 125

Thr Ser Phe Ile Gln Ser Val Ser Tyr Ser Lys Leu Leu Ser Val Ile
    130                 135                 140

Val Trp Met Leu Met Leu Leu Leu Ala Val Pro Asn Ile Ile Leu Thr
145                 150                 155                 160

Asn Gln Ser Val Arg Glu Val Thr Gln Ile Lys Cys Ile Glu Leu Lys
                165                 170                 175

Ser Glu Leu Gly Arg Lys Trp His Lys Ala Ser Asn Tyr Ile Phe Val
            180                 185                 190

Ala Ile Phe Trp Ile Val Phe Leu Leu Ile Val Phe Tyr Thr Ala
        195                 200                 205

Ile Thr Lys Lys Ile Phe Lys Ser His Leu Lys Ser Ser Arg Asn Ser
    210                 215                 220

Thr Ser Val Lys Lys Lys Ser Ser Arg Asn Ile Phe Ser Ile Val Phe
225                 230                 235                 240

Val Phe Phe Val Cys Phe Val Pro Tyr His Ile Ala Arg Ile Pro Tyr
```

```
                    245                 250                 255
Thr Lys Ser Gln Thr Glu Ala His Tyr Ser Cys Gln Ser Lys Glu Ile
            260                 265                 270
Leu Arg Tyr Met Lys Glu Phe Thr Leu Leu Ser Ala Ala Asn Val
            275                 280                 285
Cys Leu Asp Pro Ile Ile Tyr Phe Leu Cys Gln Pro Phe Arg Glu
            290                 295                 300
Ile Leu Cys Lys Lys Leu His Ile Pro Leu Lys Ala Gln Asn Asp Leu
305                 310                 315                 320
Asp Ile Ser Arg Ile Lys Arg Gly Asn Thr Thr Leu Glu Ser Thr Asp
            325                 330                 335
Thr Leu

<210> SEQ ID NO 14
<211> LENGTH: 373
<212> TYPE: PRT
<213> ORGANISM: Homo sapiens
<220> FEATURE:
<223> OTHER INFORMATION: P2Y1 purinergic receptor; p2yr

<400> SEQUENCE: 14

Met Thr Glu Val Leu Trp Pro Ala Val Pro Asn Gly Thr Asp Ala Ala
1               5                   10                  15
Phe Leu Ala Gly Pro Gly Ser Ser Trp Gly Asn Ser Thr Val Ala Ser
            20                  25                  30
Thr Ala Ala Val Ser Ser Phe Lys Cys Ala Leu Thr Lys Thr Gly
            35                  40                  45
Phe Gln Phe Tyr Tyr Leu Pro Ala Val Tyr Ile Leu Val Phe Ile Ile
        50                  55                  60
Gly Phe Leu Gly Asn Ser Val Ala Ile Trp Met Phe Val Phe His Met
65                  70                  75                  80
Lys Pro Trp Ser Gly Ile Ser Val Tyr Met Phe Asn Leu Ala Leu Ala
                85                  90                  95
Asp Phe Leu Tyr Val Leu Thr Leu Pro Ala Leu Ile Phe Tyr Tyr Phe
            100                 105                 110
Asn Lys Thr Asp Trp Ile Phe Gly Asp Ala Met Cys Lys Leu Gln Arg
            115                 120                 125
Phe Ile Phe His Val Asn Leu Tyr Gly Ser Ile Leu Phe Leu Thr Cys
        130                 135                 140
Ile Ser Ala His Arg Tyr Ser Gly Val Val Tyr Pro Leu Lys Ser Leu
145                 150                 155                 160
Gly Arg Leu Lys Lys Lys Asn Ala Ile Cys Ile Ser Val Leu Val Trp
                165                 170                 175
Leu Ile Val Val Val Ala Ile Ser Pro Ile Leu Phe Tyr Ser Gly Thr
            180                 185                 190
Gly Val Arg Lys Asn Lys Thr Ile Thr Cys Tyr Asp Thr Thr Ser Asp
            195                 200                 205
Glu Tyr Leu Arg Ser Tyr Phe Ile Tyr Ser Met Cys Thr Thr Val Ala
        210                 215                 220
Met Phe Cys Val Pro Leu Val Leu Ile Leu Gly Cys Tyr Gly Leu Ile
225                 230                 235                 240
Val Arg Ala Leu Ile Tyr Lys Asp Leu Asp Asn Ser Pro Leu Arg Arg
                245                 250                 255
Lys Ser Ile Tyr Leu Val Ile Ile Val Leu Thr Val Phe Ala Val Ser
            260                 265                 270
```

```
Tyr Ile Pro Phe His Val Met Lys Thr Met Asn Leu Arg Ala Arg Leu
            275                 280                 285

Asp Phe Gln Thr Pro Ala Met Cys Ala Phe Asn Asp Arg Val Tyr Ala
        290                 295                 300

Thr Tyr Gln Val Thr Arg Gly Leu Ala Ser Leu Asn Ser Cys Val Asp
305                 310                 315                 320

Pro Ile Leu Tyr Phe Leu Ala Gly Asp Thr Phe Arg Arg Leu Ser
                325                 330                 335

Arg Ala Thr Arg Lys Ala Ser Arg Arg Ser Glu Ala Asn Leu Gln Ser
                340                 345                 350

Lys Ser Glu Asp Met Thr Leu Asn Ile Leu Pro Glu Phe Lys Gln Asn
            355                 360                 365

Gly Asp Thr Ser Leu
        370

<210> SEQ ID NO 15
<211> LENGTH: 374
<212> TYPE: PRT
<213> ORGANISM: Meleagris gallopavo
<220> FEATURE:
<223> OTHER INFORMATION: Turkey P2Y nucleotide receptor; tp2ynovel

<400> SEQUENCE: 15

Met Asp Ala Pro Val Arg Met Phe Ser Leu Ala Pro Trp Thr Pro Thr
1               5                   10                  15

Pro Thr Pro Trp Leu Gly Gly Asn Thr Ala Ala Glu Ala Lys
            20                  25                  30

Cys Val Phe Asn Glu Glu Phe Lys Phe Ile Leu Leu Pro Ile Ser Tyr
            35                  40                  45

Gly Ile Val Phe Val Val Gly Leu Pro Leu Asn Ser Trp Ala Met Trp
        50                  55                  60

Ile Phe Val Ser Arg Met Arg Pro Trp Asn Ala Thr Thr Thr Tyr Met
65                  70                  75                  80

Phe Asn Leu Ala Ile Ser Asp Thr Leu Tyr Val Phe Ser Leu Pro Thr
                85                  90                  95

Leu Val Tyr Tyr Tyr Ala Asp Arg Asn Asn Trp Pro Phe Gly Lys Val
            100                 105                 110

Phe Cys Lys Ile Val Arg Phe Leu Phe Tyr Ala Asn Leu Tyr Ser Ser
        115                 120                 125

Ile Leu Phe Leu Thr Cys Ile Ser Val His Arg Tyr Met Gly Ile Cys
    130                 135                 140

His Pro Ile Arg Ser Leu Lys Trp Val Lys Thr Lys His Ala Arg Leu
145                 150                 155                 160

Ile Cys Val Gly Val Trp Leu Val Val Thr Ile Cys Leu Ile Pro Asn
                165                 170                 175

Leu Ile Phe Val Thr Thr Ser Ser Lys Asp Asn Ser Thr Leu Cys His
                180                 185                 190

Asp Thr Thr Lys Pro Glu Glu Phe Asp His Tyr Val His Tyr Ser Ser
            195                 200                 205

Ser Ile Met Ala Leu Leu Phe Gly Ile Pro Phe Leu Val Ile Val Val
    210                 215                 220

Cys Tyr Cys Leu Met Ala Lys Arg Leu Cys Lys Arg Ser Phe Pro Ser
225                 230                 235                 240

Pro Ser Pro Arg Val Pro Ser Tyr Lys Lys Arg Ser Ile Lys Met Ile
                245                 250                 255
```

-continued

```
Ile Ile Val Leu Thr Val Phe Ala Ile Cys Phe Val Pro Phe His Ile
            260                 265                 270
Thr Arg Thr Leu Tyr Tyr Thr Ser Arg Tyr Phe Gln Ala Asp Cys Gln
        275                 280                 285
Thr Leu Asn Ile Ile Asn Phe Thr Tyr Lys Ile Thr Arg Pro Leu Ala
    290                 295                 300
Ser Ile Asn Ser Cys Leu Asp Pro Ile Leu Tyr Phe Met Ala Gly Asp
305                 310                 315                 320
Lys Tyr Arg Gly Arg Leu Arg Gly Ala Ala Gln Arg Pro Arg Pro
                325                 330                 335
Val Pro Thr Ser Leu Leu Ala Leu Val Ser Pro Ser Val Asp Ser Ser
            340                 345                 350
Val Val Gly Ser Cys Cys Asn Ser Glu Ser Arg Gly Met Gly Thr Val
            355                 360                 365
Trp Ser Arg Gly Gly Gln
    370
```

<210> SEQ ID NO 16
<211> LENGTH: 365
<212> TYPE: PRT
<213> ORGANISM: Homo sapiens
<220> FEATURE:
<223> OTHER INFORMATION: P2Y4 pyrimidinergic receptor

<400> SEQUENCE: 16

```
Met Ala Ser Thr Glu Ser Ser Leu Leu Arg Ser Leu Gly Leu Ser Pro
1               5                   10                  15
Gly Pro Gly Ser Ser Glu Val Glu Leu Asp Cys Trp Phe Asp Glu Asp
            20                  25                  30
Phe Lys Phe Ile Leu Leu Pro Val Ser Tyr Ala Val Val Phe Val Leu
        35                  40                  45
Gly Leu Gly Leu Asn Ala Pro Thr Leu Trp Leu Phe Ile Phe Arg Leu
    50                  55                  60
Arg Pro Trp Asp Ala Thr Ala Thr Tyr Met Phe His Leu Ala Leu Ser
65                  70                  75                  80
Asp Thr Leu Tyr Val Leu Ser Leu Pro Thr Leu Ile Tyr Tyr Tyr Ala
                85                  90                  95
Ala His Asn His Trp Pro Phe Gly Thr Glu Ile Cys Lys Phe Val Arg
            100                 105                 110
Phe Leu Phe Tyr Trp Asn Leu Tyr Cys Ser Val Leu Phe Leu Thr Cys
        115                 120                 125
Ile Ser Val His Arg Tyr Leu Gly Ile Cys His Pro Leu Arg Ala Leu
    130                 135                 140
Arg Trp Gly Arg Pro Arg Leu Ala Gly Leu Leu Cys Leu Ala Val Trp
145                 150                 155                 160
Leu Val Val Ala Gly Cys Leu Val Pro Asn Leu Phe Phe Val Thr Thr
                165                 170                 175
Ser Asn Lys Gly Thr Thr Val Leu Cys His Asp Thr Thr Arg Pro Glu
            180                 185                 190
Glu Phe Asp His Tyr Val His Phe Ser Ser Ala Val Met Gly Leu Leu
        195                 200                 205
Phe Gly Val Pro Cys Leu Val Thr Leu Val Cys Tyr Gly Leu Met Ala
    210                 215                 220
Arg Arg Leu Tyr Gln Pro Leu Pro Gly Ser Ala Gln Ser Ser Ser Arg
225                 230                 235                 240
```

-continued

Leu Arg Ser Leu Arg Thr Ile Ala Val Val Leu Thr Val Phe Ala Val
                245                 250                 255

Cys Phe Val Pro Phe His Ile Thr Arg Thr Ile Tyr Tyr Leu Ala Arg
            260                 265                 270

Leu Leu Glu Ala Asp Cys Arg Val Leu Asn Ile Val Asn Val Val Tyr
        275                 280                 285

Lys Val Thr Arg Pro Leu Ala Ser Ala Asn Ser Cys Leu Asp Pro Val
    290                 295                 300

Leu Tyr Leu Leu Thr Gly Asp Lys Tyr Arg Arg Gln Leu Arg Gln Leu
305                 310                 315                 320

Cys Gly Gly Gly Lys Pro Gln Pro Arg Thr Ala Ala Ser Ser Leu Ala
                325                 330                 335

Leu Val Ser Leu Pro Glu Asp Ser Ser Cys Arg Trp Ala Ala Thr Pro
            340                 345                 350

Gln Asp Ser Ser Cys Ser Thr Pro Arg Ala Asp Arg Leu
        355                 360                 365

<210> SEQ ID NO 17
<211> LENGTH: 377
<212> TYPE: PRT
<213> ORGANISM: Homo sapiens
<220> FEATURE:
<223> OTHER INFORMATION: P2Y2 purinergic receptor; p2ur

<400> SEQUENCE: 17

Met Ala Ala Asp Leu Gly Pro Trp Asn Asp Thr Ile Asn Gly Thr Trp
 1                5                  10                  15

Asp Gly Asp Glu Leu Gly Tyr Arg Cys Arg Phe Asn Glu Asp Phe Lys
                20                  25                  30

Tyr Val Leu Leu Pro Val Ser Tyr Gly Val Val Cys Val Leu Gly Leu
            35                  40                  45

Cys Leu Asn Ala Val Ala Leu Tyr Ile Phe Leu Cys Arg Leu Lys Thr
        50                  55                  60

Trp Asn Ala Ser Thr Thr Tyr Met Phe His Leu Ala Val Ser Asp Ala
 65                 70                  75                  80

Leu Tyr Ala Ala Ser Leu Pro Leu Leu Val Tyr Tyr Tyr Ala Arg Gly
                85                  90                  95

Asp His Trp Pro Phe Ser Thr Val Leu Cys Lys Leu Val Arg Phe Leu
            100                 105                 110

Phe Tyr Thr Asn Leu Tyr Cys Ser Ile Leu Phe Leu Thr Cys Ile Ser
        115                 120                 125

Val His Arg Cys Leu Gly Val Leu Arg Pro Leu Arg Ser Leu Arg Trp
    130                 135                 140

Gly Arg Ala Arg Tyr Ala Arg Arg Val Ala Gly Ala Val Trp Val Leu
145                 150                 155                 160

Val Leu Ala Cys Gln Ala Pro Val Leu Tyr Phe Val Thr Thr Ser Ala
                165                 170                 175

Arg Gly Gly Arg Val Thr Cys His Asp Thr Ser Ala Pro Glu Leu Phe
            180                 185                 190

Ser Arg Phe Val Ala Tyr Ser Ser Val Met Leu Gly Leu Leu Phe Ala
        195                 200                 205

Val Pro Phe Ala Val Ile Leu Val Cys Tyr Val Leu Met Ala Arg Arg
    210                 215                 220

Leu Leu Lys Pro Ala Tyr Gly Thr Ser Gly Gly Leu Pro Arg Ala Lys
225                 230                 235                 240

```
Arg Lys Ser Val Arg Thr Ile Ala Val Val Leu Ala Val Phe Ala Leu
                245                 250                 255

Cys Phe Leu Pro Phe His Val Thr Arg Thr Leu Tyr Tyr Ser Phe Arg
            260                 265                 270

Ser Leu Asp Leu Ser Cys His Thr Leu Asn Ala Ile Asn Met Ala Tyr
        275                 280                 285

Lys Val Thr Arg Pro Leu Ala Ser Ala Asn Ser Cys Leu Asp Pro Val
    290                 295                 300

Leu Tyr Phe Leu Ala Gly Gln Arg Leu Val Arg Phe Ala Arg Asp Ala
305                 310                 315                 320

Lys Pro Pro Thr Gly Pro Ser Pro Ala Thr Pro Ala Arg Arg Arg Leu
                325                 330                 335

Gly Leu Arg Arg Ser Asp Arg Thr Asp Met Gln Arg Ile Gly Asp Val
            340                 345                 350

Leu Gly Ser Ser Glu Asp Phe Arg Arg Thr Glu Ser Thr Pro Ala Gly
        355                 360                 365

Ser Glu Asn Thr Lys Asp Ile Arg Leu
    370                 375

<210> SEQ ID NO 18
<211> LENGTH: 328
<212> TYPE: PRT
<213> ORGANISM: Homo sapiens
<220> FEATURE:
<223> OTHER INFORMATION: P2Y6 receptor

<400> SEQUENCE: 18

Met Glu Trp Asp Asn Gly Thr Gly Gln Ala Leu Gly Leu Pro Pro Thr
  1               5                  10                  15

Thr Cys Val Tyr Arg Glu Asn Phe Lys Gln Leu Leu Leu Pro Pro Val
                 20                  25                  30

Tyr Ser Ala Val Leu Ala Ala Gly Leu Pro Leu Asn Ile Cys Val Ile
             35                  40                  45

Thr Gln Ile Cys Thr Ser Arg Arg Ala Leu Thr Arg Thr Ala Val Tyr
     50                  55                  60

Thr Leu Asn Leu Ala Leu Ala Asp Leu Leu Tyr Ala Cys Ser Leu Pro
 65                  70                  75                  80

Leu Leu Ile Tyr Asn Tyr Ala Gln Gly Asp His Trp Pro Phe Gly Asp
                 85                  90                  95

Phe Ala Cys Arg Leu Val Arg Phe Leu Phe Tyr Ala Asn Leu His Gly
            100                 105                 110

Ser Ile Leu Phe Leu Thr Cys Ile Ser Phe Gln Arg Tyr Leu Gly Ile
        115                 120                 125

Cys His Pro Leu Ala Pro Trp His Lys Arg Gly Gly Arg Arg Ala Ala
    130                 135                 140

Trp Leu Val Cys Val Ala Val Trp Leu Ala Val Thr Thr Gln Cys Leu
145                 150                 155                 160

Pro Thr Ala Ile Phe Ala Ala Thr Gly Ile Gln Arg Asn Arg Thr Val
                165                 170                 175

Cys Tyr Asp Leu Ser Pro Pro Ala Leu Ala Thr His Tyr Met Pro Tyr
            180                 185                 190

Gly Met Ala Leu Thr Val Ile Gly Phe Leu Leu Pro Phe Ala Ala Leu
        195                 200                 205

Leu Ala Cys Tyr Cys Leu Leu Ala Cys Arg Leu Cys Arg Gln Asp Gly
    210                 215                 220
```

-continued

```
Pro Ala Glu Pro Val Ala Gln Glu Arg Arg Gly Lys Ala Ala Arg Met
225                 230                 235                 240

Ala Val Val Ala Ala Phe Ala Ile Ser Phe Leu Pro Phe His
            245                 250                 255

Ile Thr Lys Thr Ala Tyr Leu Ala Val Arg Ser Thr Pro Gly Val Pro
                260                 265                 270

Cys Thr Val Leu Glu Ala Phe Ala Ala Tyr Lys Gly Thr Arg Pro
            275                 280                 285

Phe Ala Ser Ala Asn Ser Val Leu Asp Pro Ile Leu Phe Tyr Phe Thr
            290                 295                 300

Gln Lys Lys Phe Arg Arg Pro His Glu Leu Leu Gln Lys Leu Thr
305                 310                 315                 320

Ala Lys Trp Gln Arg Gln Gly Arg
                325
```

<210> SEQ ID NO 19
<211> LENGTH: 371
<212> TYPE: PRT
<213> ORGANISM: Homo sapiens
<220> FEATURE:
<223> OTHER INFORMATION: P2Y11 puringergic receptor

<400> SEQUENCE: 19

```
Met Asp Arg Gly Ala Lys Ser Cys Pro Ala Asn Phe Leu Ala Ala
  1               5                  10                  15

Asp Asp Lys Leu Ser Gly Phe Gln Gly Asp Phe Leu Trp Pro Ile Leu
                 20                  25                  30

Val Val Glu Phe Leu Val Ala Val Ala Ser Asn Gly Leu Ala Leu Tyr
             35                  40                  45

Arg Phe Ser Ile Arg Lys Gln Arg Pro Trp His Pro Ala Val Val Phe
         50                  55                  60

Ser Val Gln Leu Ala Val Ser Asp Leu Leu Cys Ala Leu Thr Leu Pro
 65                  70                  75                  80

Pro Leu Ala Ala Tyr Leu Tyr Pro Pro Lys His Trp Arg Tyr Gly Glu
                 85                  90                  95

Ala Ala Cys Arg Leu Glu Arg Phe Leu Phe Thr Cys Asn Leu Leu Gly
                100                 105                 110

Ser Val Ile Phe Ile Thr Cys Ile Ser Leu Asn Arg Tyr Leu Gly Ile
            115                 120                 125

Val His Pro Phe Phe Ala Arg Ser His Leu Arg Pro Lys His Ala Trp
        130                 135                 140

Ala Val Ser Ala Ala Gly Trp Val Leu Ala Ala Leu Leu Ala Met Pro
145                 150                 155                 160

Thr Leu Ser Phe Ser His Leu Lys Arg Pro Gln Gln Gly Ala Gly Asn
                165                 170                 175

Cys Ser Val Ala Arg Pro Glu Ala Cys Ile Lys Cys Leu Gly Thr Ala
            180                 185                 190

Asp His Gly Leu Ala Ala Tyr Arg Ala Tyr Ser Leu Val Leu Ala Gly
        195                 200                 205

Leu Gly Cys Gly Leu Pro Leu Leu Leu Thr Leu Ala Ala Tyr Gly Ala
    210                 215                 220

Leu Gly Arg Ala Val Leu Arg Ser Pro Gly Met Thr Val Ala Glu Lys
225                 230                 235                 240

Leu Arg Val Ala Ala Leu Val Ala Ser Gly Val Ala Leu Tyr Ala Ser
                245                 250                 255
```

Ser Tyr Val Pro Tyr His Ile Met Arg Val Leu Asn Val Asp Ala Arg
            260                 265                 270

Arg Arg Trp Ser Thr Arg Cys Pro Ser Phe Ala Asp Ile Ala Gln Ala
        275                 280                 285

Thr Ala Ala Leu Glu Leu Gly Pro Tyr Val Gly Tyr Gln Val Met Arg
    290                 295                 300

Gly Leu Met Pro Leu Ala Phe Cys Val His Pro Leu Leu Tyr Met Ala
305                 310                 315                 320

Ala Val Pro Ser Leu Gly Cys Cys Arg His Cys Pro Gly Tyr Arg
                325                 330                 335

Asp Ser Trp Asn Pro Glu Asp Ala Lys Ser Thr Gly Gln Ala Leu Pro
            340                 345                 350

Leu Asn Ala Thr Ala Ala Pro Lys Pro Ser Glu Pro Gln Ser Arg Glu
                355                 360                 365

Leu Ser Gln
    370

<210> SEQ ID NO 20
<211> LENGTH: 319
<212> TYPE: PRT
<213> ORGANISM: Homo sapiens
<220> FEATURE:
<223> OTHER INFORMATION: Platelet activating receptor homolog; pafo14626

<400> SEQUENCE: 20

Met Thr Asn Ser Ser Phe Phe Cys Pro Val Tyr Lys Asp Leu Glu Pro
1               5                   10                  15

Phe Thr Tyr Phe Phe Tyr Leu Val Phe Leu Val Gly Ile Ile Gly Ser
            20                  25                  30

Cys Phe Ala Thr Trp Ala Phe Ile Gln Lys Asn Thr Asn His Arg Cys
        35                  40                  45

Val Ser Ile Tyr Leu Ile Asn Leu Leu Thr Ala Asp Phe Leu Leu Thr
    50                  55                  60

Leu Ala Leu Pro Val Lys Ile Val Asp Leu Gly Val Ala Pro Trp
65                  70                  75                  80

Lys Leu Lys Ile Phe His Cys Gln Val Thr Ala Cys Leu Ile Tyr Ile
                85                  90                  95

Asn Met Tyr Leu Ser Ile Ile Phe Leu Ala Phe Val Ser Ile Asp Arg
            100                 105                 110

Cys Leu Gln Leu Thr His Ser Cys Lys Ile Tyr Arg Ile Gln Glu Pro
        115                 120                 125

Gly Phe Ala Lys Met Ile Ser Thr Val Val Trp Leu Met Val Leu Leu
130                 135                 140

Ile Met Val Pro Asn Met Met Ile Pro Ile Lys Asp Ile Lys Glu Lys
145                 150                 155                 160

Ser Asn Val Gly Cys Met Glu Phe Lys Lys Glu Phe Gly Arg Asn Trp
                165                 170                 175

His Leu Leu Thr Asn Phe Ile Cys Val Ala Ile Phe Leu Asn Phe Ser
            180                 185                 190

Ala Ile Ile Leu Ile Ser Asn Cys Leu Val Ile Arg Gln Leu Tyr Arg
        195                 200                 205

Asn Lys Asp Asn Glu Asn Tyr Pro Asn Val Lys Lys Ala Leu Ile Asn
    210                 215                 220

Ile Leu Leu Val Thr Thr Gly Tyr Ile Ile Cys Phe Val Pro Tyr His
225                 230                 235                 240

```
Ile Val Arg Ile Pro Tyr Thr Leu Ser Gln Thr Glu Val Ile Thr Asp
                245                 250                 255

Cys Ser Thr Arg Ile Ser Leu Phe Lys Ala Lys Glu Ala Thr Leu Leu
                260                 265                 270

Leu Ala Val Ser Asn Leu Cys Phe Asp Pro Ile Leu Tyr Tyr His Leu
                275                 280                 285

Ser Lys Ala Phe Arg Ser Lys Val Thr Glu Thr Phe Ala Ser Pro Lys
                290                 295                 300

Glu Thr Lys Ala Gln Lys Glu Lys Leu Arg Cys Glu Asn Asn Ala
305                 310                 315

<210> SEQ ID NO 21
<211> LENGTH: 381
<212> TYPE: PRT
<213> ORGANISM: Homo sapiens
<220> FEATURE:
<223> OTHER INFORMATION: G protein-coupled receptor 34; hugpr34

<400> SEQUENCE: 21

Met Arg Ser His Thr Ile Thr Met Thr Thr Thr Ser Val Ser Ser Trp
1               5                   10                  15

Pro Tyr Ser Ser His Arg Met Arg Phe Ile Thr Asn His Ser Asp Gln
                20                  25                  30

Pro Pro Gln Asn Phe Ser Ala Thr Pro Asn Val Thr Thr Cys Pro Met
            35                  40                  45

Asp Glu Lys Leu Leu Ser Thr Val Leu Thr Thr Ser Tyr Ser Val Ile
        50                  55                  60

Phe Ile Val Gly Leu Val Gly Asn Ile Ile Ala Leu Tyr Val Phe Leu
65                  70                  75                  80

Gly Ile His Arg Lys Arg Asn Ser Ile Gln Ile Tyr Leu Leu Asn Val
                85                  90                  95

Ala Ile Ala Asp Leu Leu Leu Ile Phe Cys Leu Pro Phe Arg Ile Met
                100                 105                 110

Tyr His Ile Asn Gln Asn Lys Trp Thr Leu Gly Val Ile Leu Cys Lys
                115                 120                 125

Val Val Gly Thr Leu Phe Tyr Met Asn Met Tyr Ile Ser Ile Ile Leu
                130                 135                 140

Leu Gly Phe Ile Ser Leu Asp Arg Tyr Ile Lys Ile Asn Arg Ser Ile
145                 150                 155                 160

Gln Gln Arg Lys Ala Ile Thr Thr Lys Gln Ser Ile Tyr Val Cys Cys
                165                 170                 175

Ile Val Trp Met Leu Ala Leu Gly Gly Phe Leu Thr Met Ile Ile Leu
                180                 185                 190

Thr Leu Lys Lys Gly Gly His Asn Ser Thr Met Cys Phe His Tyr Arg
                195                 200                 205

Asp Lys His Asn Ala Lys Gly Glu Ala Ile Phe Asn Phe Ile Leu Val
                210                 215                 220

Val Met Phe Trp Leu Ile Phe Leu Leu Ile Ile Leu Ser Tyr Ile Lys
225                 230                 235                 240

Ile Gly Lys Asn Leu Leu Arg Ile Ser Lys Arg Ser Lys Phe Pro
                245                 250                 255

Asn Ser Gly Lys Tyr Ala Thr Thr Ala Arg Asn Ser Phe Ile Val Leu
                260                 265                 270

Ile Ile Phe Thr Ile Cys Phe Val Pro Tyr His Ala Phe Arg Phe Ile
                275                 280                 285
```

```
Tyr Ile Ser Ser Gln Leu Asn Val Ser Ser Cys Tyr Trp Lys Glu Ile
    290             295             300

Val His Lys Thr Asn Glu Ile Met Leu Val Leu Ser Ser Phe Asn Ser
305             310             315             320

Cys Leu Asp Pro Val Met Tyr Phe Leu Met Ser Ser Asn Ile Arg Lys
            325             330             335

Ile Met Cys Gln Leu Leu Phe Arg Arg Phe Gln Gly Glu Pro Ser Arg
            340             345             350

Ser Glu Ser Thr Ser Glu Phe Lys Pro Gly Tyr Ser Leu His Asp Thr
        355             360             365

Ser Val Ala Val Lys Ile Gln Ser Ser Ser Lys Ser Thr
    370             375             380
```

References

Bennett, C. L. et al. Thrombotic thrombocytopenic purpura associated with Clopidogrel. N. Eng. J. Med. 325, 1371–2 (2000).

Boyer, J. L., Lazarowski, E. R., Chen, X. H. & Harden, T. K. Identification of a P2Y-purinergic receptor that inhibits adenylyl cyclase. J Pharmacol Exp Ther 267, 1140–6 (1993).

Boyer, J. L., Romero-Avila, T., Schachter, J. B. & Harden, T. K. Identification of competitive antagonists of the $P2Y_1$ receptor. Mol Pharmacol 50, 1323–9 (1996).

Caterina, M. J. et al. The capsaicin receptor: a heat-activated ion channel in the pain pathway. Nature 389, 816–824 (1997)

Cattaneo, M. & Gachet, C. ADP receptors and clinical bleeding disorders. Arterioscler Thromb Vasc Biol 19, 2281–5 (1999).

Chambers, J. K. et al. A G protein-coupled receptor for UDP-glucose. J Biol Chem 275, 10767–71 (2000).

Daniel, J. L. et al. Molecular basis for ADP-induced platelet activation. I. Evidence for three distinct ADP receptors on human platelets. J Biol Chem 273, 2024–9 (1998).

Fabre, J. E. et al. Decreased platelet aggregation, increased bleeding time and resistance to thromboembolism in P2Y1-deficient mice. Nat Med 5, 1199–202 (1999).

Filippov, A. K., Brown, D. A. & Barnard, E. A. The P2Y1 receptor closes the N-type Ca(2+) channel in neurones, with both adenosine triphosphates and diphosphates as potent agonists. Br J Pharmacol 129, 1063–6 (2000).

Gachet, C. et al. ADP receptor induced activation of guanine nucleotide binding proteins in rat platelet membranes—an effect selectively blocked by the thienopyridine clopidogrel. Thromb Haemost 68, 79–83 (1992).

Gachet, C. et al. The thienopyridine ticlopidine selectively prevents the inhibitory effects of ADP but not of adrenaline on cAMP levels raised by stimulation of the adenylate cyclase of human platelets by PGE1. Biochem Pharmacol 40, 2683–7 (1990).

Hechler, B., Eckly, A., Ohlmann, P., Cazenave, J.-P. & Gachet, C. The P2Y1 receptor, necessary but not sufficient to support full ADP-induced platelet aggregation, is not the target of the drug clopidogrel. Br. J. Haematology 103, 858–866 (1998).

Hourani, S. M. O. & Hall, D. Receptors for ADP on human blood platelets. Trends Pharmacol. Sci. 15, 103–108 (1994).

Humbert, M. et al. Ultrastructural studies of platelet aggregates from human subjects receiving clopidogrel and from a patient with an inherited defect of an ADP-dependent pathway of platelet activation. Arterioscler Thromb Vasc Biol 16, 1532–43 (1996).

Humphries, R. G., Tomlinson, W., Ingall, A. H., Cage, P. A. & Leff, P. A novel, highly potent and selective antagonist at human platelet P2T-purinoreceptors. Br. J. Pharmacol. 113, 1057–1063 (1994).

Jantzen, H.-M. et al. Evidence for two distinct G protein-coupled ADP receptors mediating platelet activation. Blood 92, 303a (1998).

Jantzen, H. M. et al. Evidence for two distinct G-protein-coupled ADP receptors mediating platelet activation. Thromb Haemost 81, 111–7 (1999).

Jarvis, G. E., Humphries, R. G., Robertson, M. J. & Leff, P. ADP can induce aggregation of human platelets via both P2Y(1) and P(2T) receptors. Br J Pharmacol 129, 275–82 (2000).

Krapivinsky, G., Krapivinsky, L., Wickman, K. & Clapham, D. G bg binds directly to the G protein-gated K+ channel, IKACh. J. Biol. Chem. 270, 29059–62 (1995).

Leon, C. et al. Defective platelet aggregation and increased resistance to thrombosis in purinergic P2Y1 receptor-null mice. J Clin Invest 104, 1731–7 (1999).

MacFarlane, D. E., Srivastava, P. C. & Mills, D. C. B. 2-Methylthioadenosine[b-32P]diphosphate: An agonist and radioligand for the receptor that inhibits the accumulation of cyclic AMP in intact blood platelets. J. Clin. Invest. 71, 420–428 (1983).

Mills, D. C. ADP receptors on platelets. Thromb Haemost 76, 835–56 (1996).

Mills, D. C. B. et al. Clopidogrel inhibits the binding of ADP analogues to the receptor mediating inhibition of platelet adenylate cyclase. Arterioscler. Thromb. 12, 430–436 (1992).

Nurden, P. et al. An inherited bleeding disorder linked to a defective interaction between ADP and its receptor on platelets. J. Clin. Invest. 95, 1612–22 (1995).

Ohlmann, P. et al. The human platelet ADP receptor activates Gi2 proteins. Biochem J 312, 775–9 (1995).

Palmer, R. K., Boyer, J. L., Schachter, J. B., Nicholas, R. A. & Harden, T. K. Agonist action of adenosine triphosphates at the human P2Y1 receptor. Mol Pharmacol 54, 1118–23 (1998).

Savi, P. et al. Structure and activity of the active metabolite of Clopidogrel. Thrombosis and Haemostasis 82, 230 (1999).

Stewart, E. et al. An STS-based radiation hybrid map of the human genome. Genome Res. 7, 422–33 (1997).

What is claimed:

1. A method of identifying an agent which modulates at least one activity of a P2Y12 receptor protein comprising:

a) exposing a cell or a portion thereof, that is genetically altered to express the P2Y12 receptor protein, to ADP or a derivative of ADP, in the presence of the agent, wherein the P2Y12 receptor protein is a protein, or an ADP binding fragment thereof, which is encoded by a nucleic acid molecule which hybridizes under stringent conditions comprising incubating in 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C. with washes at 42° C. in 0.2×SSC and 0.1% SDS, to a nucleic acid molecule selected from the group consisting of SEQ ID NO:1 and a complement thereof and wherein said nucleic acid molecule encodes a polypeptide having a P2Y12 activity; and b) determining whether the agent modulates at least one activity of the P2Y12 receptor protein.

2. The method of claim 1, wherein the portion of the cell which is genetically altered to express the P2Y12 receptor protein comprises a cell membrane of the cell which expresses the P2Y12 receptor protein.

3. The method of claim 1, wherein the nucleic acid molecule is selected from the group consisting of SEQ ID NO:1 and a complement thereof.

4. The method of claim 1, wherein the P2Y12 receptor activity is selected from the group consisting of potassium current, calcium flux, adenylyl cyclase activity, ADP binding activity, and platelet activation.

5. The method of claim 4, wherein the platelet activation is selected from the group consisting of platelet aggregation and platelet degranulation.

6. The method of claim 5, wherein the platelet degranulation results in release of ADP.

7. A method of identifying an agent which modulates at least one activity of a P2Y12 receptor protein comprising:

a) exposing the P2Y12 receptor protein to ADP, or a derivative of ADP, in the presence of the agent, wherein the P2Y12 receptor protein is a protein, or an ADP binding fragment thereof, which is encoded by a nucleic acid molecule which hybridizes under stringent conditions comprising incubating in 50% formamide, 5×SSC (0.75M NaCl, 0.075 M sodium citrate), 50 mM sodium phosphate (pH 6.8), 0.1% sodium pyrophosphate, 5× Denhardt's solution, sonicated salmon sperm DNA (50 g/ml), 0.1% SDS, and 10% dextran sulfate at 42° C., with washes at 42° C. in 0.2×SSC and 0.1% SDS, to a nucleic acid molecule selected from the group consisting of SEQ ID NO:1 and a complement thereof and wherein said nucleic acid molecule encodes a polypeptide having a P2Y12 activity;

b) determining whether the agent binds to the P2Y12 receptor protein: and c) determining whether the agent modulates at least one activity of the P2Y12 receptor protein.

8. The method of claim 7, wherein the P2Y12 receptor protein comprises a cell membrane of a cell which expresses the P2Y12 receptor protein.

9. The method of claim 7, wherein the nucleic acid molecule is selected from the group consisting of SEQ ID NO:1 and a complement thereof.

10. The method of claim 7, wherein the P2Y12 receptor protein comprises a cell which expresses the receptor.

11. The method of claim 10, wherein the cell which expresses the receptor is a cell which is transfected with a nucleic acid molecule which encodes the P2Y12 receptor protein.

12. The method of claim 10, wherein the cell which expresses the receptor is a cell which naturally expresses the P2Y12 receptor protein.

13. The method of claim 12, wherein the cell is a platelet or glial cell.

14. The method of claim 7, wherein the P2Y12 receptor activity is selected from the group consisting of potassium current, calcium flux, adenylyl cyclase activity, ADP binding activity, and platelet activation.

15. The method of claim 14, wherein the platelet activation is selected from the group consisting of platelet aggregation and platelet degranulation.

16. The method of claim 15, wherein the platelet degranulation results in release of ADP.

17. A method of identifying an agent which modulates at least one ADP-dependent activity of a P2Y12 receptor comprising:

a) exposing a P2Y12 receptor protein encoded by SEQ ID NO:1 to the agent and to ADP, or a derivative of ADP, under conditions in which ADP will bind to a P2Y12 receptor; and;

b) detecting or measuring at least one ADP-dependent activity of the P2Y12 receptor, wherein said P2Y12 receptor is a member of the G protein-coupled receptor superfamily, binds ADP and is a Gi-linked receptor wherein a change in at least one ADP-dependent activity of the P2Y12 receptor in the presence of the agent as compared to in the absence of the agent is indicative that the agent is a modulator of the ADP-dependent activity of the P2Y12 receptor.

* * * * *